US008821937B2

(12) United States Patent
Darlington, Jr.

(10) Patent No.: US 8,821,937 B2
(45) Date of Patent: Sep. 2, 2014

(54) METHODS OF TREATING CARDIOVASCULAR DISORDERS ASSOCIATED WITH ATHEROSCLEROSIS

(75) Inventor: Jerald W. Darlington, Jr., Marengo, IL (US)

(73) Assignee: Amcol International Corporation, Hoffman Estates, IL (US)

(*) Notice: Subject to any disclaimer, the term of this patent is extended or adjusted under 35 U.S.C. 154(b) by 790 days.

(21) Appl. No.: 12/394,819

(22) Filed: Feb. 27, 2009

(65) Prior Publication Data

US 2009/0186091 A1 Jul. 23, 2009

Related U.S. Application Data

(63) Continuation-in-part of application No. 12/124,748, filed on May 21, 2008.

(60) Provisional application No. 60/966,557, filed on May 23, 2007, provisional application No. 61/031,931, filed on Feb. 27, 2008.

(51) Int. Cl.
*A61K 9/14* (2006.01)
*A01N 59/00* (2006.01)
*A61K 33/00* (2006.01)

(52) U.S. Cl.
USPC .......................... 424/489; 424/722; 424/724

(58) Field of Classification Search
USPC ........................................ 424/489, 722, 724
See application file for complete search history.

(56) References Cited

U.S. PATENT DOCUMENTS

| | | | | | |
|---|---|---|---|---|---|
| 4,096,278 | A | * | 6/1978 | Queuille | 514/642 |
| 4,180,566 | A | | 12/1979 | Winyall et al. | |
| 4,514,510 | A | * | 4/1985 | Alexander | 501/148 |
| 6,050,509 | A | | 4/2000 | Clarey et al. | |
| 6,165,440 | A | | 12/2000 | Esenaliev | |
| 6,184,037 | B1 | | 2/2001 | Rolland | |
| 6,207,456 | B1 | | 3/2001 | Baru et al. | |
| 6,217,912 | B1 | | 4/2001 | Park et al. | |
| 6,287,576 | B1 | | 9/2001 | Bgatov et al. | |
| 6,468,964 | B1 | * | 10/2002 | Rowe | 424/94.61 |
| 2002/0192203 | A1 | * | 12/2002 | Cho et al. | 424/94.1 |
| 2005/0181015 | A1 | * | 8/2005 | Zhong | 424/426 |
| 2007/0231412 | A1 | * | 10/2007 | Hughes et al. | 424/683 |

FOREIGN PATENT DOCUMENTS

| | | |
|---|---|---|
| EP | 0 291 960 A2 | 11/1988 |
| EP | 0 778 027 A2 | 6/1997 |
| EP | 0 985 411 | 3/2000 |
| JP | 62223108 | 10/1987 |
| JP | 09235234 | 9/1997 |
| KR | 2003-0076536 | 9/2003 |
| WO | WO-2007/038596 A2 | 4/2007 |

OTHER PUBLICATIONS

Bisgaier et al., "A novel compound that elevates high density lipoprotein and activates the peroxisome proliferator activated receptor," *J. Lipid Res.*, 39:17-30 (1998).
Borel et al., "Wheat bran and wheat germ: effect on digestion and intestinal absorption of dietary lipids in the rat," *Am. J. Clin. Nutr.*, 49:1192-1202 (1989).
Burnett et al., "Cholesterol absorption inhibitors as a therapeutic option for hypercholesterolaemia," *Expert Opin. Investig. Drugs.*, 5(11):1337-51 (2006).
Carr et al., "Increased Intestinal Contents Viscosity Reduces Cholesterol Absorption Efficiency in Hamsters Fed Hydroxypropyl Methylcellulose," *J. Nutr.* 126:1463-1469 (1996).
Carretero, "Clay minerals and their beneficial effects upon human health," *App. Clay Sci.*, 21:155-163 (2002).
Hauss et al., "Chronic Collection of Mesenteric Lymph From Conscious, Tethered Rats," Contemp. Top Lab Anim. Sci., 37(3):56-58 (1998).
Heidrich et al., "Inhibition of pancreatic cholesterol esterase reduces cholesterol absorption in the hamster," BMC Pharmacology, 4:5, (2004).
International Search Report for PCT/US08/064351, from the European Patent Office as the International Searching Authority, dated Jan. 30, 2009.
Kimura et al., "Effects of soluble sodium alginate on cholesterol excretion and glucose tolerance in rats," *J. Ethnopharmacol*, 54(1):47-54 (1996).
Kocoshis et al., "In Vitro Bile Acid Adsorption by Bismuth Subsalicylate and Montmorillonite," *Dig. Dis. Sci.*, 24:1148-1152 (1984).
Kolodgie et al., "Hypercholesterolemia in the Rabbit Induced by Feeding Graded Amounts of Low-Level Cholesterol: Methodological Considerations Regarding Individual Variability in Response to Dietary Cholesterol and Development of Lesion Type," *Arterioscler. Thromb. Vasc. Biol.*, 16:1454-1464 (1996).
Kono et al., reen Tea Consumption and Serum Lipid Profiles: A Cross-Sectional Study in Northern Kyushu, Japan, *Prev. Med.*, 21:526-31 (1992).
Kroon et al., "The Effects of Mevinolin on Serum Cholesterol Levels of Rabbits with Endogenous Hypercholesterolemia," *Atherosclerosis*, 44:41-48 (1982).
Lewis et al., "Effects of 2164U90 on ileal bile acid absorption and serum cholesterol in rats and mice," *J. Lipid Res.*, 36:1098-1105 (1995).
Lukic et al., "Disodium Ascorbyl Phytostanyl Phosphate Reduces Plasma Cholesterol Concentrations and Atherosclerotic Lesion Formation in Apolipoprotein E-Deficient Mice," *Metabolism*, 52(4):425-431 (2003).

(Continued)

*Primary Examiner* — Gina C Justice
*Assistant Examiner* — Genevieve S Alley
(74) *Attorney, Agent, or Firm* — Marshall, Gerstein & Borun LLP

(57) ABSTRACT

Layered phyllosilicates are useful for adsorbing and/or binding to cholesterol and, thereby, reducing blood cholesterol in a patient. Accordingly, provided herein is a method of reducing hypercholesteremia in a mammal comprising administering to the mammal a protonated and at least partially exfoliated layered phyllosilicate material alone and in combination with other cholesterol-reducing agents in an amount effective to reduce hypercholesteremia in the mammal. Also provided are methods of treating a cardiovascular disorder associated with atherosclerosis in a mammalian subject comprising administering to the subject a layered phyllosilicate material in an amount effective to reduce atherosclerotic lesion formation in the subject.

28 Claims, 17 Drawing Sheets

(56) References Cited

OTHER PUBLICATIONS

Malinow et al., "Effect of alfalfa saponins on intestinal cholesterol absorption in rats," *Am. J. Clin. Nutr.* 30:2061-2067 (1977).

Najda et al., "The Effect of Silicon (Si) on Lipid Parameters in Blood Serum and Arterial Wall," *Bio. Trace Element Res.*, 31:235-247 (1991).

Nielsen et al., "Effect of Lovastatin on Cholesterol Absorption in Cholesterol-Fed Rabbits," *Pharmacol. Toxicol.*, 72(3):148-151 (1993).

Nikkila et al., "Effect of Treatment With Bentonite on Serum Protein, Lipid Phosphorus, and Cholesterol," *Ann. Med. Exp. Biol. Fenn.*, 30:51-58 (1952).

Nishide et al., "Effects of alginates on the ingestion and excretion of cholesterol in the rat," *J. Appl. Phycology*, 5:207-211 (1993).

Osol, "Remington's Pharmaceutical Sciences 16th Edition," *A. Ed.* (1980).

Peluso et al., "A Food-Grade Silicon Dioxide is Hypocholesterolemic in the Diet of Cholesterol-Fed Rats," *J. Nutr.*, 124:853-860 (1994).

Physician's Desk Reference 57:1101-1105. (2003).
Physician's Desk Reference 57:2036-2041. (2003).
Physician's Desk Reference 57:2126-2131. (2003).
Physician's Desk Reference 57:2283-2287. (2003).
Physician's Desk Reference 57:2547-2551. (2003).
Physician's Desk Reference 57:2610-2613. (2003).

Prior et al., "The Hypercholesteremic Rabbit," *Archives of Pathology*, 71:82-94 (1961).

Sagesaka-Mitane et al., "Platelet Aggregation Inhibitors in Hot Water Extract of Green Tea," *Chem. Pharm. Bull,*, 38:790-3, (1990).

Stensvold, et al., "Tea Consumption, Relationship to Cholesterol, Blood Pressure, and Coronary and Total Mortality," *Prev. Med.*, 21:546-53 (1992).

Tsubono et al., "Green Tea Intake in Relation to Serum Lipid Levels in Middle-Aged Japanese Men and Women," *Ann Epidemiol,*, 7:280-4 (1997).

Verd et al., "Different effect of simvastatin and atorvastatin on key enzymes involved in VLDL synthesis and catabolism in high fat/cholesterol fed rabbits," *Br. J. Pharmacology*, 127:1479-1485 (1999).

Wang et al., "Lack of the intestinal Muc1 mucin impairs cholesterol uptake and absorption but not fatty acid uptake in *Muc1-/-*mice," *Am. J. Physiol Gastrointest. Liver Physiol.*, 287(3):G547-54 (2004).

Wang, "Regulation of Intestinal Cholesterol Absorption," *Annu. Rev. Physiol.*, 69:221-48 (2007).

Wasan et al., "Assessing Plasma Pharmacokinetics of Cholesterol Following Oral Coadministration with a Novel Vegetable Stanol Mixture to Fasting Rats," *J. Pharmaceut. Sci.*, 90:23-28 (2001).

Wojciech, Pociecha, et al.; "Influence of the Mucoprotective Drugs on the Clinical Course of Children's Rotaviral Gastroenteritis," *Gastroenterologia Polska*, vol. 5 (6), pp. 533-542 (1998).

Written Opinion for PCT/US08/064351, from the European Patent Office as the International Searching Authority, dated Jan. 30, 2009.

Yamaguchi et al., "Folia Pharmacologica Japonica," *Nip .Yak. Zas.*, 97:329-37 (1991).

Habold et al., "Clay ingestion enhances intestinal triacylglycerol hydrolysis and non-esterified fatty acid absorption," *British Journal of Nutrition*, pp. 1-9 (2009).

International Preliminary Report on Patentability from PCT/US09/35484, dated Sep. 28, 2010.

\* cited by examiner

METHODS OF TREATING CARDIOVASCULAR DISORDERS ASSOCIATED WITH ATHEROSCLEROSIS

CROSS-REFERENCE TO RELATED APPLICATIONS

The present application is a continuation-in-part of U.S. patent application Ser. No. 12/124,748, filed May 21, 2008, which claims the benefit of priority of U.S. Provisional Application No. 60/966,557, filed May 23, 2007 and of U.S. Provisional Application No. 60/031,931, filed Feb. 27, 2008. The disclosure of each priority application is incorporated herein by reference in their entirety.

FIELD

This invention relates generally to methods and compositions for reducing hypercholesteremia in a mammalian subject. Methods of treating one or more cardiovascular disorders associated with atherosclerosis in mammalian subject are also provided.

BACKGROUND

According to recent information from the American Heart Association, an estimated 100,870,000 American adults have total cholesterol levels in the borderline-high risk range of 200 mg/dl to 239 mg/dl. There are 40,600,000 American adults living with high-risk cholesterol levels of 240 mg/dl or more. There are many risk factors that can indicate a propensity to have high levels of cholesterol, such as age, weight, health conditions such as diabetes, smoking, gender, race and ethnicity. Elevated blood cholesterol levels are associated with potentially deadly conditions of the heart and blood vessels, such as atherosclerosis, coronary artery insufficiency and stroke.

Atherosclerosis is the most common cause of death and serious morbidity in the Western world. Atherosclerosis is one of three morphologically distinct forms of arteriosclerosis. Arteriosclerosis is the hardening of the arteries due to their thickening and loss of elasticity. Atherosclerosis occurs when irregularly distributed lipid deposits form in the inner coating of the vessels of the elastic arteries, such as the aorta, carotid and iliac, or the large and medium-sized muscular arteries, such as the coronary and popliteal. These lipid deposits, called atheromatous plaques, cause fibrosis and calcification which leads to coronary heart disease and myocardial infarction. The plaques are comprised of cells, macrophages and other leukocytes, a connective tissue extra-cellular matrix and intracellular and extracellular lipid deposits. The progression of atherosclerosis can be slowed by reducing the plasma cholesterol and cholesterol LDL levels.

Hypercholesterolemia, or elevated blood cholesterol levels due to concentration of cholesterol in the cells and plasma, is also prevalent in the American population. Elevated total and LDL cholesterol levels are considered cardiovascular risk factors for coronary heart disease and myocardial infarction.

Cholesterol is the most abundant steroid in cell membranes and is essential to the growth and viability of cells. Cholesterol, free and in esterified form, is classified as a lipid and it is a component of lipoproteins, which are complexes of lipids (phospholipids and triglycerides) with proteins. There are four major categories of lipoproteins: chylomicrons, very low density lipoproteins (VLDL), low density lipoproteins (LDL), and high density lipoproteins (HDL). Chylomicrons transport some dietary cholesterol and mostly triglycerides from the intestines to the adipose tissue (also known as fat) and the liver. VLDLs transport cholesterol and triglycerides made by the liver to adipose and other tissues. LDL is a byproduct consisting of apolipoprotein and cholesterol that remains after the fat cells have removed the triglycerides from the VLDL. LDLs transport cholesterol to the peripheral tissues (cells outside the liver and intestine) and regulate the endogenous cholesterol levels therein. LDL is often referred to as the "bad cholesterol" because high levels increase the risk of developing arteriosclerosis and hypercholesterolemia. HDL, known as the "good cholesterol," transports cholesterol from the peripheral tissues (and arterial walls) to the liver. HDLs operate as good cholesterol because they have an opposite function to than of LDLs. It is thought that high levels of HDL can reverse the negative effects of LDL activity. The primary site of cholesterol synthesis is in the liver, although some cholesterol is synthesized in the intestines. The liver's function in this pathway is to remove the cholesterol from the blood. Plasma LDL is the primary source of cholesterol in peripheral tissues, which do not synthesize cholesterol de novo. LDL is taken into these cells via endocytosis at LDL receptor cites. The molecular genetics and cellular biology of the LDL receptor has been characterized by Goldstein and Brown (Atheroscler Suppl. 2004 October; 5(3):57-9). The LDL receptor is essential to cholesterol metabolism. When cholesterol is abundant inside the cell, there is no synthesis of LDL receptors, and thus cholesterol uptake from plasma cholesterol is blocked. The absence of the LDL receptor leads to hypercholesterolemia and atherosclerosis.

Typically, the average person consumes between 350-400 mg of cholesterol daily, while the recommended intake is around 300 milligrams. Increased dietary cholesterol consumption, especially in conjunction with a diet high in saturated fat intake, can result in elevated serum cholesterol. Having an elevated serum cholesterol level is a well-established risk factor for heart disease and therefore there is a need to mitigate the undesired effects of cholesterol accumulation. High cholesterol levels are generally considered to be those total cholesterol levels at 200 milligrams and above or LDL cholesterol levels at 130 milligrams and above. By lowering the total system LDL cholesterol level, it is believed that certain health risks, such as coronary disease and possibly some cancers, that are typically associated with high cholesterol levels, can be reduced by not an insignificant amount.

Numerous studies relating to modifying the intestinal metabolism of lipids illustrate that such effects can reduce a high cholesterol level (Burnett et al., Expert Opin Investig Drugs., 5(11):1337-51, 2006; Wang et al., Am J Physiol Gastrointest Liver Physiol., 287(3):G547-54, 2004; Heidrich et al., BMC Pharmacology, 4:5, 2004; Borel et al., Am. J. Clin. Nutr., 49:1192-1202, 1989; Malinow et al., Am. J. Clin. Nutr., 30:2061-2067, 1977). Hampering the absorption of triglycerides, cholesterol or bile acids or a combination of these mechanisms results in a lowering of cholesterol levels in the serum (Lewis et al., Journal of Lipid Research, 36:1098-1105, 1995).

Pharmaceuticals exist to treat elevated cholesterol levels but the majority cause significant side-effects, such as liver problems. For example, patients with hypercholesterolemia are usually started on one of three lipid-lowering therapeutic agents: (1) bile acid-binding resins, (2) niacin; or (3) 3-hydroxy-3-methylglutaryl-coenzyme A (HMG-CoA) reductase inhibitors. These drugs cause respectively: (1) constipation, gastric discomfort, nausea, hemorrhoidal bleeding; (2) arrhythmias, peptic ulcer disease, glucose intolerance, hepatic dysfunction; and (3) abnormal liver function and myositis. If these agents, normally prescribed as the first line of therapy are not successful, fibric acid derivatives like gemfibrozil are often administered. There are also side-effects with this class of drugs, such as lithogenicity of bile, nausea, abnormal liver functions and myositis.

The dietary consumption of clay, including montmorillonite, in animals and humans is known in the art (Carretero, App. Clay Sci., 21:155-163, 2002). There are ancillary reports of montmorillonite being effective as a cholesterol-lowering aid. However, although there are limited reports on the adsorption of cholesterol to a layered phyllosilicate material in vitro (Nikkila et al., Ann. Med. Exp. Biol. Fenn., 30:51-58, 1952), and on a hypocholesterolemic effect of a food-grade silicon dioxide in rats (Peluso et al., J. Nutr., 124:853-860, 1994), there are no specific reports of the effect of layered phyllosilicate materials on intestinal absorption in animals and/or humans or their effect on atherosclerotic lesions.

Of interest is International Patent Publication No. WO 2007/038596, which discloses phytosterol nutritional supplements that comprise bentonite. Bentonite and other silicate excipients are disclosed in this publication as conventional suspending/thickening agents for the manufacture of tablets, capsules and suspensions of phytosterols. This publication does not disclose or suggest the dietary cholesterol-lowering activity of these excipients.

Despite the large number of drugs available in various pharmacological categories, there is still a need in the art for new and effective treatments of hypercholesteremia and cardiovascular diseases associated with atherosclerosis.

SUMMARY OF THE INVENTION

The present invention includes materials (molecules, compositions, kits, unit doses, etc.) and methods for therapeutic or prophylactic treatment of cardiovascular disorders, and for diagnosing, evaluating, or monitoring such disorders. Similarly, the invention includes therapeutic and prophylactic uses of materials, including uses for the manufacture of medicaments for cardiovascular disorders.

In some aspects, the invention includes methods and compositions for the treatment of a cardiovascular disorder associated with atherosclerosis in a mammalian subject comprising administering a layered phyllosilicate material to the subject in an amount effective to reduce atherosclerotic lesion formation in the subject. Exemplary cardiovascular disorders include, but are not limited to, atherosclerosis, coronary heart disease, cerebral artery disease, peripheral artery disease, myocardial infarction, stroke, plaque rupture, plaque erosion, acute coronary syndrome, transient ischemia attack, angina, unstable angina, thrombosis, ischemic heart disease, coronary artery disease, and transplantation-induced sclerosis.

In other aspects, methods of reducing hypercholesteremia in a mammal are provided that comprise administering a layered phyllosilicate material to a mammal, wherein the layered phyllosilicate material comprises a layered phyllosilicate material (including, but not limited to, a hydrogen protonated layered phyllosilicate material), in an amount effective to reduce hypercholesteremia. In another embodiment, the method further comprises the step of administering a therapeutic agent (in addition to the layered phyllosilicate material) to the mammal in need of treatment. In one aspect, the therapeutic agent is a cholesterol-reducing agent. In another aspect, the therapeutic agent is a triglyceride-reducing agent. In certain variations, the layered phyllosilicate material is administered concurrently with the therapeutic agent. In other variations, the layered phyllosilicate material is administered at different times than the therapeutic agent.

In a preferred embodiment, the mammalian subject is a human subject. Practice of methods of the invention in other mammalian subjects, especially mammals that are conventionally used as models for demonstrating therapeutic efficacy in humans (e.g., primate, porcine, canine, or rabbit animals), is also contemplated. In one aspect, the subject is a human suffering from atherosclerosis. In another aspect, the subject is a human resistant to standard of care cholesterol lowering therapy.

Also provided are methods of delivering a therapeutic agent to a mammal comprising administering a composition comprising a layered phyllosilicate material, wherein the layered phyllosilicate material comprises a layered phyllosilicate material (including, but not limited to, a hydrogen protonated layered phyllosilicate material), and a therapeutic agent to the mammal, wherein the therapeutic agent is a lipid-lowering therapeutic agent or a cholesterol-reducing therapeutic agent. Contemplated therapeutic agents are described herein and include, but are not limited to, a nucleic acid, a protein, a polysaccharide, a drug and a small molecule drug. In certain variations, the therapeutic agent is intercalated within the layered phyllosilicate material.

In some embodiments, the methods described herein further comprise the step of administering a standard of care therapeutic to the subject in need of treatment. In the context of methods of the invention, "standard of care" refers to a treatment that is generally accepted by clinicians for a certain type of patient diagnosed with a type of illness. For cardiac disorders, for example, an aspect of the invention is to improve standard of care therapy with co-therapy with layered phyllosilicate materials described herein. In some embodiments, the standard of care therapeutic comprises a cholesterol-reducing agent selected from the group consisting of a statin-related agent (including, but not limited to, lovastatin, atorvastatin, pravastatin, simvastatin and fluvastatin), nicotinic acid, a fibrate (including, but not limited to, bezafibrate, ciprofibrate, clofibrate, gemfibrozil and fenofibrate), bile acid resin(s) (including, but not limited to, cholestyramine, colestipol and cholsevelam), a cholesterol absorption inhibitor (including, but not limited to, ezetimibe), salicylic acid, a phytosterol (including, but not limited to, stigmastanol, sitosterol, sitostanol and policosanol), an alginate or a pectin, lecithin and a nutraceutical associated with cholesterol reduction (including, but not limited to, epigallocatechin gallate (EGCG), Cholest-Arrest™, Cholestaway™, CholestOff™ and Kyolic™). In some embodiments, the therapeutic agent is a triglyceride reducing agent. In certain variations, the layered phyllosilicate material is administered concurrently with the standard of care therapeutic. In other variations, the layered phyllosilicate material and the standard of care therapeutic are administered at different times (i.e., sequentially).

Another aspect of the invention provides a method of treating a cardiovascular disorder associated with atherosclerosis in a mammalian subject comprising administering to the subject a layered phyllosilicate material in an amount effective to reduce atherosclerotic formation in the subject, wherein the subject is resistant to standard of care cholesterol-reducing therapeutic. Exemplary standard of care cholesterol-reducing therapeutics include, but are not limited to, a statin-related agent, nicotinic acid, a fibrate, bile acid resins, a cholesterol absorption inhibitor, salicylic acid, a phytosterol, an alginate or a pectin, lecithin and a nutraceutical associated with cholesterol reduction.

In another aspect, the invention provides a method of prophylactic treatment of a mammalian subject at risk for developing a cardiovascular disorder associated with atherosclerosis, comprising administering to the subject a layered phyllosilicate material in an amount effective to reduce the accumulation of atherosclerotic lesions in the subject.

In yet another aspect, the invention provides a method of treating a cardiovascular disorder associated with atherosclerosis in a mammalian subject in which treatment with a standard of care therapeutic described herein is contraindicated, wherein the method comprises administering to the subject a layered phyllosilicate material in an amount effective to reduce atherosclerotic lesion formation in the subject.

The layered phyllosilicate material useful in the methods described herein include the following clay minerals: montmorillonite, particularly sodium montmorillonite, protonated hydrogen montmorillonite, magnesium montmorillonite and/or calcium montmorillonite; nontronite; beidellite; laponite; yakhontovite; zincsilite; volkonskoite; hectorite; saponite; ferrosaponite; sauconite; swinefordite; pimelite; sobockite; stevensite; svinfordite; vermiculite; synthetic clays; mixed layered illite/smectite minerals, such as rectorite, tarosovite, and ledikite; admixtures of illites with the clay minerals named above, and the magnesium aluminum silicates. Any one or any mixture of two or more of the above clay minerals is capable of adsorbing, and/or ionically bonding, or interacting in some manner to reduce adsorption of cholesterol. In one aspect, the layered phyllosilicate material is a smectite clay selected from the group consisting of bentonite, montmorillonite, nontronite, beidellite, laponite, hectorite and saponite.

In some embodiments, the layered phyllosilicate material comprises a smectite clay having at least 80% interlayer exchangeable homoionic cations, preferably hydrogen ions, based on the total of number of interlayer, exchangeable cations. In other embodiments, the layered phyllosilicate material comprises a smectite claim having at least 85%, at least 86%, at least 87%, at least 88%, at least 89%, at least 90%, at least 91% at least 92%, at least 93%, at least 94%, at least 95%, at least 96%, at least 97%, at least 98%, at least 99% or more interlayer, exchangeable homoionic cations based on the total number of interlayer, exchangeable cations. In one embodiment, the interlayer, exchangeable cations are hydrogen ions. Other contemplated layered phyllosilicate materials include protonated hydrogen ion-exchanged layered phyllosilicate materials; protonated onium ion-exchanged layered phyllosilicate materials (protonated organoclays); smectite clays having a particle size less than 74 µm, preferably less than 50 µm, more preferably less than 20 µm; and exfoliated smectite clays, including individual clay platelets and tactoids of 5 or less platelet layers.

In one embodiment, the layered phyllosilicate material can be ingested in the form of a powder or an aqueous and/or organic liquid solution or suspension which can further be filled into a capsule or compressed into a tablet for internal interaction with dietary cholesterol within the gastrointestinal tract that has been or is about to be ingested. The cholesterol remains sorbed on the clay and is prevented from being absorbed into the bloodstream.

Pharmaceutical compositions comprising the layered phyllosilicate material and a pharmaceutically acceptable carrier, diluent or adjuvant are also provided.

In another aspect, methods of reducing hypercholesteremia in a mammal are provided that comprise administering to said mammal a therapeutically-effective amount of a combination therapy comprising (a) a layered phyllosilicate material and (b) a standard of care therapeutic.

In some embodiments, the standard of care therapeutic comprises a cholesterol-reducing agent selected from the group consisting of a statin-related agent (including, but not limited to, lovastatin, atorvastatin, pravastatin, simvastatin and fluvastatin), nicotinic acid, a fibrate (including, but not limited to, bezafibrate, ciprofibrate, clofibrate, gemfibrozil and fenofibrate), bile acid resin(s) (including, but not limited to, cholestyramine, colestipol and cholsevelam), a cholesterol absorption inhibitor (including, but not limited to, ezetimibe), salicylic acid, a phytosterol (including, but not limited to, stigmastanol, sitosterol, sitostanol and policosanol), an alginate or a pectin, lecithin and a nutraceutical associated with cholesterol reduction (including, but not limited to, epigallocatechin gallate (EGCG), Cholest-Arrest™, Cholestaway™, CholestOff™ and Kyolic™). In some embodiments, the therapeutic agent is a triglyceride reducing agent. In certain variations, the layered phyllosilicate material is administered concurrently with the standard of care therapeutic. In other variations, the layered phyllosilicate material and the standard of care therapeutic are administered at different times (i.e., sequentially).

The foregoing summary is not intended to define every aspect of the invention, and additional aspects are described in other sections, such as the Detailed Description. The entire document is intended to be related as a unified disclosure, and it should be understood that all combinations of features described herein may be contemplated, even if the combination of features are not found together in the same sentence, or paragraph, or section of this document.

In addition to the foregoing, the invention can include, as an additional aspect, all embodiments of the invention narrower in scope in any way than the variations defined by specific paragraphs herein. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "a layered phyllosilicate material," is understood to represent one or more layered phyllosilicate materials. As such, the terms "a" (or "an"), "one or more," and "at least one" can be used interchangeably herein.

DETAILED DESCRIPTION OF THE INVENTION

Figure 1:
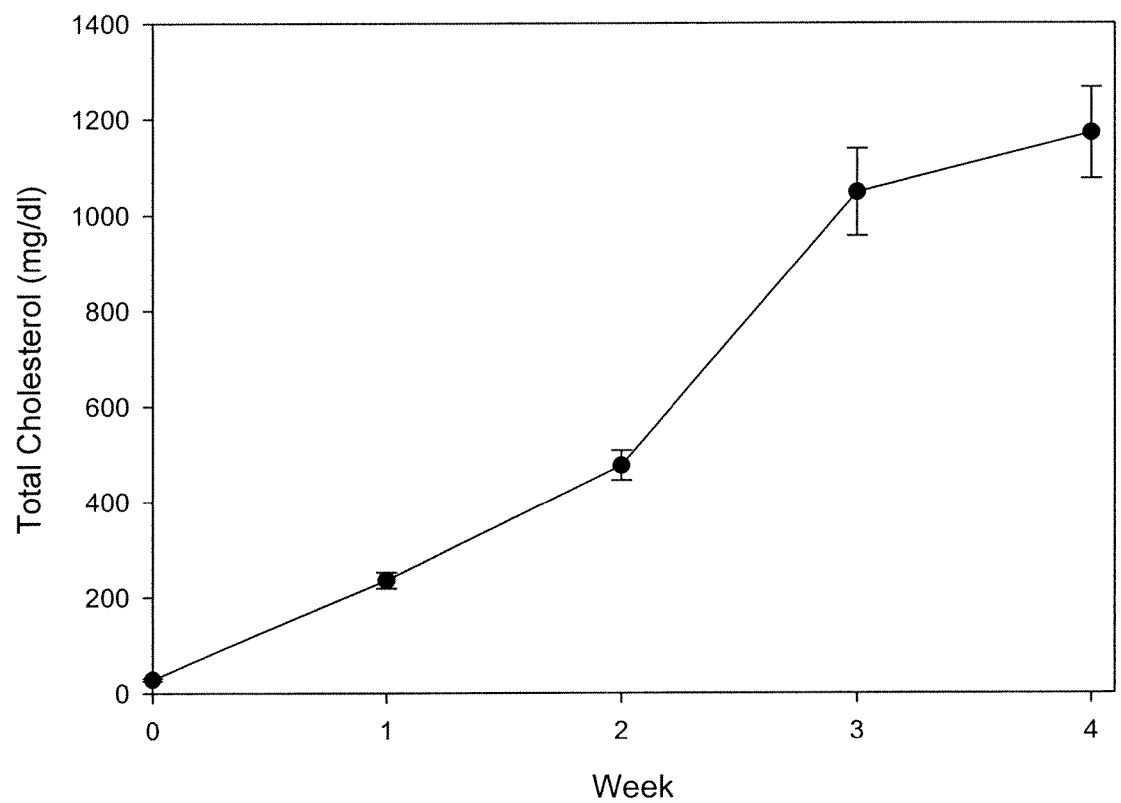
FIG. 1 shows the level of total plasma cholesterol of the subjects fed the high fat/cholesterol for four weeks prior to drug treatment.
Figure 2:
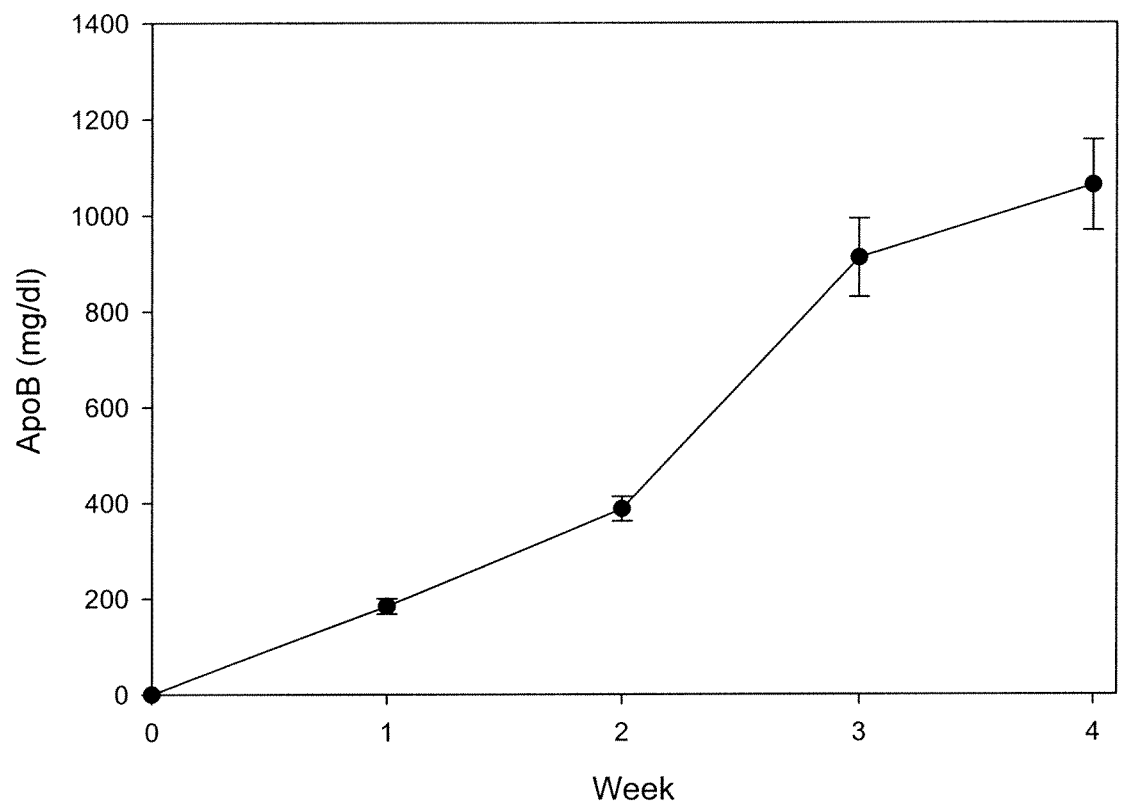
FIG. 2 shows the level of ApoB cholesterol of the subjects fed the high fat/cholesterol for four weeks prior to drug treatment.
Figure 3:
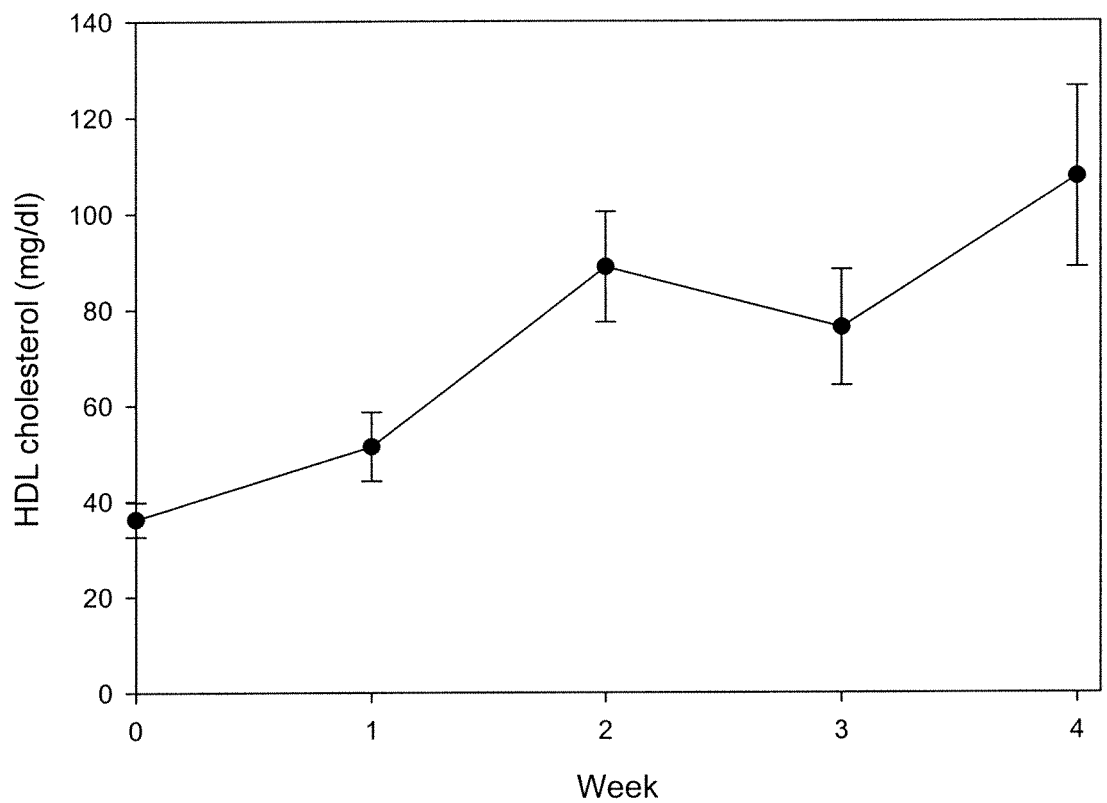
FIG. 3 shows the level of HDL cholesterol of the subjects fed the high fat/cholesterol for four weeks prior to drug treatment.
Figure 4:
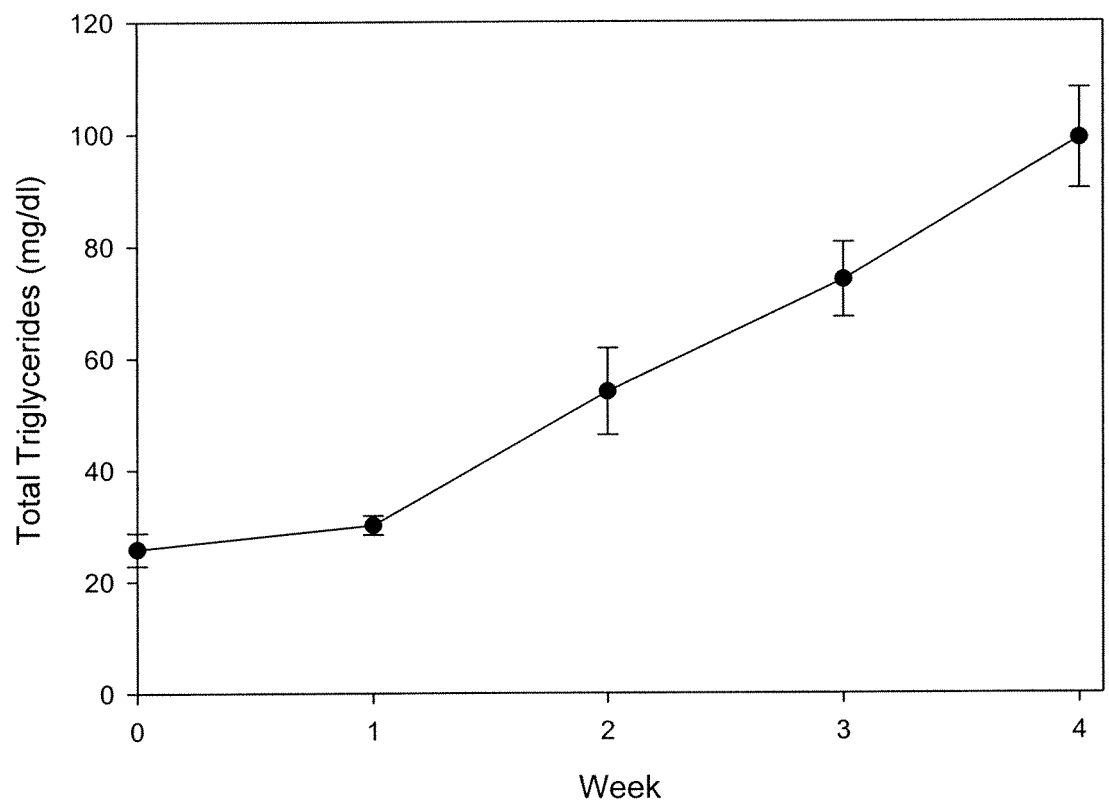
FIG. 4 shows the level of total plasma triglycerides of the subjects fed the high fat/cholesterol for four weeks prior to drug treatment.

One embodiment of the present invention is directed to the surprising discovery that administration of a layered phyllosilicate material described herein reduced atherosclerotic lesion formation in a mammalian subject afflicted with severe hypercholesteremia and atherosclerotic lesions that are similar in distribution and appearance to those observed in humans. Accordingly, the use of a layered phyllosilicate material (including but not limited to a hydrogen protonated layered phyllosilicate material) described herein as a therapeutic for treating cardiovascular disorders associated with atherosclerotic lesion formation is specifically contemplated.

Another embodiment of the present invention is directed to the discovery that administration of a layered phyllosilicate material described herein reduced total plasma cholesterol in a mammalian subject with severe dyslipidemia and therefore can be used as a therapeutic aid for reducing and/or altering cholesterol levels in mammals. The layered phyllosilicate material may optionally be formulated in a composition comprising a standard of care therapeutic that reduces atherosclerotic lesion formation (or cholesterol) in mammals by the same or different mechanism. The invention therefore describes various therapeutic compositions and methods for using the layered phyllosilicate material. One particular advantage of the layered phyllosilicate material of the present invention is the fact that due to their surface charge and molecular size, the phyllosilicate material cannot be taken up by cells or cross mucosal membranes and thus toxicity reactions seen with small molecule drugs can be avoided.

Whenever used in this specification, the terms set forth shall have the following meanings:

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

As used herein, the terms "sorption" or "sorb" refers to the action of either absorption or adsorption.

As used herein, the terms "therapeutically effective" or "amount sufficient" refers to when a composition or method of the invention is properly administered in vivo to a mammalian subject, including humans, a measurable beneficial effect occurs. Exemplary beneficial effects include a measurable reduction in atherosclerotic lesion formation in the mammalian subject; a measurable reduction in the level of cholesterol and/or LDL and/or triglycerides in the blood of the mammal; reduction of clinically verifiable and/or patient-reported level of high cholesterol and/or LDL and/or triglycerides or complete resolution or curing of the elevated LDL and/or cholesterol and/or triglyceride condition or other diseases. Normal and elevated levels of total cholesterol, LDL and triglycerides in blood are set forth in Table 1. Cholesterol levels can be measured by withdrawing blood from a patient and performing standard blood chemistry tests thereon.

TABLE 1

Normal and Elevated Levels of total Cholesterol, LDL and Triglyceride in Human Blood.

| Lipid Test | Normal (mg/dL) | Borderline High (mg/dL) | High (mg/dL) | Very High (mg/dL) |
|---|---|---|---|---|
| Total Cholesterol | <200 | 200-239 | >240 | |
| Low Density Lipoprotein (LDL) | <100 | 130-159 | 160-189 | >190 |
| Triglyceride | <150 | 150-199 | 200-499 | >500 |

The terms "hypercholesteremia" or "hypercholesterolemia" as used herein mean the presence of elevated levels of cholesterol in the blood of a mammal.

The term "atherosclerosis" as used herein means the progressive narrowing of the blood vessels and arteries over time through the accumulation of plaque inside blood vessels (including arterial vessels). Plaques are typically made up of cholesterol and other fats, calcium deposits, cells, and cell debris.

The term "atherosclerotic lesion" or "atherosclerotic plaque" as used herein means a deposit of fatty material along the walls of blood vessels and arteries. An atherosclerotic lesion begins as a fatty streak, an ill-defined yellow lesion-fatty plaque, which develops well-demarcated edges that evolve to fibrous plaques, whitish lesions with a grumous lipid-rich core which, with time, becomes a complicated plaque composed of white blood cells, smooth muscle cells and extracellular matrix in large artery intimas.

As used herein, the terms "concurrently" and "concurrent administration" mean that the layered phyllosilicate material and a therapeutic agent are administered to the subject either (a) simultaneously in time (optionally by formulating the two together in a common carrier), or (b) at different times during the course of a common treatment schedule. In the latter case, the two compounds are administered sufficiently close in time to achieve the intended effect.

The term "Phyllosilicate" or "layered phyllosilicate material" shall mean clay minerals, e.g., montmorillonite, particularly sodium montmorillonite, magnesium montmorillonite and/or calcium montmorillonite; protonated montmorillonite; nontronite; beidellite; laponite; yakhontovite; zincsilite; volkonskoite; hectorite; saponite; ferrosaponite; sauconite; swinefordite; pimelite; sobockite; stevensite; svinfordite; vermiculite; synthetic clays; mixed layered illite/smectite minerals, such as rectorite, tarosovite, and ledikite; admixtures of illites with the clay minerals named above, and the magnesium aluminum silicates.

"Homoionic Phyllosilicate" shall mean a layered Phyllosilicate material that has been purified by ion-exchange, for example, as described in this assignee's U.S. Pat. No. 6,050,509, to contain at least 90% of a single interlayer exchangeable cation, in relation to all interlayer exchangeable cations, from periodic table groups 1a, 2a, 3b, 4b, 5b, 6b, 7b, 8, 1b, 2b, 3a, tin and lead; or a protonated onium ion compound, as the interlayer exchangeable cations.

"Platelets" shall mean individual layers of a Phyllosilicate.

"Intercalate" or "Intercalated" shall mean a phyllosilicate material that includes an onium ion spacing agent, preferably a protonated onium ion spacing agent, disposed between adjacent platelets of the layered Phyllosilicate material to increase the interlayer spacing between the adjacent platelets by at least 3 Å, preferably at least 5 Å, to an interlayer spacing, for example, of at least about 8 Å, preferably at least about 10 Å.

"Intercalation" shall mean a process for forming an Intercalate.

"Onium Ion Intercalant" or "Onium Ion Spacing Agent" or "Onium Ion Compound" shall mean an organic compound, preferably a protonated organic compound, that includes at least one positively charged atom selected from the group consisting of a nitrogen atom, a phosphorous atom, a sulfur atom or an oxygen atom, preferably a quaternary ammonium compound, and when dissolved in water and/or an organic solvent, an anion dissociates from the onium ion spacing agent leaving an onium cation that can ion-exchange with a silicate platelet exchangeable cation of the Phyllosilicate, e.g., $Na^+$, $Ca^{+2}$, $Li^+$, $Mg^{+2}$, $Al^{+3}$, or $K^+$.

"Intercalating Carrier" shall mean a carrier comprising water and/or an organic liquid to form an Intercalating Composition capable of achieving Intercalation of an onium ion spacing agent which ion-exchanges with exchangeable interlayer cations of the layered Phyllosilicate.

"Tactoid" shall mean a stack of individual clay platelet layers having ten or fewer platelets, preferably five or fewer platelets that result from partial exfoliation of a layered phyllosilicate material.

"Intercalating Composition" shall mean a composition comprising one or more onium ion spacing agents, an Intercalating Carrier for the onium ion spacing agent, and a layered Phyllosilicate.

"Exfoliate" or "Exfoliated" shall mean individual platelets of an Intercalated layered Phyllosilicate so that adjacent platelets of the Intercalated layered Phyllosilicate can be dispersed individually throughout a carrier material, such as water, a polymer, an alcohol or glycol, or any other organic liquid, together with or without tactoids of 2-20 layers of non-exfoliated or partially exfoliated platelets.

"Exfoliation" shall mean a process for forming an Exfoliate from an Intercalate.

I. Layered Phyllosilicate Material for Use in the Methods Described Herein

A. Clay Purification and Ion-Exchange

A preferred layered phyllosilicate material useful for interaction with cholesterol comprises a smectite clay having, as a starting material, sodium or calcium ions as its predominant interlayer exchangeable cation, and that has been purified and ion-exchanged in accordance with this assignee's U.S. Pat. No. 6,050,509, hereby incorporated by reference. The ion-exchange process can be used to provide a homoionic layered phyllosilicate material or can be used to provide the phyllosilicate with mixed cations from the periodic table groups 1a, 1b, 2a, 2b, 3a, 3b, 4b, 5b, 6b, 7b, 8, tin, hydrogen, lead, and/or protonated onium ions, within any percentage of the phyllosilicate exchangeable cations (1-99% of the exchangeable cations). According to U.S. Pat. No. 6,050,509 the smectite clay slurry is pumped to a series of ion exchange columns where any undesirable cation is exchanged with a desirable cation. In this manner, the crude montmorillonite clay can be exchanged to produce a purified montmorillonite with a single (homoionic) desirable cation or with a mixture of cations. In this manner, by using the appropriate ion exchange column, any element can be exchanged for the interlayer cations of a phyllosilicate for cholesterol interaction, including hydrogen and/or one or more elements from the following groups of the periodic table: group 1a (e.g., lithium, sodium, potassium) group 2a (e.g., magnesium, calcium, barium) group 3b (e.g., lanthanium), group 4b (e.g., titanium) group 5b (e.g., vanadium), group 6b (e.g., chromium), group 7b (e.g., manganese) group 8 (e.g., iron, cobalt, nickel, platinum), group 1b (e.g., copper, gold, silver), group 2b (e.g., zinc, cadmium) group 3a (e.g., boron, aluminum) and selected members of group 4a (e.g., tin and lead). In this manner, one could exchange a metal or metal cation with known, good anti-cholesterol properties on the surface of the montmorillonite clay, or any layered phyllosilicate material, to produce a material with superior anti-cholesterol properties. Homoionic hydrogen ion-exchanged layered phyllosilicates are formed as follows: A purified sodium exchanged clay was dispersed into filtered DI water to make a 3 wt % clay slurry. The mixture was mixed thoroughly with a Silverson homogenizer. The pH value of the starting clay slurry was about 10. An ion exchange resin, Amberlite FPC23H available from Rohm & Hass, was packed into two glass columns with a 2-inch diameter and a 20-in length; one inch of space was left at the top of each column to promote flowability of the beads. The 3 wt % purified sodium exchanged clay slurry was continually mixed using a 3-inch dispersion blade while a liquid pump was used to pump the clay slurry through two resin packed columns at 20 ml/min. The pH of the clay slurry effluent was 2.3 after passing through the second column. Analytical results by ICP and X-Ray studies showed essentially complete exchange to the protonated form In accordance with this embodiment of the layered phyllosilicate, the crude layered phyllosilicate deposits initially include one or more of the following non-smectite impurities: ($SiO_2$), feldspar ($KAlSi_3O_8$), opal-CT ($SiO_2$); gypsum ($CaSO_4.2H_2O$); albite ($NaAlSi_3O_8$); anorthite ($CaAl_{12}Si_2O_8$); orthoclase ($KAlSi_3O_8$); apatite ($Ca_5(PO_4)_3$ (F,Cl,OH)); halite (NaCl); calcite ($CaCO_3$); dolomite ($CaMg(CO_3)_2$; sodium carbonate ($Na_2CO_3$); siderite ($FeCO_3$) biotite ($K(Mg,Fe)_3(AlSi_3O_{10})$ $(OH)_2$) muscovite ($KAl_2(AlSi_3O_{10})$ $(OH)_2$); chlorite ($(Mg,Fe)_6(Si,Al)_4O_{10}$ $(OH)_8$); stilbite ($NaCa_2Al_5Si_{13}O_{36}.14H_2O$); pyrite ($FeS_2$); kaolinite ($Al_2Si_2O_5.(OH)_4$); and hematite ($Fe_2O_3$).

In order to remove at least 90% by weight of the above impurities, preferably at least 99% of the impurities, preferably, the layered phyllosilicate is dispersed (slurried) in water, preferably at a concentration of about 10% to about 15% by weight, based on the total weight of phyllosilicate and water. The preferred layered phyllosilicate is a smectite clay, including but not limited to a montmorillonite clay, that is predominantly (greater than about 50% by weight) sodium or calcium (sodium or calcium ions outnumber any other cation in the interlayer spaces between adjacent clay platelets) montmorillonite clay so that the concentration of clay dispersed in water can be as high as about 15% by weight. If, for example, a sodium montmorillonite clay is dispersed in water, the higher swelling capacity of sodium montmorillonite in water will result in a viscosity that is too high for handling at a concentration of about 6-10% by weight. Accordingly, in order to achieve the most efficient purification of the smectite clay, it is preferred that the clay dispersed in water is a montmorillonite clay having predominantly (at least 50% by number) multivalent cations, i.e., $Ca^{+2}$ in the interlayer space, such as calcium montmorillonite clay. If the clay is not predominantly a multivalent clay, such as calcium montmorillonite, it can be ion-exchanged sufficiently to provide predominantly multivalent ions in the interlayer spaces between montmorillonite clay platelets.

The clay slurry is then directed into a series of cascaded hydrocyclones of decreasing size, each hydrocyclone capable of removing impurities of at least a particular size, particularly the impurities having a size greater than about 74 microns. The resulting clay, separated from the impurities, has a particle size such that at least about 90% by volume of the clay particles have a size below about 74 microns, preferably below about 50 microns, more preferably below about 20 microns. The clay slurry is then directed upwardly through a cation exchange column that removes multivalent interlayer cations from the montmorillonite clay (e.g., divalent and/or trivalent cations) and substitutes monovalent cations such as sodium, lithium and/or hydrogen for the multivalent cations within the interlayer spaces between platelets of the montmorillonite clay.

After essentially complete ion exchange, such that the clay has at least 90%, preferably at least 95%, more preferably at least 99%, by number, monovalent cations in the interlayer spaces, the clay preferably is then directed into a high speed centrifuge where the clay is subjected to centrifugal force equal to, for example, at least about 2,000 G (forces of gravity) up to about 4,000 G, preferably about 2,500 G to about 3,500 G, capable of removing clay particle sizes between about 5 microns and about 74 microns, such that the remaining montmorillonite clay particles, having less than about 50 by weight crystalline and amorphous non-smectite clay impurities, preferably less than about 5% by weight impurities therein, have a particle size of about 10 microns or less, preferably about 8 microns or less, and have an average particle size less than about 3 microns, preferably less than about 2 microns.

In accordance with an important feature of this embodiment, for effective removal of the impurities that have a size less than about 10 microns in diameter, the clay should first be conditioned or treated for removal of all multivalent, e.g., divalent and trivalent, interlayer cations by substitution of the multivalent cations with one or more monovalent cations, such as sodium ions, or protonated onium ions, in order to provide effective removal of the smallest impurities, for example, in a high speed (2,000-4,000 G) centrifuge. In accordance with another important feature of this embodiment, it has been found that conveying the clay slurry through the hydrocyclones prior to monovalent, e.g., sodium ion-exchange provides for a much more efficient process since the material fed to the hydrocyclones can be fed at a higher solids content without an undue increase in the viscosity of the material fed to the hydrocyclones. Accordingly, ion-exchange is accomplished after the clay slurry is passed through the hydrocyclones and before sending the partially purified clay slurry to a centrifuge for removal of the smallest impurities removed from the product.

The product from primary and secondary one inch hydrocyclones are fed by gravity to an ion-exchange feed tank where the clay/water slurry, including impurities, are maintained at a clay concentration of about 1-7% by weight, preferably about 3-7% by weight, based on the total weight of material in the ion-exchange feed tank. The clay slurry from the ion-exchange feed tank is pumped to a series of ion-exchange columns where the interlayer clay cations are exchanged with cations from periodic table groups 1a, 1b, 2a, 2b, 3a, 3b, 4b, 5b, 6b, 7b, 8, tin or lead, preferably sodium. Ion-exchange is achieved, for example, by contact with an ion-exchange resin, preferably PUROLITE C-100, obtained from The PUROLITE Company, a polystyrene cross linked with divinyl benzene, in spherical bead form, in the sodium ionic form, having an 8% by weight divinyl benzene content to produce a sodium exchanged clay. One can use Amberlite FPC23H available from Rohm & Hass to produce a protonated form.

The product from a secondary one inch hydrocyclone includes at least about 90% by number particles having a size less than about 50 microns, preferably less than about 20 microns, more preferably less than about 10 microns, a mean particle size less than about 10 microns, and a median particle size less than about 5 microns.

B. Exfoliated Clay to Form Clay Platelets and/or Tactoids

To form the preferred intercalated and exfoliated layered phyllosilicates described herein, the phyllosilicate material, e.g., sodium and/or calcium bentonite, or any sodium and/or calcium smectite clay, should be swelled or intercalated, in the preferred embodiment, by sorption of an onium ion spacing agent.

While the compositions and methods described herein are described by way of the preferred embodiment via expanding the interlaminar spacing between adjacent platelets of a layered phyllosilicate material by intercalating onium ions between the silicate platelets, the increased interlaminar spacing also can be achieved by intercalating one or more polymers, a silane coupling agent, or by an acidification technique, by substitution with hydrogen (ion-exchanging the interlayer cations with hydrogen by use of an acid or ion-exchange resin) as disclosed in the Deguchi U.S. Pat. No. 5,102,948, and in the Lan, et al. U.S. Pat. No. 5,853,886, both patents hereby incorporated by reference. In this clay exfoliation embodiment, the extremely small size of the individual platelets and clay tactoids should permit interaction of cholesterol.

Sorption of the onium ion spacing agent should be sufficient to achieve expansion of the interlayer spacing of adjacent platelets of the layered phyllosilicate material (when measured dry) by at least about 3 Å, preferably at least about 5 Å.

The onium ion spacing agent is introduced into the layered phyllosilicate galleries in the form of a solid or liquid composition (neat or aqueous, with or without an organic solvent, e.g., an aliphatic hydrocarbon, such as heptane to, if necessary, aid to dissolve the onium ion compound) having an onium ion spacing agent concentration sufficient to provide a concentration of about 5% to about 10% by weight phyllosilicate (90-95% water) and the onium ion compound is dissolved in the phyllosilicate slurry water, preferably at a molar ratio of onium ions to exchangeable interlayer cations of at least about 0.25:1, more preferably at least about 0.5:1, most preferably at least about 1:1. The onium ion-intercalated layered phyllosilicate then is separated from the water easily, since the phyllosilicate is now hydrophobic, and dried in an oven to less than about 15% water, preferably bone dry, before interaction with the cholesterol. The onium ion spacing agent compound can be added as a solid with the addition to the layered phyllosilicate material/onium ion compound blend of preferably at least about 20% water, more preferably at least about 30% water or more, based on the dry weight of layered material. Preferably about 30% to about 50% water, more preferably about 30% to about 40% water, based on the dry weight of the layered material, is included in the onium ion intercalating composition, so that less water is sorbed by the intercalate, thereby necessitating less drying energy after onium ion intercalation.

The onium ion spacing agent cations intercalated via ion-exchange into the interlayer spaces between adjacent layered material platelets are primary, secondary, tertiary or quaternary onium ions having the following preferred structure:

wherein X=N, P, S, or O; and
wherein $R_1$, $R_2$, $R_3$ and $R_4$ are H or organic moieties, such as linear or branched alkyl, aryl or aralkyl moieties having 1 to about 24 carbon atoms.

The more preferred protonated $C_6+$ onium ions are preferably quaternary ammonium ions having Formula 1, as follows:

Formula 1

wherein $R_1$ is a long chain alkyl moiety ranging from $C_6$ to $C_{24}$, straight or branched chain, including mixtures of long chain moieties, i.e., $C_6$, $C_8$, $C_{10}$, $C_{12}$, $C_{14}$, $C_{16}$, $C_{18}$, $C_{20}$, $C_{22}$ and $C_{24}$, alone or in any combination; and $R_2$, $R_3$ and $R_4$ are moieties, same or different, selected from the group consisting of H, alkyl, benzyl, substituted benzyl, e.g., straight or branched chain alkyl-substituted and halogen-substituted; ethoxylated or propoxylated alkyl; ethoxylated or propoxylated benzyl, e.g., 1-10 moles of ethoxylation or 1-10 moles of propoxylation. Preferred protonated onium ions include protonated octadecylamine, protonated hexyl amine; protonated octyl amine; protonated tallow amine; protonated tallow diamine; protonated tallow triamine; protonated tallow tetraamine; protonated hydrogenated tallow amine; protonated hydrogenated tallow diamine; protonated hydrogenated tallow triamine; protonated hydrogenated tallow tetraamine; protonated octadecyl amine; and mixtures thereof.

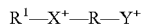

where $X^+$ and $Y^+$, same or different, are ammonium, sulfonium, phosphonium, or oxonium radicals such as $^+NH_3$, $^+NH_2$—, $^+N(CH_3)_3$, $^+N(CH_3)_2$—, $^+N(CH_3)_2(CH_2CH_3)$, $^+N(CH_3)(CH_2CH_3)$—, $^+S(CH_3)_3$, $^+S(CH_3)_2$—, $^+P(CH_3)_3$, $^+P(CH_3)_2$—, $^+NH_4$, $^+NH_3$—, and the like; R is an organic spacing, backbone radical, straight or branched, preferably having from 2 to 24, more preferably 3 to 10 carbon atoms, in a backbone organic spacing molecule covalently bonded at its ends to charged $N^+$, $P^+$, $S^+$ and/or $O^+$ cations and $R^1$ can be hydrogen, or an alkyl radical of 1 to 22 carbon atoms, linear or branched, preferably having at least 6 carbon atoms. Examples of R include substituted or unsubstituted alkylene, cycloalkenylene, cycloalkylene, arylene, alkylarylene, either unsubstituted or substituted with amino, alkylamino, dialkylamino, nitro, azido, alkenyl, alkoxy, cycloalkyl, cycloalkenyl, alkanoyl, alkylthio, alkyl, aryloxy, arylalkylamino, alkylamino, arylamino, dialkylamino, diarylamino, aryl, alkylsufinyl, aryloxy, alkylsulfinyl, alkylsulfonyl, arylthio, arylsulfinyl, alkoxycarbonyl, arylsulfonyl, or alkylsilane. Examples of R1 include non-existent; H; alkyl having 1 to 22 carbon atoms, straight chain or branched; cycloalkenyl; cycloalkyl; aryl; alkylaryl, either unsubstituted or substituted or substituted with amino, alkylamino, dialkylamino, nitro, azido, alkenyl, alkoxy, cycloalkyl, cycloalkenyl, alkanoyl, alkylthio, alkyl, aryloxy, arylalkylamino, alkylamino, arylamino, dialkylamino, diarylamino, aryl, alkylsufinyl, aryloxy, alkylsulfinyl, alkylsulfonyl, arylthio, arylsulfinyl, alkoxycarbonyl, arylsulfonyl, or alkylsilane. Illustrative of useful R groups are alkylenes, such as methylene, ethylene, octylene, nonylene, tert-butylene, neopentylene, isopropylene, sec-butylene, dodecylene and the like; alkenylenes such as 1-propenylene, 1-butenylene, 1-pentenylene, 1-hexenylene, 1-heptenylene, 1-octenylene and the like; cycloalkenylenes such as cyclohexenylene, cyclopentenylene and the like; alkanoylalkylenes such as butanoyl octadecylene, pentanoyl nonadecylene, octanoyl pentadecylene, ethanoyl undecylene, propanoyl hexadecylene and the like; alkylaminoalkylenes, such as methylamino octadecylene, ethylamino pentadecylene, butylamino nonadecylene and the like; dialkylaminoalkylene, such as dimethylamino octadecylene, methylethylamino nonadecylene and the like; arylaminoalkylenes such as phenylamino octadecylene, p-methylphenylamino nonadecylene and the like; diarylaminoalkylenes, such as diphenylamino pentadecylene, p-nitrophenyl-p-α-methylphenylamino octadecylene and the like; alkylarylaminoalkylenes, such as 2-phenyl-4-methylamino pentadecylene and the like; alkylsulfinylenes, alkylsulfonylenes, alkylthio, arylthio, arylsulfinylenes, and arylsulfonylenes such as butylthio octadecylene, neopentylthio pentadecylene, methylsulfinyl nonadecylene, benzylsulfinyl pentadecylene, phenylsulfinyl octadecylene, propylthiooctadecylene, octylthio pentadecylene, nonylsulfonyl nonadecylene, octylsulfonyl hexadecylene, methylthio nonadecylene, isopropylthio octadecylene, phenylsulfonyl pentadecylene, methylsulfonyl nonadecylene, nonylthio pentadecylene, phenylthio octadecylene, ethyltio nonadecylene, benzylthio undecylene, phenethylthio pentadecylene, sec-butylthio octadecylene, naphthylthio undecylene and the like; alkoxycarbonylalkylenes such as methoxycarbonylene, ethoxycarbonylene, butoxycarbonylene and the like; cycloalkylenes such as cyclohexylene, cyclopentylene, cyclo-octylene, cycloheptylene and the like; alkoxyalkylenes such as methoxy-methylene, ethoxymethylene, butoxymethylene, propoxyethylene, pentoxybutylene and the like; aryloxyalkylenes and aryloxyarylenes such as phenoxyphenylene, phenoxymethylene and the like; aryloryalkylenes such as phenoxydecylene, phenoxyoctylene and the like; arylalkylenes such as benzylene, phenthylene, 8-phenyloctylene, 10-phenyldecylene and the like; alkylarylenes such as 3-decylphenylene, 4-octylphenylene, 4-nonylphenylene and the like; and polypropylene glycol and polyethylene glycol substituents such as ethylene, propylene, butylene, phenylene, benzylene, tolylene, p-styrylene, p-phenylmethylene, octylene, dodecylene, octadecylene, methoxy-ethylene, moieties of the formula —$C_3H_6COO$—, —$C_5H_{10}COO$—, —$C_7H_{10}COO$—, —$C_7H_{14}COO$—, —$C_9H_{18}COO$—, —$C_{11}H_{22}COO$—, —$C_{13}H_{26}COO$—, —$C_{15}H_{30}COO$—, and —$C_{17}H_{34}COO$— and —$C=C(CH_3)COOCH_2CH_2$—, and the like. Such tetra-, tri-, and di-ammonium, -sulfonium, -phosphonium, -oxonium; ammonium/sulfonium; ammonium/phosphonium; ammonium/oxonium; phosphonium/oxonium; sulfonium/oxonium; and sulfonium/phosphonium radicals are well known in the art and can be derived from the corresponding amines, phosphines, alcohols or ethers, and sulfides.

Other useful spacing agent compounds are multi-onium ion compounds that include at least two primary, secondary, tertiary or quaternary ammonium, phosphonium, sulfonium, and/or oxonium ions having Formula 2, as follows:

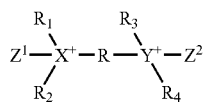

Formula 2 wherein R is an alkylene, aralkylene or substituted alkylene charged atom spacing moiety, preferably ranging from $C_3$ to $C_{24}$, more preferably about $C_3$ to $C_6$ for relatively high charge density (150 milliequivalents/100 grams C.E.C. to 70 milliequivalents/100 grams C.E.C.) layered materials; and preferably from $C_6$ to $C_{12}$ for medium to low charge density (70 milliequivalents/100 grams C.E.C. to 30 milliequivalents/100 grams C.E.C.) layered materials. R can be straight or branched chain, including mixtures of such moieties, i.e., $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$ and $C_{24}$, alone or in any combination; and $R_1$, $R_2$, $R_3$ and $R_4$ are moieties, same or different, selected from the group consisting of hydrogen, alkyl, aralkyl, benzyl, substituted benzyl, e.g., straight or branched chain alkyl-substituted and halogen-substituted; ethoxylated or propoxylated alkyl; ethoxylated or propoxylated benzyl, e.g., 1-10 moles of ethoxylation or 1-10 moles of propoxylation. $Z^1$ and $Z^2$, same or different, may be non-existent, or may be any of the moieties described for $R_1$, $R_2$, $R_3$ or $R_4$. Also, one or both of $Z^1$ and $Z^2$ may include one or more positively charged atoms or onium ion molecules.

Any swellable layered phyllosilicate material that sufficiently sorbs the onium ion spacing agent to increase the interlayer spacing between adjacent phyllosilicate platelets by at least about 3 Å, preferably at least about 5 Å, can be used in the practice of this invention. Useful swellable layered materials include phyllosilicates, such as smectite clay minerals, e.g., montmorillonite, particularly sodium montmorillonite, magnesium montmorillonite and/or calcium montmorillonite; nontronite; beidellite; laponite; yakhontovite; zincsilite; volkonskoite; hectorite; saponite; ferrosaponite; sauconite; swinefordite; pimelite; sobockite; stevensite; svinfordite; vermiculite; synthetic clays; mixed layered illite/smectite minerals, such as rectorite, tarosovite, and ledikite; admixtures of illites with the clay minerals named above, magnesium aluminum silicates; ion-exchanged phyllosilicates, including homoionic and/or protonated phyllosilicates; and mixtures of any two or more of the above-listed phyllosilicates. Exemplary mixtures include any of the above-listed phyllosilicates, wherein one of the above-listed phyllosilicates is present in amount ranging from about 1%-99% wt. and another phyllosilicate is present in an amount ranging from 99%-1% wt.; or wherein one of the above-listed phyllosilicates is present in amount greater than 50% wt and another phyllosilicate is present in an amount less than 50% wt; or wherein one of the above-listed phyllosilicates is present in amount of 50% wt and a second phyllosilicate is present in an amount of 50%; or wherein one of the above-listed phyllosilicates is present in amount of about 10% wt and another phyllosilicate is present in an amount of about 90%; or wherein one of the above-listed phyllosilicates is present in amount of about 20% wt and another phyllosilicate is present in an amount of about 80%; or wherein one of the above-listed phyllosilicates is present in amount of about 30% wt and another phyllosilicate is present in an amount of about 70% wt; or wherein one of the above-listed phyllosilicates is present in amount of about 40% wt and another phyllosilicate is present in an amount of about 60% wt. The weight percent indicated above is based on the weight of the clay mixture.

Preferred swellable layered materials are phyllosilicates of the 2:1 type having a negative charge on the layers ranging from about 0.15 to about 0.9 charges per formula unit and a commensurate number of exchangeable metal cations in the interlayer spaces. Most preferred layered materials are smectite clay minerals such as montmorillonite, nontronite, beidellite, volkonskoite, hectorite, saponite, sauconite, sobockite, stevensite, and svinfordite.

As used herein the "interlayer spacing" refers to the distance between the internal faces of the adjacent phyllosilicate layers as they are assembled in the layered material before any delamination (exfoliation) takes place. The preferred clay materials generally include interlayer cations such as $Na^+$, $Ca^{+2}$, $K^+$, $Mg^{+2}$, $Al^{+3+}$, $NH_4$ and the like, including mixtures thereof, and can be ion-exchanged to include other cations such as the elements from period table group 1a, 1b, 2a, 2b, 3a, 3b, 4b, 5b, 6b, 7b, 8, tin and lead.

The onium ions, may be introduced into (sorbed within) the interlayer spaces of the layered phyllosilicate in a number of ways. In a preferred method of intercalating the onium ions between adjacent platelets of the layered material, the phyllosilicate material is slurried in water, e.g., at 5-20% by weight layered phyllosilicate material and 80-95% by weight water, and the onium ion compound is dissolved in the water in which the phyllosilicate material is slurried. If necessary, the onium ion compound can be dissolved first in an organic solvent, e.g., propanol. The phyllosilicate material then is separated from the slurry water and dried suspending the individual silicate platelets and tactoids in a liquid carrier.

To achieve sufficient intercalation of the onium ions between adjacent platelets of the layered phyllosilicate, the phyllosilicate/onium ion intercalating composition preferably contains a molar ratio of onium ions to layered phyllosilicate of at least 0.25:1, more preferably at least 0.5:1 for the onium ions to exchange interlayer cations with the smectite clay, most preferably 1:1, based on the dry weight of the phyllosilicate, so that the resulting onium ion-intercalated phyllosilicate has interior platelet surfaces that are sufficiently hydrophobic and sufficiently spaced for exfoliation and suspension of the individual platelets and tactoids in a liquid carrier. The onium ion carrier (preferably water, with or without an organic solvent) can be added by first solubilizing or dispersing the onium ion compound in the carrier; or a dry onium ion compound and relatively dry layered phyllosilicate preferably containing at least about 4% by weight water) can be blended and the intercalating carrier added to the blend, or to the phyllosilicate prior to adding the dry onium ion. When intercalating the phyllosilicate with onium ions in slurry form, the amount of water can vary substantially, e.g., from about 4% by weight, preferably from a minimum of at least about 30% by weight water, with no upper limit to the amount of water in the intercalating composition (the phyllosilicate intercalate is easily separated from the intercalating composition due to its hydrophobicity after onium ion treatment).

Alternatively, the onium ion intercalating carrier, e.g., water, with or without an organic solvent, can be added directly to the phyllosilicate prior to adding the onium ion compound, either dry or in solution. Sorption of the onium ion compound molecules may be performed by exposing the phyllosilicate to a dry or liquid onium ion compound in the onium ion intercalating composition containing at least about 2% by weight, preferably at least about 5% by weight onium ion compound, more preferably at least about 10% onium ion compound, based on the dry weight of the layered phyllosilicate material.

In accordance with an emulsion method of intercalating the onium ions between the platelets of the layered phyllosilicate material, the phyllosilicate, preferably containing at least about 4% by weight water, more preferably about 10% to about 15% by weight water, is blended with water and/or organic solvent solution of an onium ion spacing agent compound in a ratio sufficient to provide at least about 5% by weight, preferably at least about 10% by weight onium ion compound, based on the dry weight of the layered phyllosilicate material.

The onium ion spacing agents have an affinity for the phyllosilicate so that they are sorbed between, and are ion-exchanged with the cations on the inner surfaces of the silicate platelets, in the interlayer spaces.

II. Therapeutic Uses for the Layered Phyllosilicate Material

In yet another embodiment, the invention provides various in vivo methods of using a layered phyllosilicate material described herein.

Certain aspects of the invention relate to methods of treating atherosclerosis or a cardiovascular disorder associated with atherosclerosis in a mammalian subject by administration of a layered phyllosilicate material described herein. If the layered phyllosilicate material is administered prior to clinical manifestation of the unwanted condition (e.g., cardiovascular disease, atherosclerosis, heart attack or stroke), the treatment is prophylactic, e.g., it reduces (totally or partially) the extent to which the condition develops. If the layered phyllosilicate material is administered after manifestation of the unwanted condition, the treatment is therapeutic (i.e., it is intended to diminish, ameliorate or maintain the existing unwanted condition or side effects therefrom). In preferred embodiments, the mammalian subject is a human.

Without being bound to any particular theory, the layered phyllosilicate material prevents synthesis and adsorption of cholesterol in or from the gastrointestinal tract, which results in a reduction of atherosclerotic lesions in the subject.

In some embodiments, the atherosclerotic lesions are associated with a condition such as plaque rupture, plaque erosion, acute coronary syndrome, stroke, transient ischemia attack, heart attack, angina, unstable angina, thrombosis, myocardial infarction, ischemic heart disease, coronary artery disease, peripheral artery disease, or transplantation-induced sclerosis. Thus, the terms "cardiovascular disorder associated with atherosclerosis" or "cardiovascular disorder associated with atherosclerotic lesion formation" includes references to any of the above conditions or diseases that are medically linked to atherosclerosis in that they are a consequence of atherosclerotic lesions. "Coronary artery disease" ("CAD") is a pathological state characterized by atherosclerotic involvement of the coronary arteries. CAD is initially mild and the minimal narrowing of the artery it produces does not impair coronary flow and thus does not lead to myocardial ischemia and is asymptomatic. Nonetheless, such plaques can suddenly erode or rupture and lead to acute coronary syndrome (ACS). As the lesions progress, they produce sufficient arterial obstruction such that ischemia occurs, at which time the disease may become symptomatic (e.g., angina pectoris and myocardial infarction). As used herein, CAD includes both symptomatic or asymptomatic disease. The same considerations relate to atherosclerotic involvement of the arterial vessels that supply the brain and the legs. Plaque erosion or rupture occurs most commonly in lesions that are relatively mild and do not yet impair blood flow. As a result, severe manifestation of atherosclerosis (e.g., heart attack, stroke, sudden death) can occur as presenting manifestations of the disease, without prior, less severe symptoms having developed.

In some embodiments of the methods described herein, the mammalian subject is afflicted with cardiovascular atherosclerosis, cerebrovascular atherosclerosis, peripheral vessel atherosclerosis, coronary heart atherosclerosis or a combination thereof. In other embodiments, the subject is afflicted with obesity, insulin resistance, diabetes, hypertension, hypercholesteremia, or a combination thereof.

In one embodiment, the invention provides a method of treating a cardiovascular disorder associated with atherosclerosis comprising administering to the subject a layered phyllosilicate material described herein in an amount effective to reduce atherosclerotic lesion formation in the subject.

In another embodiment, the invention provides a method of reducing atherosclerotic lesion formation in a mammalian subject comprising administering to the subject a layered phyllosilicate material described herein in an amount effective to reduce atherosclerotic lesion formation in the subject.

Mammals suffering from atherosclerosis are identified using techniques well known in the art (e.g., angiography, electrocardiography as well as physiological and metabolic tests). Individuals at risk of developing atherosclerosis are also treated using the methods described herein. Risk factors include increasing age, male sex, heredity, cigarette and tobacco smoke, high blood cholesterol levels, high blood pressure, physical inactivity, obesity, stress, and/or diabetes mellitus.

In other embodiments, a layered phyllosilicate material described herein is useful to treat hypercholesteremia in a mammal as well as for providing a delivery vehicle for therapeutic agents (including, but not limited to, cholesterol-lowering agents, triglyceride-lowering agents and other lipid-lowering agents).

In one aspect, the layered phyllosilicate material reduces dietary cholesterol by removing cholesterol from the gastrointestinal tract Without being bound to any particular theory, removal of cholesterol from the gastrointestinal tract using the layered phyllosilicate material described herein is by one or more mechanisms selected from the group consisting of absorption, adsorption, ionic complexing, electrostatic complexing, chelation, hydrogen bonding, ion-dipole, dipole/dipole, Van Der Waals forces, and any combination thereof. In one aspect, the layered phyllosilicate material interferes with the pancreatic lipase mechanism similar to that of the anti-obesity drug Orlistat (Xenical®). Orlistat reduces intestinal fat absorption by inhibiting pancreatic lipase. Another lipase inhibitor, called GT 389-255, is being developed by Peptimmune. GT-389-255 is a combination of an inhibitor and a polymer designed to bind the undigested triglycerides therefore allowing increased fat excretion without side effects such as oily stools that occur with Orlistat. In one aspect, the layered phyllosilicate material suppresses cholesterol adsorption by blocking the degradative process of cholesterol within the gastrointestinal tract resulting in decreased solubility of cholesterol during intestinal diffusion (Wang et al., Annu. Rev. Physiol., 69:221-48, 2007)

In another aspect, the layered phyllosilicate material increases the thickness of the unstirred water layer covering the mucosa of the small intestine, thereby reducing cholesterol diffusion.

In another aspect, the layered phyllosilicate material interferes with micelle formation of bile acids around the cholesterol present in the gastrointestinal tract. As a result, the cholesterol remains insoluble and is not transported to and therefore not absorbed by the unstirred water layer of the microvilli.

In another aspect, the layered phyllosilicate increases the viscosity of the intestinal contents and reduces cholesterol absorption efficiency (Carr et al., J. Nutr. 126: 1463-1469, 1996).

In yet another aspect, the layered phyllosilicate material interacts with micelles containing cholesterol and reduces the rate of cholesterol diffusion from a micelle to the mucosa of the small intestine. As a result, the amount of cholesterol absorbed is reduced.

In one embodiment, the invention includes a method of reducing hypercholesteremia in a mammal comprising administering to said mammal a layered phyllosilicate material as described herein in an amount effective to reduce the level of total plasma cholesterol in said mammal. In one aspect, the layered phyllosilicate material is formulated into a composition comprising a pharmaceutically acceptable carrier, diluent or excipient.

In one embodiment, the mammal is human. In other embodiments, the mammal is an animal. Exemplary animals include, but are not limited to, farm animals such as horses, cows, sheep, pigs, alpacas, llamas and goats; companion animals such as dogs and cats; exotic and/or zoo animals; laboratory animals including mice, rats, rabbits, guinea pigs and hamsters.

In one embodiment, a composition comprising the layered phyllosilicate material will further comprise a standard of care therapeutic for the treatment of hypercholesteremia and/or a cardiovascular disease associated with atherosclerosis. The standard of care therapeutic can be a small molecule or macromolecule such as peptide, protein or nucleic acid. In certain aspects, the standard of care therapeutic is selected from the group consisting of cholesterol absorption inhibitors (including, but not limited to, ezetimibe (ZETIA, EZETROL, EZEMIBE, Merck, Schering-Plough); lipase inhibitors, see e.g., U.S. Pat. No. 6,432,200 (including, but not limited to, Orlistat (Xenical®) and GT 389-255); bile-acid-binding resins, which interrupt the recycling of bile acids from the intestine to the liver (including, but not limited to, cholestyramine (QUESTRAN LIGHT, Bristol-Myers Squibb), and colestipol hydrochloride (COLESTID, Pharmacia & Upjohn Company); statins, which inhibit cholesterol synthesis by blocking HMGCoA—the key enzyme involved in cholesterol biosynthesis (including, but not limited to, lovastatin (MEVACOR, Merck & Co., Inc.), a natural product derived from a strain of *Aspergillus*, pravastatin (PRAVACHOL, Bristol-Myers Squibb Co.), and atorvastatin (LIPITOR, Warner Lambert) cerivastatin (BAYCOR (Bayer), fluvastatin (LESCOL (Sandoz)), and simvastatin (ZOCOR (Merck)); niacin, a water-soluble vitamin B-complex which diminishes production of very low density lipoprotein (VLDL) and is effective at lowering low density lipoprotein (LDL); fibrates, including, but not limited to, clofibrate (ATROMID-S, Wyeth-Ayerst Laboratories), and gemfibrozil (LOPID, Parke-Davis), lower serum triglycerides by reducing the VLDL fraction and may in some patient populations give rise to modest reductions of plasma cholesterol; estrogen replacement therapy, which lowers cholesterol levels in post-menopausal women; long chain alpha, omego-dicarboxylic acids have been reported to lower serum triglyceride and cholesterol (See, e.g., Bisgaier et al., 1998, J. Lipid Res. 39:17-30; WO 98/30530; U.S. Pat. No. 4,689,344; WO 99/00116; U.S. Pat. No. 5,756,344; 3,773,946; 4,689,344; 4,689,344; 4,689,344; and 3,930,024); other compounds including ethers (See, e.g., U.S. Pat. Nos. 4,711,896; 5,756,544; 6,506,799), phosphates of dolichol (U.S. Pat. No. 4,613,593), and azolidinedione derivatives (U.S. Pat. No. 4,287,200) are disclosed as lowering serum triglyceride and cholesterol levels.

In yet another embodiment, the layered phyllosilicate material is utilized as a delivery vehicle. In one variation, the layered phyllosilicate material is a delivery vehicle for nucleic acids and proteins. In another variation, the layered phyllosilicate material is a delivery vehicle for a therapeutic agent described herein. Binding of a therapeutic agent to a layered phyllosilicate material can improve its delivery and absorption through mucosal membranes, including the ocular, dermal, nasal and intestinal membranes. Drug release from the layered phyllosilicates can be induced by pH, ionic strength changes, and/or in response to temperature, ionic current or ultrasound. In one embodiment, the layered phyllosilicate material is the delivery vehicle.

In other embodiments, the layered phyllosilicate material is used in lieu of or in conjunction with other drug delivery vehicles known in the art in order to increase cell targeting membrane permeability and absorption. Exemplary drug delivery systems known in the art include, but are not limited to, those described in U.S. Pat. Nos. 6,838,528; 6,797,704; 6,730,334; 6,706,289; 6,482,439; 6,443,989; 6,383,478; 6,165,440; 5,780,044; 5,759,563; 5,565,215; and U.S. Patent Application Publication Nos. 2007/0059327; 2007/0053845; 2007/00036278; 2007/0031340; 2007/0026048; 2007/0003610; 2006/0193787; 2006/0188543; 2006/0149392; 2006/0105049; 2006/0057206; 2006/0034925; 2005/0266090; 2005/0260276; 2005/0249798; 2005/0249774; 2005/0220754; 2005/0209345; 2005/0058603; 2005/0152965; 2005/0089572; 2005/0058701, the disclosures of which are incorporated herein by reference in their entireties.

Routes of Administration and Dosage

The layered phyllosilicate material alone, or in combination with one or more standard of care therapeutics as described herein, is administered by any route that delivers an effective dosage to the desired site of action, with acceptable (preferably minimal) side-effects. Numerous routes of administration are known, including for example, oral, rectal, vaginal, transmucosal, buccal or intestinal administration; parenteral delivery, including intraperitoneal, intramuscular, subcutaneous, intramedullary injections, as well as intrathecal, cutaneous or intradermal injections; respiratory or inhalation, nasal, pulmonary and topical application, including ocular and transdermal applications.

When used in the above or other treatments, a "therapeutically effective amount" or an "effective amount" of a layered phyllosilicate material or a composition comprising a layered phyllosilicate material means a sufficient amount of the layered phyllosilicate material is provided to achieve a measurable beneficial effect, at a reasonable benefit/risk ratio applicable to any medical treatment. Exemplary beneficial effects include a measurable reduction in atherosclerotic lesion formation in the mammalian subject; a measurable reduction in the level of cholesterol and/or LDL and/or triglycerides in the blood of the mammal; reduction of clinically verifiable and/or patient-reported level of high cholesterol and/or LDL and/or triglycerides or complete resolution or curing of the elevated LDL and/or cholesterol and/or triglyceride condition or other diseases. Normal and elevated levels of total cholesterol, LDL and triglycerides in blood are set forth in Table 1. Cholesterol levels can be measured by withdrawing blood from a patient and performing standard blood chemistry tests thereon. It will be understood, however, that the total daily usage of the layered phyllosilicate material will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of a layered phyllosilicate material administered to a mammalian subject range from about 0.001 to about 200 mg/kg/day. If desired, the effective daily dose may be divided into multiple doses for purposes of administration; consequently, single dose compositions may contain such amounts or submultiples thereof to make up the daily dose. The dosage regimen of a phyllosilicate composition alone or in combination as described herein to be used in anti-cholesterol treatment will be determined by the attending physician considering various factors which modify the action of the phyllosilicate, e.g., the patient's age, sex, and diet, the severity of any infection, time of administration and other clinical factors.

Oral dosage forms include tablets, capsules, caplets, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, supra). Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material.

In addition to the layered phyllosilicate material alone, or in combination as described herein, tablets prepared for oral administration will generally contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of *theobroma*, glycerin, magnesium stearate, calcium stearate, and stearic acid. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the layered phyllosilicate material-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts (See, for e.g., Remington: The Science and Practice of Pharmacy, supra). Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Although the present compositions may be administered orally, other modes of administration are contemplated as well. Exemplary modes of administration include transmucosal (e.g., U.S. Pat. Nos. 5,288,498; 6,248,760; 6,355,248; 6,548,490, the disclosures of which are incorporated herein by reference in their entireties), transurethral (e.g., e.g., U.S. Pat. Nos. 5,919,474 and 5,925,629, the disclosures of which are incorporated herein by reference in their entireties), vaginal or perivaginal (e.g., U.S. Pat. Nos. 4,211,679; 5,491,171 and 6,576,250, the disclosures of which are incorporated herein by reference in their entireties) and intranasal or inhalation (e.g., U.S. Pat. Nos. 4,800,878; 5,112,804; 5,179,079; 6,017,963; 6,391,318 and 6,815,424, the disclosures of which are incorporated herein by reference in their entireties). One of skill in the art would be able to modify a composition comprising a layered phyllosilicate material alone or in combination as described herein to be used in any of the modes of administration described herein.

The compositions of this invention can be employed in mixture with conventional excipients, i.e., pharmaceutically acceptable organic or inorganic carrier substances suitable for topical application which do not deleteriously react with the acid or the alcohol in the composition. The compositions of the invention can also include diluents, fillers, salts, buffers, stabilizers, solubilizers, and other materials well known in the art (Remington's Pharmaceutical Sciences 16th edition, Osol, A. Ed. (1980).

The layered phyllosilicate material of the invention is administered in a concentration (w/v) ranging from about 0.1% to about 20%, or from about 1% to about 10%, or in a concentration of about 2%, about 3%, about 4%, about 5%, about 6%, about 7%, about 8%, about 9%, about 10%, about 11%, about 12%, about 13%, about 14%, about 15%, about 16%, about 17%, about 18%, about 19% or about 20%.

Combination Therapy

The invention further contemplates the administration of standard of care therapeutics which possess the capacity to reduce atherosclerotic lesion formation, and/or the level of cholesterol and/or LDL and/or triglycerides and/or other lipids in the blood of a mammal, and are considered useful in a composition in combination with the layered phyllosilicate material according to the present invention. In one embodiment, the layered phyllosilicate material and the standard of care therapeutic are administered simultaneously in a combined amount effective to produce the desired therapeutic outcome. This is achieved by administering a single composition or pharmacological formulation that includes all of the active agents, or by administering to the subject two distinct compositions or formulations, at the same time, wherein one composition includes the layered phyllosilicate material, and the second composition includes the standard of care therapeutic(s). The layered phyllosilicate material and other standard of care therapeutic(s) may or may not exhibit the same mechanism by which they reduce the levels of total cholesterol (i.e., hypercholesteremia) and/or other lipids and/or atherosclerotic lesion formation in a mammal.

Alternatively, the layered phyllosilicate material treatment may precede or follow therapy with another therapeutic agent by intervals ranging from minutes to weeks. In embodiments where two or more therapeutic compositions are administered separately, one would generally ensure that a significant period of time did not expire between the time of each delivery, such that the standard of care therapeutic and layered phyllosilicate material would still be able to exert an advantageously combined effect. In such instances, it is contemplated that one would administer one or more compositions within about 12-24 hours of each other, or about 6-12 hours of each other, or with a delay time of only about 12 hours. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

A. Statin-Related Agents

In one embodiment, the standard of care therapeutic in the combination therapy is a statin-related agent. The term "statin-related" refers to any statin drug that is presently on the market, or is modified from the presently marketed statin drugs, and has a therapeutic effect when combined with the layered phyllosilicate material described herein. As such it should be understood that analogs and variants of preexisting statins are contemplated to be useful herein. Such analogs or variants may be produced through rational drug design techniques known to those of skill in the art. In particular, statin drugs are known as HMGCoA reductase inhibitors. These drugs are presently in clinical use as drugs in the battle against high cholesterol and in the control of heart attacks, both recurrent and first heart attacks. These agents generally have few side effects, and help not only to lower overall cholesterol, LDL cholesterol and triglycerides, but also to increase HDL cholesterol. The use of other compounds in the combination therapy that interfere with the activity of HMGCoA reductase is considered as an aspect of the invention.

Statins are exemplified by lovastatin (CAS Registry No. 75330-75-5; also known as mevinolin or monacolin K), and analogs of this compound have been described in numerous publications and patents. Exemplary statin compositions that are commercially available include Lipitor™ (atorvastatin), Pravachol™ (pravastatin), Zocor™ (simvastatin), Mevacor™ (lovastatin), and Lescol™ (fluvastatin). Methods of preparing such compounds are well known to those of skill in the art (see e.g., U.S. Pat. Nos. 6,521,762; 4,420,491; 4,342,767; 4,319,039; 4,294,846; 4,444,784; 4,582,915 and 4,820,850). As described in the foregoing patents, statins are traditionally produced through fermentation using organisms from the *Aspergillus* genus, *Monascus* genus, *Pleurotus* genus, *Coniothyrium* genus and the like (see U.S. Pat. No. 6,521,762 for review of such fermentation procedures).

Moreover, formulations of statins as a pharmaceutical medicament have been described in e.g., the Physician's Desk Reference. For example, tablet formulations of Lipitor™ (atorvastatin calcium) are described at pages 2547-2551 (Parke-Davis, NJ.) and 2610-2613 (Pfizer, NY) of the Physician's Desk Reference($57^{th}$ Edition, 2003). These formulations are supplied as tablets of atorvastatin calcium containing 10 mg, 20 mg, 40 mg, 50 mg, and 80 mg atorvastatin. The tablets are administered in doses ranging from 10 mg/day to 80 mg/day. The compositions of Lipitor™ presently being used to lower cholesterol in humans may be used in the combined treatments of the present invention to produce a therapeutic amelioration of HADDS and related lipodystrophy.

Pravachol™ (pravastatin sodium; Bristol-Myers Squibb, NY), is another exemplary commercially available statin that may be used in the combined therapies of the present invention. Pravachol™ is supplied as a 10 mg, 20 mg, 40 mg, and 80 mg tablets. These tablets may be administered at a daily dose of ranging from 10 mg/day to 80 mg/day. In exemplary treatments for hypercholesterolemia, 40 mg/day are administered as a single daily dose, with or without food. However, it is generally appreciated that this dose may be increased or lowered depending on the level of renal and liver function of the patient being treated. The administration doses and treatment guidelines for Pravachol™ are discussed in further detail at pages 1101-1105 of the Physician's Desk Reference (57$^{th}$ Edition, 2003) and may be used to provide guidance for the use of statins in the methods of the present invention.

Zocor™ (simvastatin; Merck & Co., Inc., NJ), is another exemplary statin composition that may be used in combination with the layered phyllosilicate material of the present invention. Formulations of simvastatin are described at pages 2126-2131 of the Physician's Desk Reference (57$^{th}$ Edition, 2003). The daily doses may range from 5 mg/day to 80 mg/day and those of skill in the art are referred to the Physician's Desk Reference for further guidance regarding treatment protocols that may be used and/or modified for the present invention.

Mevacor™ (lovastatin; Merck & Co., Inc. NY), and Lescol™ (fluvastatin) are other exemplary statins that are described in the Physician's Desk Reference (57$^{th}$ Edition, 2003) at pages 2036-2041 and 2283-2287, respectively. Those of skill in the art will readily be able to modify the above-referenced pharmaceutical compositions that comprise various statin-related agents for the methods of the present invention.

For treatment protocols, those of skill may use the guidelines used for the any of the above-referenced pharmaceutical statins. Administration of ordinary tablets containing statin once, twice, three or more times a day. Accordingly, the skilled artisan may use dosages that have previously proven effective for the above indications as a preliminary measure of the amount of any of the above-referenced statins, to use in the therapeutic methods of the invention.

Oral doses of the statins are particularly contemplated. Such oral doses may comprise the administration of between about 5 mg to about 80 mg statin drug on a daily basis. However, larger doses e.g., up to 200 mg/day also may be used. Thus, the subject may receive 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg or more statin drug orally. Of course it should be understood the subject may receive more or less of the statin. Also it should be understood that similar doses may be administered through other routine routes of administration. The statin may be delivered in a single dose or alternatively may be subdivided and administered in multiple doses over a given period of time.

B. Nicotinic Acid

In another embodiment, the standard of care therapeutic in the combination therapy is nicotinic acid. Nicotinic acid (niacin) lowers total and LDL cholesterol and raises HDL cholesterol, and also lowers triglycerides. The dose of niacin required to lower cholesterol is about 100 times more than the Recommended Daily Allowance (RDA) for niacin and thus can potentially be toxic. Therefore, the drug must be taken under a doctor's care.

C. Fibrates

In yet another embodiment, the standard of care therapeutic in the combination therapy is a fibrate. Fibric acid derivatives (fibrates) are a class of medications that lower blood triglyceride levels. Fibrates lower blood triglyceride levels by reducing the liver's production of VLDL and by speeding up the removal of triglycerides from the blood. Fibrates are also modestly effective in increasing blood HDL cholesterol levels; however, fibrates are not effective in lowering LDL cholesterol. Exemplary fibrates include, but are not limited to, Bezafibrate (e.g. Bezalip®), Ciprofibrate (e.g. Modalim®), Clofibrate, Gemfibrozil (e.g. Lopid®) and Fenofibrate (e.g. TriCor®).

D. Bile Acid Resins

In still another embodiment, the standard of care therapeutic in the combination therapy is a bile acid resin. Bile acid resins, also known as bile acid sequesterants, are mainly used to treat patients with moderately elevated LDL-cholesterol and when cholesterol-lowering drug therapy is necessary in young adult men and premenopausal women. They are also sometimes combined with other cholesterol-lowering drugs like "statins" to decrease very high levels of cholesterol. Exemplary bile acid resins include, but are not limited to, Cholestyramine, Colestipol (Colestid), and Cholsevelam (Welchol).

E. Cholesterol Absorption Inhibitors

In yet another embodiment, the standard of care therapeutic in the combination therapy is a cholesterol absorption inhibitor. Ezetimibe (Zetia®, Ezetrol®, Ezemibe®) is the only prescription drug currently in this class. This drug prevents dietary cholesterol from being absorbed from the small intestine and entering the blood, thus lowering blood cholesterol levels. Synergistic compositions comprising a cholesterol absorption inhibitor and a layered phyllosilicate material described herein is particularly contemplated.

F. Salicylic Acid

Also contemplated as a standard of care therapeutic in the combination therapy is salicylic acid (aspirin). Aspirin has been shown to have a protective effect against heart attacks in patients with clogged blood vessels, and can also be used in a composition according to the present invention. The cholesterol-reducing mechanism is believed to be based on the acidic properties of aspirin, and as such the acid deconjugates the bile:cholesterol complex (or cholesterol micelle), reducing bioavailability.

G. Phytosterols

In another embodiment, the standard of care therapeutic in the combination therapy is a phytosterol. Phytosterols, also known as plant sterols or stanols, are lipids having chemical structures similar to cholesterol, which are present in all plants including but not limited to vegetables, fruits, and grains, particularly in nuts, seeds, and plant oils. Phytosterols inhibit intestinal cholesterol absorption, thereby lowering plasma total and low-density lipoprotein (LDL) cholesterol levels. Daily consumption of about one to two grams of phytosterols reduces the risk for cardiovascular disease by about 25 to about 28% without causing any adverse effects. Twice per day consumption of about 0.40 grams of phytosterols or about 0.65 grams of phytosterol esters has also been shown to lower total cholesterol levels and LDL cholesterol levels by up to 10%. An extract of the soy plant—sitosterol—is available in a product called Take Control (Lipton). And an extract of pine needles—sitostanol—is available in a similar product called Benechol (McNeil). The use of policosanol, derived from waxes of various plants including, but not limited to, sugar cane and yams, is also contemplated. The use of stigmastanol (Sigma Aldrich) is also contemplated H. Alginates and Pectins In yet another embodiment, the standard of care therapeutic in the combination therapy is a polysaccharide including but not limited to, alginate, pectin, gellan gum, xanthan gum and zooglan. Alginates, pectins and modifications thereof are reported to interact with dietary cholesterol and affect its absorption and excretion (see U.S. Pat. Nos. 5,141,927; 5,597,810; 7,026,302, Japanese Patent No. 09235234, and Kimura et al., J. Ethnopharmacol, 54(1):47 54 (1996), the disclosures of which are incorporated herein by reference in their entireties).

I. Lecithin

In another embodiment, the standard of care therapeutic in the combination therapy is Lecithin (CAS #8002-43-5). Lecithin is usually used as a synonym for phosphatidylcholine, a phospholipid which is the major component of a phosphatide fraction isolated from egg yolk or soy beans. Lecithin is commercially available in high purity as a food supplement and for medical uses. For example, Lecithin 19 Grain is sold over the counter and has been reported to reduce cholesterol.

J. Nutraceuticals

Nutraceuticals are also contemplated as a standard of care therapeutic for use in the combination therapy. In one embodiment, the nutraceutical is an extract of green tea. Green tea contains volatile oils, vitamins, minerals, and caffeine, but the primary constituents of interest are the polyphenols, particularly the catechin called epigallocatechin gallate (EGCG). The polyphenols are believed to be responsible for most of green tea's roles in promoting good health.

Green tea has been shown to mildly lower total cholesterol levels and improve the cholesterol profile (decreasing LDL cholesterol and increasing HDL cholesterol) in most, (Kono et al., Japan. Prev Med., 21:526-31, 1992; Yamaguchi et al., NipYak Zas., 97:329-37, 1991; Sagesaka-Mitane et al., Chem Pharm Bull., 38:790-3, 1990; Stensvold et al., Prev Med., 21:546-53, 1992) but not all (Tsubono et al., Ann Epidemiol., 7:280-4, 1997) studies. Green tea may also promote cardiovascular health by making platelets in the blood less sticky.

In another embodiment, the nutraceutical is a dietary supplement selected from the group consisting of Cholest-Arrest™ (500 mg garlic and 200 mg lecithin); Cholest-away™ (700 mg Calcium carbonate, 170 mg magnesium oxide 50 μg chromium picolinate), Cholest-Off™ (900 mg of plant sterols/stanols), Guggul Bolic (750 mg of gugulipid (*Commiphora mukul* gum resin), and Kyolic® (600 mg aged garlic extract and 380 mg lecithin).

Kits and Unit Doses

In related variations of the preceding embodiments, a composition comprising a layered phyllosilicate material alone or in combination with one or more standard of care therapeutic(s) as described herein may be so arranged, e.g., in a kit or package or unit dose, to permit co-administration with one or more standard of care therapeutic(s), but the layered phyllosilicate material composition and the one or more standard of care therapeutic(s) are not in admixture. In another aspect, the layered phyllosilicate material composition and the one or more standard of care therapeutic(s) are in admixture. In some embodiments, the two components to the kit/unit dose are packaged with instructions for administering the two agents to a mammalian subject for treatment of one of the above-indicated disorders and diseases.

Other aspects and advantages of the present invention will be understood upon consideration of the following illustrative examples, which are not intended to be limiting in any way.

EXAMPLES

Example 1

The present Example demonstrates the ion exchange process of smectite clay from a Ca form or Na/Ca mixed forms to Na-rich smectite clay.

Raw smectite clay was dispersed into water to make a 3 wt % clay slurry. This clay has a Na content of 0.20 wt % and Ca content of 2.10 wt %. The elemental analysis was measured by an X-ray fluorescence method. The mixture was mixed thoroughly with a mechanical mixer. The pH value of the starting clay slurry is 7-8. An ion exchange resin, such as Amberlite 200C Na, is available from Rohm & Hass packed in a glass column with a 2-in diameter and a 20-in length. A liquid pump was used to pump the clay slurry through the column at 20 ml/min. Elemental analysis of the finished clay, dried from the slurry, indicated that the Na content is 3.45 wt % and Ca content is 0.17 wt %. The ion exchanged clay is called E1-Na-Clay. This clay had a basal spacing of 13 Å.

Example 2

Preparation of a Hydrogen Protonated Layered Phyllosilicate Material

The present Example demonstrates the ion exchange process to convert a sodium smectite clay to a hydrogen protonated smectite clay (i.e., Compound A).

Smectite clay comprising about 80% sodium and about 20% calcium/magnesium as exchangeable ions was processed to a particle size of approximately 74 μm and purified via the process described in U.S. Pat. No. 6,050,509. After purification, the smectite clay comprised predominantly sodium ions.

The purified sodium exchanged clay was dispersed into filtered DI water to make a 3 wt % clay slurry. The mixture was mixed thoroughly with a Silverson homogenizer. The pH value of the starting clay slurry was about 10. An hydrogen ion exchange resin, Amberlite FPC23H available from Rohm & Hass, was packed into two glass columns with a 2-in diameter and a 20-in length; one inch of space was left at the top of each column to promote flowability of the beads. The clay slurry was slowly mixed using a 3-inch dispersion blade at 800 rpm while a liquid pump was used to pump the clay slurry through two resin packed columns at 20 ml/min. The pH of the clay slurry was 2.3 after passing through the second column. The clay was then gamma irradiated to prevent bacterial contamination. The resulting hydrogen protonated smectite clay was designated as Compound A and was used in some of the in vivo assays described herein.

Compound A was measured for particle size distribution using the Coulter LS230 particle size analyzer. Circulation speed was set at 75%. Distribution was calculated using the Fraunhofer model. 1A 1:10 dilution of Compound A was made using a blender at 7,000 rpm for 5 minutes. The particle size measurements for Compound A were as follows:

| Sample | Mean (μm) | <10% (μm) | <25% (μm) | <50% (μm) | <75% (μm) | <90% (μm) |
| --- | --- | --- | --- | --- | --- | --- |
| Compound A | 10.41 | 0.71 | 1.71 | 8.34 | 16.53 | 24.87 |

Zeta potential and pH data was also measured. Compound A was diluted to 0.1 wt % and mixed using a blender at 7000 rpm for 3 minutes and then measured for pH and zeta potential (mV). The resulting zeta potential was −45.66 mV and the pH was 3.1.

Example 3

The present Example demonstrates the formation of protonated Octadecyl ammonium-treated smectite clay with Octadecyl ammonium acetate from the ion exchanged Na-smectite clay (E1-Na-clay) of Example 1.

100-g of sodium smectite clay E1-Na-clay was dispersed into 3000 ml water through a mechanical mixer. This clay slurry was heated to 80° C. 41.5 g of Octadecyl ammonium acetate from KAO Chemicals was added into the clay slurry. The clay showed excellent flocculation after the addition of the Octadecyl ammonium acetate. The pH of the clay reaction slurry was about 4. The clay was filtered with regular quantitative filter paper with the assistance of a mechanical vacuum pump. Then, the clay was dried in an oven over night at 80° C. and ground to pass through a 300-mesh screen as a fine powder. This modified clay was called E2-ODA-Clay.

Example 4

The present Example demonstrates the formation of protonated Octadecyl ammonium-treated smectite clay with a solution of Octadecyl ammonium ions in dilute HCl. (E3-ODA-Clay). This sample was measured by powder X-ray diffraction to determine the clay basal spacing after ion exchange. The result is listed in Table-1.

100-g of sodium smectite E1-Na-clay was dispersed into 3000 ml water through a mechanical mixer. This clay slurry was heated to 80° C. 33.8 g of Octadecyl amine was added into 1000 ml of 70° C. water and then mixed with 17.1 g of 10.5 N HCl. The Octadecyl amine-HCl solution was added into the clay slurry followed by mixing. The reaction slurry had a pH of 4. The clay showed excellent flocculation after the addition of the Octadecyl amine-HCl solution. The clay was filtered with regular quantitative filter paper with the assistance of a mechanical vacuum pump. Then, the clay was dried in an oven over night at 80° C. and ground to pass through a 300-mesh screen as a fine powder. This modified clay was called E3-ODA-Clay. This sample was measured by powder X-ray diffraction to determine the clay basal spacing after ion exchange. The result is listed in Table 2.

TABLE 2

Summary of the ODA treated clay prepared under different methods

| Example | Slurry pH | Slurry Filtration | Basal Spacing (Å) | Basal Spacing after Mixing into Caprolactam (Å) |
|---|---|---|---|---|
| E2-ODA-Clay | 4 | easy | 20 | 34 (15%), 34 (3%) |
| E3-ODA-Clay | 4 | easy | 20 | 34 (15%), 34 (3%) |

Example 5

Preparation of Protonated Lecithin Phyllosilicate Material

The present Example demonstrates the formation of protonated Lecithin (CAS #8002-43-5) treated smectite clay with a solution of Lecithin in dilute HCl (E3-ODS-Clay) (i.e., Compound B).

Preparation of Lecithin Dispersion: In a clean dry beaker, 10 g Lecithin was added to 150 mL of deionized water. The crude mixture was heated to 60-70° C. and stirred with a magnetic stirrer until fully dispersed.

Preparation of Surface Modified Purified Clay: In a separate beaker, 10 g of highly purified sodium bentonite clay was added to ~600 mL of deionized water. The solution was heated to >60° C. and stirred with a mechanical stirrer until the clay was fully dispersed (approximately 15-30 minutes). Concentrated (12M) HCl was slowly added to the fully dispersed clay until the dispersion had pH of 2. The viscosity of the dispersion will increase as the pH is lowered.

Preparation of Lecithin Modified Clay: the Lecithin dispersion was slowly added to the warm modified clay dispersion, stirred and heated for approximately 1 hour until the dispersion changes color from brown to tan/pink. The dispersion was filtered using a Buchner funnel and vacuum filtration apparatus. The filter cake was collected and placed in original beaker. The filter cake was redispersed in ~80 mL deionized water and stirred for 60 minutes at 60° C. The dispersion was filtered for a second time using a Buchner funnel and vacuum filtration apparatus. The filter cake was collected and dried overnight at approximately 60° C. The dried filter cake was then ground to the desired particle size of 100% of the particles less than 45 microns. The resulting smectite clay with lecithin was designated as Compound B and was used in some of the in vivo assays described herein.

Compound B was further measured for particle size distribution using the Coulter LS230 particle size analyzer. Circulation speed was set at 75%. Distribution was calculated using the Fraunhofer model. 1 wt % solutions were made of Compound B using a blender at 7,000 rpm for 5 minutes. The particle size measurements of Compound B were as follows:

| Sample | Mean (μm) | <10% (μm) | <25% (μm) | <50% (μm) | <75% (μm) | <90% (μm) |
|---|---|---|---|---|---|---|
| Compound B | 70.62 | 7.79 | 17.91 | 59.59 | 118.7 | 146.4 |

Zeta potential and pH data was also measured. Compound B was diluted to 0.1 wt % and mixed using a blender at 7000 rpm for 3 minutes and then measured for pH and zeta potential (mV). The resulting zeta potential was −32.06 mV and the pH was 3.6.

Example 6

Preparation of Layered Phyllosilicate Material with Surface Acid Treatment (Compound C)

The present Example demonstrates the preparation a layered phyllosilicate material with surface acid treatment (i.e., Compound C).

Bentonite was crushed, granulated and then sprayed with water as it traveled along a belt towards the extruder. The extruded bentonite was then sprayed with 75% $H_2SO_4$ which formed salts with the interlayer cations. The bentonite was then extruded once again to a smaller size. The acidified clay particles continued along the belt towards the activation tank. The tank was simultaneously filled with bentonite and acid for two hours. Steam was added to the $H_2SO_4$ acid stream prior to reaching the tank to reduce the concentration to 35% and to reach a temperature of 90° C., which was maintained throughout the acid activation process.

The bentonite was left to steep without agitation in circulating acid for an amount of time which depends on the application of the activated clay.

Following acid treatment, the freshly activated bentonite was subjected to two washing steps (i.e., wash A and wash B) to remove salts produced by the acid treatment. During wash A, 4% $H_2SO_4$ at 90° C. was circulated around the tank while the acid concentration of wash B was 2%. Subsequent to wash B, the tank was drained and the activated bentonite extrudates were shovelled from the tank to a stockpile. The activated bentonite extrudates were later subjected to the drier where the moisture is reduced and are broken into granules. The resulting nanobentonite compound with surface acid treatment was designated as Compound C and was used in some of the in vivo assays described herein.

Compound C was measured for particle size distribution using the Coulter LS230 particle size analyzer. Circulation speed was set at 75%. Distribution was calculated using the Fraunhofer model. 1 wt % solutions were made of Compound C using a blender at 7,000 rpm for 5 minutes. The particle size measurements of Compound C were as follows:

| Sample | Mean (μm) | <10% (μm) | <25% (μm) | <50% (μm) | <75% (μm) | <90% (μm) |
|---|---|---|---|---|---|---|
| Compound C | 12.97 | 2.23 | 3.87 | 7.10 | 15.99 | 34.53 |

Zeta potential and pH data was also measured. Compound C was diluted to 0.1 wt % and mixed using a blender at 7000 rpm for 3 minutes and then measured for pH and zeta potential (mV). The resulting zeta potential was −1.71 mV and the pH was 4.1.

Example 7

Preparation of Other Layered Phyllosilicate Materials

The present Example describes the preparation of layered phyllosilicate materials designated herein as Compound G, Compound H, Compound I, Compound J, Compound K, Compound L, and Compound M.

Preparation of Compound G: A smectite clay comprising about 5% sodium and about 95% calcium/magnesium as exchangeable ions was processed to a particle size of approximately 74 μm and purified via the process described in U.S. Pat. No. 6,050,509. After purification, the smectite clay comprised predominantly sodium ions.

The purified sodium exchanged clay was dispersed into filtered DI water to make a 2.7 wt % clay slurry. The mixture was mixed thoroughly with a Silverson homogenizer. The pH value of the starting clay slurry was about 10. An hydrogen ion exchange resin, Amberlite FPC23H (Rohm & Hass) was packed into two glass columns with a 2-in diameter and a 20-in length; one inch of space was left at the top of each column to promote flowability of the beads. The clay slurry was slowly mixed using a 3-inch dispersion blade at 800 rpm while a liquid pump was used to pump the clay slurry through two resin packed columns at 20 ml/min. The clay was then gamma irradiated to prevent bacterial contamination. The resulting clay was designated as Compound G.

Preparation of Compound H: A smectite clay comprising about 70% sodium and about 30% calcium/magnesium as exchangeable ions was processed to a particle size of approximately 74 μm and purified via the process described in U.S. Pat. No. 6,050,509. After purification, the smectite clay comprised predominantly sodium ions.

The purified sodium exchanged clay was dispersed into filtered DI water to make a 2.6 wt % clay slurry. The mixture was mixed thoroughly with a Silverson homogenizer. The pH value of the starting clay slurry was about 10. An hydrogen ion exchange resin, Amberlite FPC23H (Rohm & Hass) was packed into two glass columns with a 2-in diameter and a 20-in length; one inch of space was left at the top of each column to promote flowability of the beads. The clay slurry was slowly mixed using a 3-inch dispersion blade at 800 rpm while a liquid pump was used to pump the clay slurry through two resin packed columns at 20 ml/min. The clay was then gamma irradiated to prevent bacterial contamination. The resulting clay was designated as Compound H.

Preparation of Compound I. A smectite clay comprising about 80% sodium and about 20% calcium/magnesium as exchangeable ions was processed to a particle size of approximately 74 μm and purified via the process described in U.S. Pat. No. 6,050,509. After purification, the smectite clay comprised predominantly sodium ions. The clay was then gamma irradiated to prevent bacterial contamination. The resulting clay was designated as Compound I.

Preparation of Compound J: A smectite clay comprising about 80% sodium and about 20% calcium/magnesium as exchangeable ions was processed to a particle size of approximately 74 μm and purified via the process described in U.S. Pat. No. 6,050,509. After purification, the smectite clay comprised predominantly sodium ions. A 2.8 wt % mixture of the purified smectite clay and filtered deionized water was made using a blender at 7000 rpm for 3-5 minutes. The resulting clay slurry was then treated with 6N HCl drop wise until a pH of 2.2 was obtained. The clay was then gamma irradiated to prevent bacterial contamination. The resulting surface acid treatment smectite clay was designated as Compound J.

Preparation of Compound K: A smectite clay comprising about 80% sodium and about 20% calcium/magnesium as exchangeable ions was processed to a particle size of approximately 74 μm and purified via the process described in U.S. Pat. No. 6,050,509. After purification, the smectite clay comprised predominantly sodium ions.

The purified sodium exchanged clay was dispersed into filtered DI water to make a 3 wt % clay slurry. The mixture was mixed thoroughly with a Silverson homogenizer. The pH value of the starting clay slurry was about 10. An hydrogen ion exchange resin, Amberlite FPC23H (Rohm & Hass) was packed into two glass columns with a 2-in diameter and a 20-in length; one inch of space was left at the top of each column to promote flowability of the beads. The clay slurry was slowly mixed using a 3-inch dispersion blade at 800 rpm while a liquid pump was used to pump the clay slurry through two resin packed columns at 20 ml/min. The pH of the clay slurry was 2.3 after passing through the second column. The slurry was then treated with NaOH drop wise until a pH of 10 was obtained. Final mixture of the slurry 2.7 wt %. The clay was then gamma irradiated to prevent bacterial contamination. The resulting clay was designated as Compound K.

Preparation of Compound L: A smectite clay comprising about 70% sodium and about 30% calcium/magnesium as exchangeable ions was processed to a particle size of approximately 74 μm and purified via the process described in U.S. Pat. No. 6,050,509. After purification, the smectite clay comprised predominantly sodium ions. The clay was then gamma irradiated to prevent bacterial contamination. The resulting sodium ion exchanged claim was designated as Compound L.

Preparation of Compound M: A smectite clay comprising about 5% sodium and about 95% calcium/magnesium as exchangeable ions was processed to a particle size of approximately 74 μm and purified via the process described in U.S. Pat. No. 6,050,509. After purification, the smectite clay comprised predominantly sodium ions. The clay was then gamma irradiated to prevent bacterial contamination. The resulting sodium ion exchanged claim was designated as Compound M.

Example 8

Layered Phyllosilicate Material Reduced Cholesterol in vitro

The present Example was performed to determine the effect of various phyllosilicate materials on the adsorption of cholesterol from an aqueous solution.

Cholesterol powder was obtained from Aldrich Chemical Company (Milwaukee, Wis.). A stock solution of cholesterol was prepared by dissolving the pure crystals in acetonitrile and then injecting an amount into purified water (pH 6.8) to yield a solution concentration of 4 mg/mL. The exact concentration of the stock solution was verified by liquid chromatography.

Each isotherm consisted of triplicate 5 mL aqueous samples of Cholesterol made from dilutions of the stock to yield approximate concentrations of 0.5, 1.0, 1.5, 2.0, 2.5, 3.0, 3.5, and 4.0 ug/mL and placed in sterile 17×100 mm polypropylene centrifuge test tubes. A suspension of layered phyllosilicate material was prepared by weighing 10 mg of layered phyllosilicate material into a 25 mL Erlenmeyer flask and pipetting the appropriate volume of water in the flask to make the clay concentration 1 mg/mL. A stir bar was added to the flask, and the suspension was mixed to keep the slurry homogeneous. From this suspension, 50 uL (containing 50 ug of clay) was pipetted out with an autopipetor and added to each 5 mL test sample. Four controls were also prepared: a water control containing no cholesterol, cholesterol controls containing 0.5 and 4.0 ug/mL cholesterol, and a control containing 5 mL water and 50 μg of clay. Samples were capped and mixed by shaking at 1000 rpm at 37° C. for 2 hours.

After mixing was completed, the samples were centrifuged at 10000 rpm at 37° C. for 15 minutes to separate the layered phyllosilicate material from the supernatant. The samples were then analyzed by liquid chromatography. Analysis of the samples showed non-detectable levels of cholesterol remaining in the supernatant liquid indicating quantitative sorption and removal of the cholesterol from the aqueous liquid by the layered phyllosilicate material.

Example 9

Layered Phyllosilicate Material Reduces Hypercholesteremia in an Animal Model

The present Example will be performed to determine the effect of various layered phyllosilicate materials on plasma lipids in rabbits.

Rabbits are appropriate animals for the study of the effects of lipid-lowering agents because diet can be manipulated to induce hypercholesterolaemia (Kroon et al., Atherosclerosis, 44:41-48, 1982; Prior et al., Archives of Pathology, 71:82-94, 1961; Kolodgie et al., *Arterioscler Thromb Vase Biol.*, 16:1454-1464, 1996). The cholesterol-fed rabbit model has previously been used to demonstrate the lipid-lowering effects of statins (Nielsen et al. Pharmacol Toxicol., 72(3): 148-151, 1993). In this study, New Zealand white male rabbits (2.0 to 2.5 kg; Jeo-Bet Rabbits LTD, Aldon B.C., Canada) that exhibit hypercholesterolemia induced by a fat/cholesterol-enriched diet as previously published by Verd et al. (Br. J. of Pharmacology, 127:1479-1485, 1999) will be used. The fat/cholesterol-enriched diet will consist of Purina rabbit chow supplemented with 14.0% (weight/volume) coconut oil and 0.50% (weight/volume) cholesterol.

Male New Zealand white rabbits (n=30; Control group, Simvastatin Group (Risovic et al., Drug Dev. Industry Pharm., 32:1-7, 2006), Group A layered phyllosilicate material (nanobentonite dispersed in deionized water), Group B layered phyllosilicate material (nanobentonite with surface acid treatment) and Group C layered phyllosilicate material (nanobentonite with surface modified with lecithin) will be housed in individual cages in a room with constant humidity and temperature (22° C.) under a 12 hour light-dark cycle, and fed a standard diet for 7 days. After 7 days, animals will be fed 10 g of a regular chow diet plus 100 g of the same diet supplemented with 0.5% (w/v) cholesterol and 14.0% (w/v) coconut oil for 28 days. The final diet administered to these rabbits (following dilution of 100 g of high fat/cholesterol diet with 10 g of regular chow) consistent of 0.45% (w/v) cholesterol and 12.75% (w/v) coconut oil. Following 28 days on this diet, the animals will be assigned based on their 16 hour post-meal plasma cholesterol and triglyceride concentrations, into five groups of six animals each with no statistically significant differences between total plasma cholesterol and triglyceride concentrations.

For an additional 28 days (day 28 to day 56 of the study), a group of control animals (n=6) will be maintained on the same diet (10 g regular chow diet plus 100 g of cholesterol/coconut diet) and four groups of animals will be fed 100 g of cholesterol/coconut diet plus 10 g regular chow diet containing either simvastatin (3 mg/kg/day; n=6), Formulation A (20 mg/kg/day; n=6), Formulation B (20 mg/kg/day; n=6) and Formulation C (20 mg/kg/day; n=6). Whole blood will be collected (3 ml) prior to and 28 days after initiation of treatment for plasma lipid determinations.

Plasma total cholesterol and triglyceride concentrations will be directly quantified using enzymatic kits (Sigma Aldrich). HDL cholesterol concentrations will be determined using the dextran sulfate-$Mg^{2+}$ precipitation method as developed by Wamick et al. (Clin Chem., 28:1379-1388, 1982). The Friedewald equation for determining LDL cholesterol can not be used in this rabbit fed model (Friedewald et al., Clin Chem., 18:499-502, 1972). However, measurement of apoB cholesterol (which takes into account LDL cholesterol) concentrations will be determined by subtracting HDL cholesterol concentrations from total cholesterol concentrations.

The 3 mg/kg/day simvastatin dose selected in this study was based on results completed in the same animal model by Verd et al. (Br. J. of Pharmacol., 127:1479-1485, 1999).

Results will be expressed as mean±standard error of the mean (SEM). Statistical analyses will be conducted using an analysis of variance (PCANOVA; Human Dynamic Systems) and assuming unequal variance (Newman Keuls post-hoc test; we assumed unequal variance). Variables compared among treatment groups include, weight gain, total plasma cholesterol, total plasma triglyceride, HDL-cholesterol and ApoB cholesterol. A p-value of less than 0.05 will indicate a significant difference between treated and untreated groups.

It is contemplated that treatment with layered phyllosilicate material A, B or C will result in lower total plasma cholesterol, lower plasma triglyceride, lower LDL-cholesterol and lower ApoB cholesterol levels when compared to the control.

Example 10

Layered Phyllosilicate Material Reduces Hypercholesteremia in Another Animal Model

The study performed in Nishide et al., J. Appl. Phycology, 5:207-211, 1993 is repeated using a layered phyllosilicate material described herein in conjunction with an alginate. Treatment with the alginate alone will be the control. It is contemplated that the combination treatment of the layered phyllosilicate material and the alginate will result in lower total plasma cholesterol when compared to the control.

Example 11

Layered Phyllosilicate Material Reduced Hypercholesteremia in an Animal Model

The following Example confirms that a layered phyllosilicate material exhibits a cholesterol-lowering effect in a severe dyslipidemic model (Nielsen et al. Pharmacol Toxicol., 72(3):148-151, 1993).

Male New Zealand white rabbits (n=24; Control group [n=5], Simvastatin Group [n=4], Compound A Group [n=5], Compound B Group [n=5] and Compound C Group [n=5]) were housed in individual cages in a room with constant humidity and temperature (22° C.) under a 12 h light-dark cycle, and fed a standard diet for 7 days. After 7 days, animals were fed 10 g of a regular chow diet plus 100 g of the same diet supplemented with 0.5% (w/v) cholesterol and 14.0% (w/v) coconut oil for an additional 28 days. The final diet administered to these rabbits (following dilution of 100 g of high fat/cholesterol diet with 10 g of regular chow) consistent of 0.45% (w/v) cholesterol and 12.75% (w/v) coconut oil. Following 28 days on this diet, the animals were assigned based on their 16 h post-meal plasma cholesterol and triglyceride concentrations, into five groups with no statistically significant differences between total plasma cholesterol and triglyceride concentrations. The total plasma cholesterol, ApoB, HDL and triglyceride concentrations of the subjects prior to drug treatment is set forth in FIGS. 1-4, respectively.

For an additional 21 days (day 35 to day 56 of the study), a group of control animals (n=5) were maintained on the same diet (10 g regular chow diet plus 100 g of cholesterol/coconut diet) and four groups of animals were fed 100 g of cholesterol/coconut diet plus 10 g regular chow diet containing either simvastatin (3 mg/kg/day; n=4), Compound A (hydrogen protonated layered phyllosilicate material (prepared as described above in Example 2); 20 mg/kg/day; n=5), Compound B (layered phyllosilicate material with surface modified with lecithin prepared as described above in Example 5); 20 mg/kg/day; n=5) and Compound C (layered phyllosilicate material with surface acid treatment prepared as described above in Example 6) 20 mg/kg/day; n=5). Whole blood was collected (3 ml) prior to and 7, 14, and 21 days after initiation of treatment for plasma lipid determinations.

Plasma total cholesterol and triglyceride concentrations were directly quantified using enzymatic kits (Sigma Aldrich). HDL-cholesterol concentrations were determined using the dextran sulfate-$Mg^+$ precipitation method as developed by Warnick et al. (9). The Friedewald equation for determining LDL cholesterol could not be used in this rabbit fed model (10). However, measurement of apoB cholesterol (which takes into account LDL-cholesterol) concentrations were determined by subtracting HDL-cholesterol concentrations from total cholesterol concentrations.

The 3 mg/kg/day simvastatin dose selected in this study was based on results completed in the same animal model by Verd et al. (Br. J. of Pharmacol., 127:1479-1485, 1999).

Statistical analysis: Results are expressed as mean±standard error of the mean (SEM). Statistical analyses were conducted using an analysis of variance (PCANOVA; Human Dynamic Systems) and assuming unequal variance (Newman Keuls post-hoc test; assuming unequal variance). Variables compared among treatment groups include, weight gain, total plasma cholesterol, total plasma triglyceride, HDL-cholesterol and ApoB-cholesterol. A p-value of less than 0.05 indicates a significant difference between treated and untreated groups.

Results:

The effect of the high cholesterol diet on the levels of total plasma cholesterol, HDL, ApoB and triglycerides prior to drug treatment is set forth in Table 3.

TABLE 3

Effect of coconut oil/cholesterol feeding[1] on plasma cholesterol, HDL-cholesterol, ApoB- cholesterol and triglyceride concentrations

| | Total Chol (mg/dL) | HDL- Chol (mg/dL) | ApoB- Chol (mg/dL) | Total TG (mg/dL) |
|---|---|---|---|---|
| | Day 0 to Day 7, Animal acclimation time | | | |
| Day 7 | 28 ± 2.9 | 36 ± 4 | BLQ* | 26 ± 3 |
| Day 28 | 1048 ± 91[a] | 136 ± 27[a] | 912 ± 82 | 74 ± 7[a] |
| Day 35 | 1170 ± 95[a] | 108 ± 19[a] | 1063 ± 94 | 99 ± 10[a] |

Data presented as mean ± SEM (n = 24).
[a]p < 0.05 vs. Day 7.
Abbreviations: Chol, cholesterol; HDL, high-density lipoproteins; ApoB, Apo lipoprotein B; TG, triglycerides; BLQ*; below the limit of quanitation.
[1]high cholesterol diet consists of 0.45% w/v cholesterol plus 12.75% w/v coconut oil Total body weight and food intake. No significant differences in weight gain were observed throughout the duration of the study between the different treatment groups. However, some differences in food intake were observed. All rabbits were provided a set diet and received 110 g of food daily.

Total cholesterol and triglyceride concentrations. The effects of simvastatin on plasma total cholesterol are reported in Table 4 and FIG. 5. The effects of simvastatin on triglyceride levels are reported in FIG. 6.

TABLE 4

Total plasma and ApoB cholesterol concentrations in New Zealand Male Rabbits fed a high cholesterol diet[@] at the beginning (day 35) and at the end (day 56) of drug treatment.

| | Total Cholesterol (mg/dL) | | | ApoB-Cholesterol (mg/dL) | | |
|---|---|---|---|---|---|---|
| Day | 35 | 56 | % C | 35 | 56 | % C |
| CON | 1170 ± 283 | 1968 ± 418 | +68% | 1179 ± 326 (n = 4) | 1917 ± 415 | +63% |
| SVT | 1167 ± 276 | 556 ± 122* | −52% | 1092 ± 265 | 517 ± 121* | −53% |
| A | 1172 ± 272 | 1544 ± 387 | +32% | 1075 ± 257 | 1505 ± 390 | +40% |
| B | 1178 ± 157 | 1813 ± 338 | +54% | 1058 ± 138 | 1744 ± 332 | +65% |
| C | 1164 ± 158 | 1850 ± 231 | +59% | 1086 ± 154 | 1768 ± 229 | +63% |

Data is presented as mean ± SEM; n = 5 in each treatment group except SVT where it is n = 4;
[@]high cholesterol diet consists of 0.45% w/w cholesterol plus 12.75% coconut oil.
*p < 0.05 vs. CON.
Abbreviations: ApoB, Apo lipoprotein B; CON, control; SVT, simvastatin 3 mg/kg/day; A, compound A 20 mg/kg/day; B, compound B 20 mg/kg/day; C, compound C 20 mg/kg/day; % C, percentage change from Day 35 to Day 56.

Figure 5:
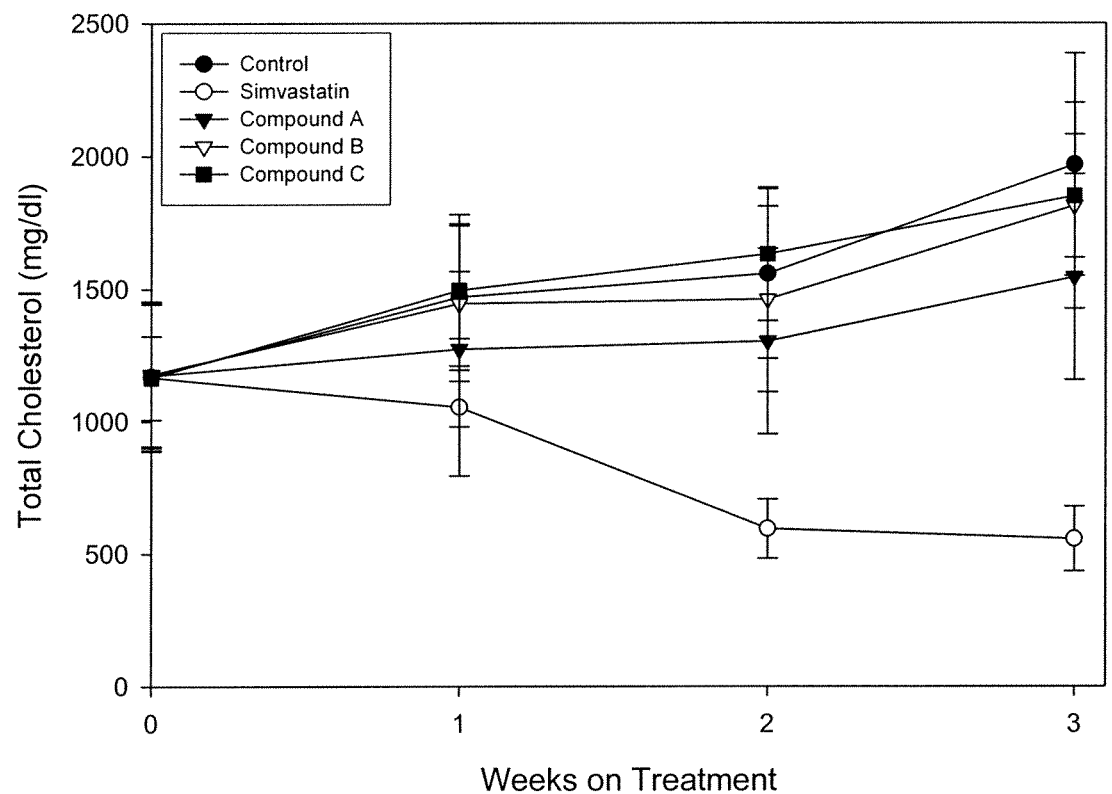
FIG. 5 shows the effects of Compounds A, B and C and Simvastatin on total plasma cholesterol levels compared to a control.
Figure 6:
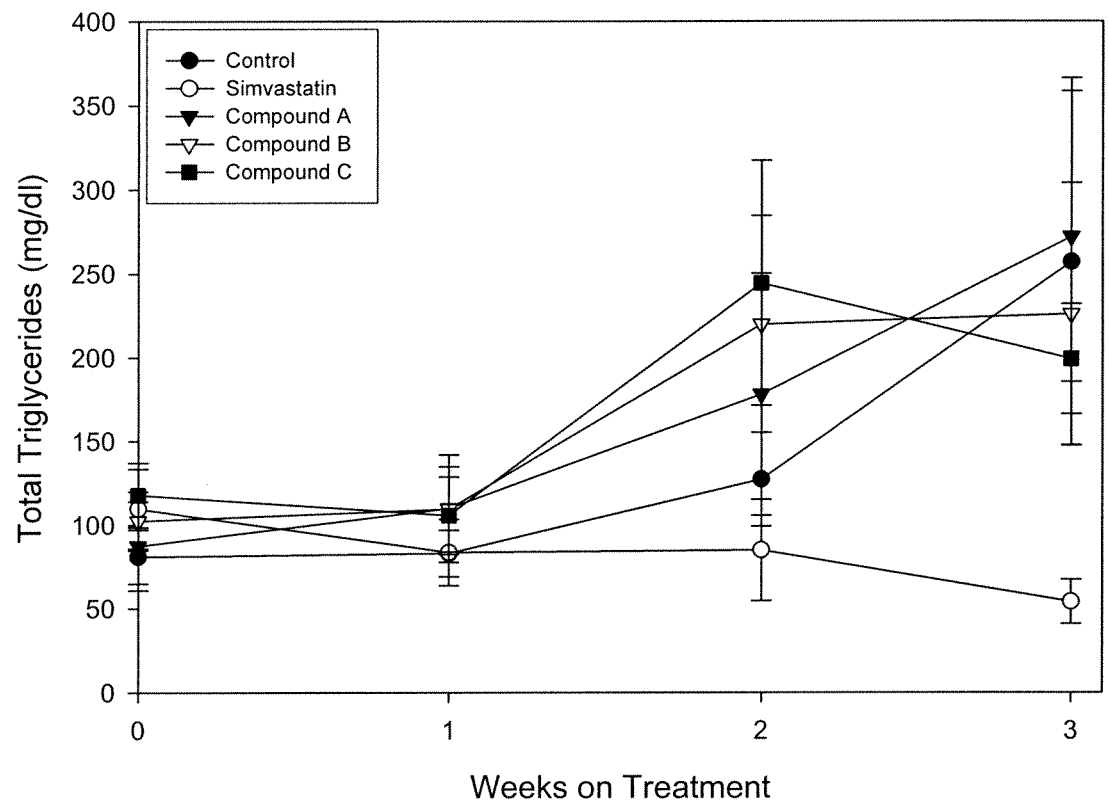
FIG. 6 shows the effects of Compounds A, B and C and Simvastatin on total plasma triglyceride levels compared to a control.

The effect of treatment with Compounds A, B and C and Simvastatin on total plasma cholesterol concentrations are set forth in Table 4 and FIG. 5. Simvastatin treatment significantly reduced the increase in total plasma cholesterol and triglyceride concentrations between the beginning (day 35) and the end (day 56) of drug-treated compared to non-treated controls (FIGS. 5 and 6). Compound A treatment reduced the increase in total plasma cholesterol concentrations between the beginning (day 35) and the end (day 56) of Compound A treated compared to non-treated controls (Table 4 and FIG. 5). Compounds B and C had no effect on total plasma cholesterol concentrations. In addition, Compounds A, B and C did not affect total plasma triglyceride concentrations (FIG. 6). The effects seen by Compound A suggest its activity is primarily in the gastrointestinal tract and affects only dietary cholesterol absorption, while the effect of simvastatin is primarily involved in cholesterol cellular synthesis.

HDL and apoB cholesterol concentrations. The effects of simvastatin on plasma apoB and HDL cholesterol concentrations are reported in FIGS. 7 and 8, respectively. No statistically significant differences in plasma HDL cholesterol levels were observed in the Simvastatin group between the beginning (day 35) and the end (day 56) of drug treatment compared to non-treated controls (FIG. 8). Simvastatin treatment significantly reduced the increase in apoB-cholesterol concentration between the beginning (day 35) and the end (day 56) of drug treatment compared to non-treated controls (FIG. 7).

Figure 7:
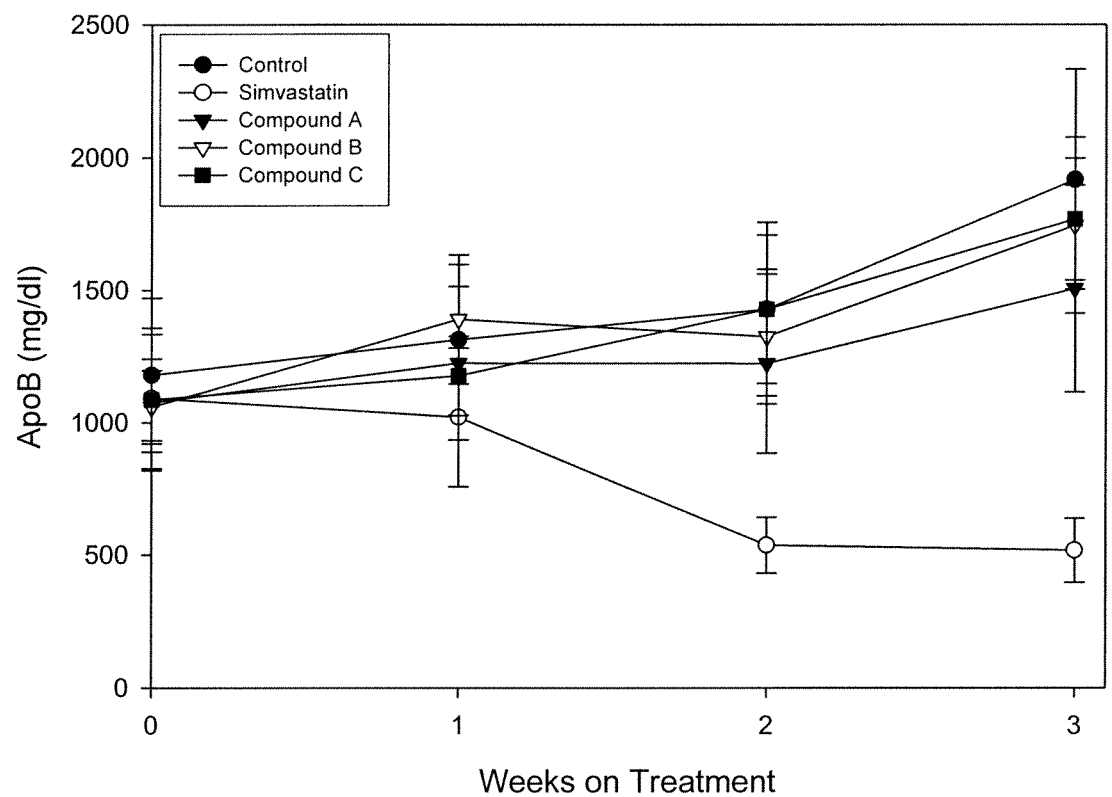
FIG. 7 shows the effects of Compounds A, B and C and Simvastatin on HDL cholesterol levels compared to a control.
Figure 8:
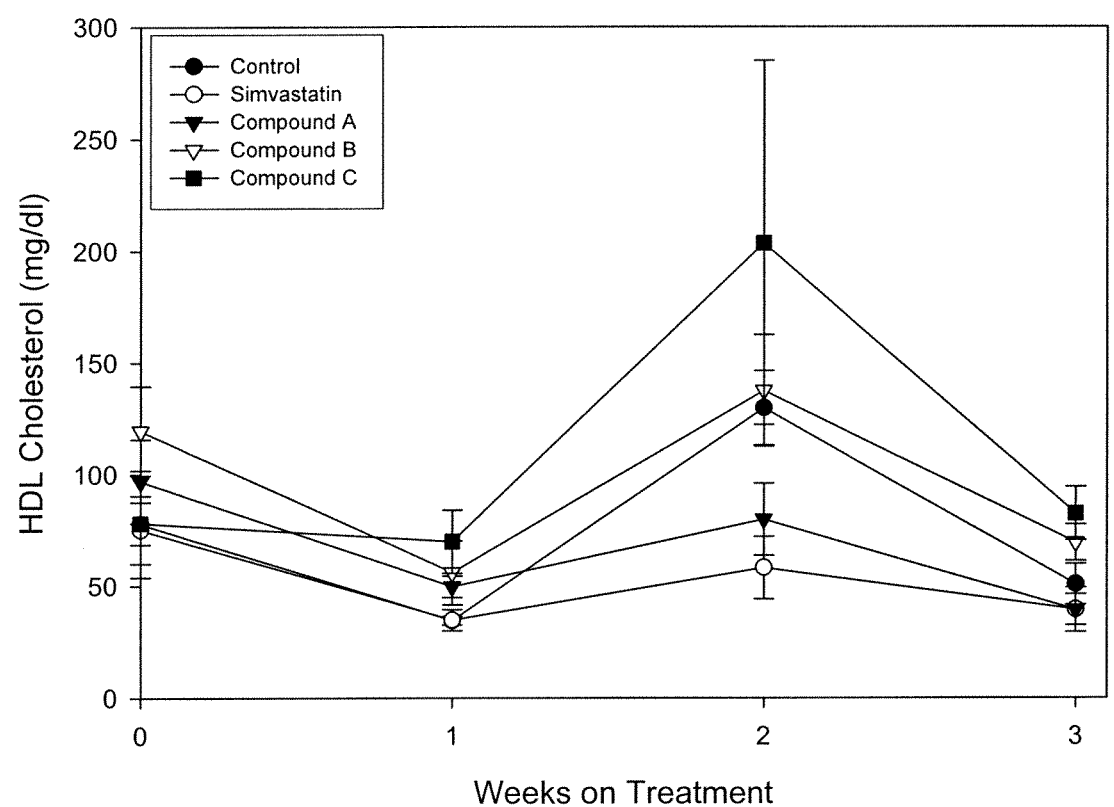
FIG. 8 shows the effects of Compounds A, B and C and Simvastatin on total ApoB levels compared to a control.

Treatment with Compound A reduced the increase in apoB-cholesterol concentrations between the beginning (day 35) and the end (day 56) of drug treatment compared to non-treated controls (FIG. 7). Compounds B and C and no effect on apoB cholesterol concentrations. In addition, Compounds A, B and C did not affect HDL cholesterol concentrations (FIG. 8).

The foregoing results confirm that Compound A (hydrogen protonated layered phyllosilicate material) exhibits a cholesterol-lowering activity in a severe dyslipidemic model. Thus, the use of a hydrogen protonated layered phyllosilicate material for the treatment of hypercholesteremia is specifically contemplated.

Example 12

Layered Phyllosilicate Material Reduced Hypercholesteremia in a Rat Model

The following Example was performed to determine the bioavailability and pharmacokinetics of dietary cholesterol following oral administration of different layered phyllosilicate material compounds to male Sprague Dawley rats, using the methodology reported in Wassan et al. J. Pharmaceut. Sci., 90:23-28, 2001.

Preparation of cholesterol formulation: Commercially available 20% Intralipid® was diluted by external phase of emulsion to reach a triglyceride concentration of 10% v/v. Cold cholesterole as dissolved in 100% ethanol (1 mg/75 µl) and the solution was slowly added to the 10% Intralipid® with magnetic stirring. [$^3$H]cholesterol toluene solution (25 µl/ml) was then slowly added and then vortexed for 30 seconds. The formulation was then mixed by magnetic stirring for an additional 30 minutes until ready for administration. The final formulation contained 90% of the 10% Intralipid®, 7.5% ethanol and 2.5% toluene. The final concentrations of cold and radiolabeled cholesterol were 1 mg/ml and 25 µCi/ml, respectively.

Preparation of ezetimibe formulation: Commercially available ezetimibe tablets were crushed and suspended in double distilled water to reach final ezetimibe concentration of 5 mg/ml. The suspension was briefly vortexed and then stirred using a magnetic stirrer for about 1 hour until ready for administration.

Preparation of the stigmastanol formulation: Stigmastanol was pre-wetted by Tween 80 (1% v/v final concentration) and suspended in 2% sodium carboxymethyl cellulose solution in double distilled water. The suspension was briefly vortexed for about 3 minutes, sonicated (Bransonic®93510) for 2 hours at ambient temperature and then stirred with a magnetic stirrer for 30 minutes until ready for administration. The final concentration of stigmastanol in the suspension was 25 mg/ml.

Experimental design: All rats used in this study were cared for in accordance with the principles promulgated by the Canadian Council on Animal Care and the University of British Columbia. Adult male Sprague Dawley rats (weighing approximately 350 g) were obtained from UBC animal care unit (Vancouver, B.C., Canada). The rats were maintained under a 12 hour light (0700-0900)/dark cycle and supplied with a standard laboratory diet (PMI Feeds, Richmond, Va., USA) and water ad libitum. The right external jugular vein was cannulated with a two-part catheter consisting of PE 50 connected to a short length of 0.02-inch silastic tubing inserted 3.2 cm past the clavicle (Hauss et al., Contemp Top Lab Anim Sci., 37(3):56-58 1998). The jugular cannula was tunneled beneath the skin and exteriorized through a small stab wound in the back of the neck. The animals were outfitted with jacket-and-tether assemblies and placed in metabolism cages for the duration of the study.

Following completion of the surgical procedures, the animals were fasted overnight and permitted to recover for 16-20 hours. Free access to a drinking solution consisting of 5% glucose in lactated Ringer's solution was permitted postoperatively and throughout the study. The following treatment protocol was used. Following an overnight fast (12-16 hours), rats were divided into one of the following fourteen treatment groups and received a single-dose oral gavage (1 g Intralipid emulsion) at 0700 h of either:

(1) [$^3$H]Cholesterol (25 µCi)+1 mg cholesterol/1 g 10% Intralipid+NS (Vehicle control), n=11;

(2) Sitostanol (stigmastanol) (50 mg/kg by weight)+[$^3$H] Cholesterol (25 µCi)+1 mg cholesterol/1 g 10% Intralipid (Positive Control), n=6;

(3) Zetia® (ezetimibe) (10 mg/kg by weight)+[$^3$H]Cholesterol (25 µCi)+1 mg cholesterol/1 g 10% Intralipid (Positive control), n=7;

(4) Sodium Bentonite Alone Compound (Sodium Bentonite Reference Control—smectite claim where exchangeable ions are about 80% sodium ions and about 20% calcium/magnesium ions) (50 mg/kg by weight)+[$^3$H]Cholesterol (25 µCi)+1 mg cholesterol/1 g 10% Intralipid, n=7;

(5) Compound A (prepared as described above in Example 2) (20 mg/kg by weight)+[$^3$H]Cholesterol (25 µCi)+1 mg cholesterol/1 g 10% Intralipid, n=5;

(6) Compound A (prepared as described above in Example 2) (50 mg/kg by weight)+[$^3$H]Cholesterol (25 µCi)+1 mg cholesterol/1 g 10% Intralipid. n=6;

(7) Compound A (prepared as described above in Example 2) (100 mg/kg by weight)+[$^3$H]Cholesterol (25 µCi)+1 mg cholesterol/1 g 10% Intralipid, n=6;

(8) Compound G (prepared as described above in Example 7) (50 mg/kg by weight)+[$^3$H]Cholesterol (25 µCi)+1 mg cholesterol/1 g 10% Intralipid, n=6;

(9) Compound H (prepared as described above in Example 7) (50 mg/kg by weight)+[$^3$H]Cholesterol (25 μCi)+1 mg cholesterol/1 g 10% Intralipid, n=6;

(10) Compound I (prepared as described above in Example 7) (50 mg/kg by weight)+[$^3$H]Cholesterol (25 μCi)+1 mg cholesterol/1 g 10% Intralipid, n=6;

(11) Compound J (prepared as described above in Example 7) (50 mg/kg by weight)+[$^3$H]Cholesterol (25 μCi)+1 mg cholesterol/1 g 10% Intralipid; n=5;

(12) Compound K (prepared as described above in Example 7) (50 mg/kg by weight)+[$^3$H]Cholesterol (25 μCi)+1 mg cholesterol/1 g 10% Intralipid, n=6;

(13) Compound L (prepared as described above in Example 7) (50 mg/kg by weight)+[$^3$H]Cholesterol (25 μCi)+1 mg cholesterol/1 g 10% Intralipid, n=6; or

(14) Compound M (prepared as described above in Example 7) (50 mg/kg by weight)+[$^3$H]Cholesterol (25 μCi)+1 mg cholesterol/1 g 10% Intralipid, n=6.

Treatment groups 1-3 were designed to demonstrate that the animal model is working as expected and to show the effects of Sitostanol and Zetia on the reduction of cholesterol absorption as compared to the vehicle controls. Treatment groups 4-14 were designed to demonstrate the effects of various layered phyllosilicate materials on the reduction of cholesterol in a severe dyslipidemic model. All of test Compounds A, G, H, I, J, K, L or M were given as a separate slurry to the animal by oral gavage.

Following oral administration, serial blood samples were collected into EDTA-coated tubes predose and at 10 minutes predosing and at 0.5, 1, 2, 4, 6, 10, 24 28, 32 and 48 hours postdosing. The withdrawn blood was replaced by equal volume of normal saline to prevent hypovolemia. Rats remained fasted throughout the duration of blood sampling (12 h predosing+24 h postdosing=40 h total fasting). Plasma was obtained by centrifugation and analyzed for [$^3$H] cholesterol by radioactivity. The concentration of administered cholesterol in plasma was determined against external calibration curves by means of radioactivity and expressed as ng/ml equivalent. It was previously shown (by thin layer chromatography) that greater than 90% of radioactivity counts in plasma following oral administration of [$^3$H]cholesterol in rats were either associated with either esterified or unesterified cholesterol (Wasan et al., J. Pharm. Sci., 90:23-28, 2001).

Analysis of [$^3$H]Cholesterol: Radiolabeled cholesterol concentrations in plasma was determined against external calibration curves (corrected for quenching and luminescence) using radioactivity. Total cholesterol concentrations were determined using enzymatic assay kits purchased from Sigma Diagnostics (St. Louis Mo.).

Cholesterol Absorption and Pharmacokinetic Data Analysis: Plasma concentration versus time data for [$^3$H]Cholesterol in individual animals was analyzed by noncompartmental methods using WinNonlin software for DOS (version 1.1).

Statistical Analysis: All analyses were performed using the SAS system (SAS Institute Inc.). AUC, maximum concentration (Cmax), and time of maximum concentration (Tmax) will be statistically compared using analysis of variance (ANOVA).

Results: Results indicated that Compounds A, G, H, I and M were successful in reducing cholesterol absorption in the rat compared to the control. See Table 5 below and FIG. 9.

TABLE 5

AUC calculated from plasma concentration-time profiles of cholesterol when administered with different layered phyllosilicate material compounds.

| Treatment group | $AUC_{0-48\,h}$ h*ng/ml (mean ± SEM) | % of control group* |
|---|---|---|
| Control, n = 11 (cholesterol + NS) | 80861 ± 5911 | 100% |
| Cholesterol + ezetimibe 10 mg/kg, n = 7 | 6937 ± 462 | 8.6% |
| Cholesterol + stigmastanol control 50 mg/kg, n = 6 | 55742 ± 3764 | 68.9% |
| Cholesterol + compound A 50 mg/kg, n = 6 | 55400 ± 7555 | 68.5% |
| Cholesterol + compound A 50 mg/kg, TID (batch 2) | 59163 ± 2755 | 73.2% |
| Cholesterol + compound A 50 mg/kg, (batch 2) | 55723 ± 4707 | 68.9% |
| Cholesterol + compound A 100 mg/kg, n = 6 | 49609 ± 2090 | 61.4% |
| Cholesterol + bentonite alone 50 mg/kg, n = 7 | 79744 ± 4707 | 98.6% |
| Cholesterol + compound A 20 mg/kg, n = 5 | 72227 ± 10560 | 89.3% |
| Cholesterol + compound H 50 mg/kg, n = 6 | 66220 ± 4749 | 81.9% |
| Cholesterol + fresh compound H 100 mg/kg, n = 5 | 74655 ± 5336 | 92.3% |
| Cholesterol + compound G 50 mg/kg, n = 6 | 76973 ± 8383 | 95.2% |
| Cholesterol + compound G batch 2, 100 mg/kg | 54313 ± 9551 | 67.2% |
| Cholesterol + compound K 50 mg/kg, n = 6 | 90992 ± 13460 | 112.5% |
| Cholesterol + compound I 50 mg/kg, n = 6 | 70718 ± 9019 | 87.5% |
| Cholesterol + compound J 50 mg/kg, n = 5 | 99511 ± 7415 | 123% |
| Cholesterol + compound L 50 mg/kg, n = 6 | 83748 ± 6794 | 103.6% |
| Cholesterol + compound M 50 mg/kg, n = 6 | 64604 ± 6214 | 79.9% |

*% control group means % reduction in cholesterol compared to the control. For example, for ezetimibe, the quantity of adsorbed cholesterol was 8.6% compared to the control. Therefore, administration of ezetimibe resulted in 91.4% lower radioactive labeled cholesterol measured in the blood plasma.

Figure 9:
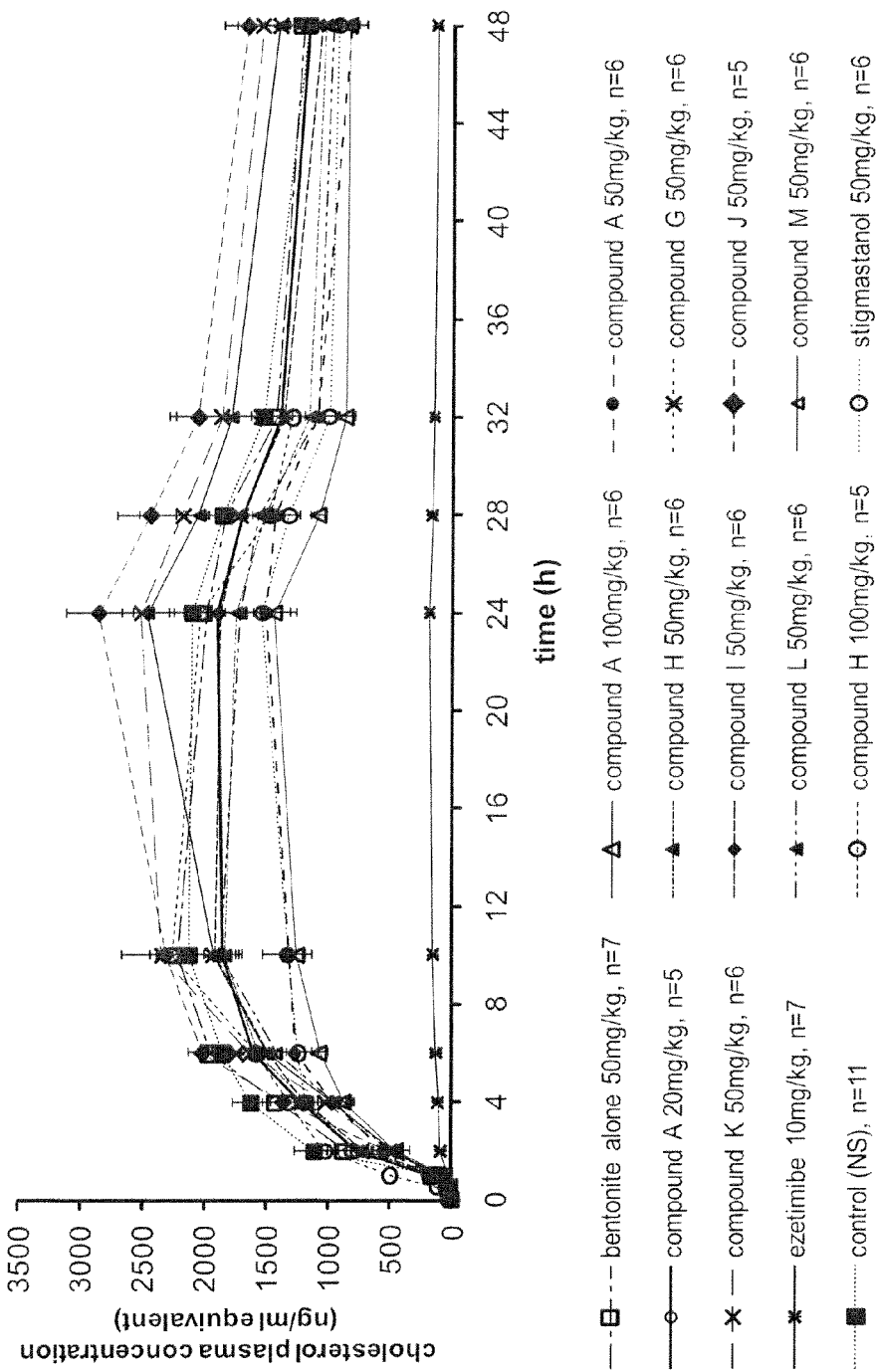
FIG. 9 shows the effects of various layered phyllosilicate materials compared to controls in a severe dyslipidemic model.

The plasma-concentration profiles of radioactive cholesterol following its oral administration of tested materials: The plasma concentration-time profiles of radioactive cholesterol (expressed as ng/ml equivalents) following administration of cholesterol with the layered phyllosilicate materials, ezetimibe (positive control) or stigmastanol (positive control) and with normal saline (negative/vehicle control) are shown in FIG. 9. FIG. 9 shows that the magnitude of the exposure, but not the shape of the profiles is affected by different treatments. This indicates that the observed changes are related mostly to the adsorption stage rather than to subsequent distribution or elimination issues. This is not surprising since layered phyllosilicate materials are not absorbed following oral administration and their effects are localized within the intestinal lumen. It should be noted that the mechanisms of action of both positive controls, ezetimibe and stigmastanol, are also related to the intestinal absorption stage of cholesterol homeostasis.

Figure 10:
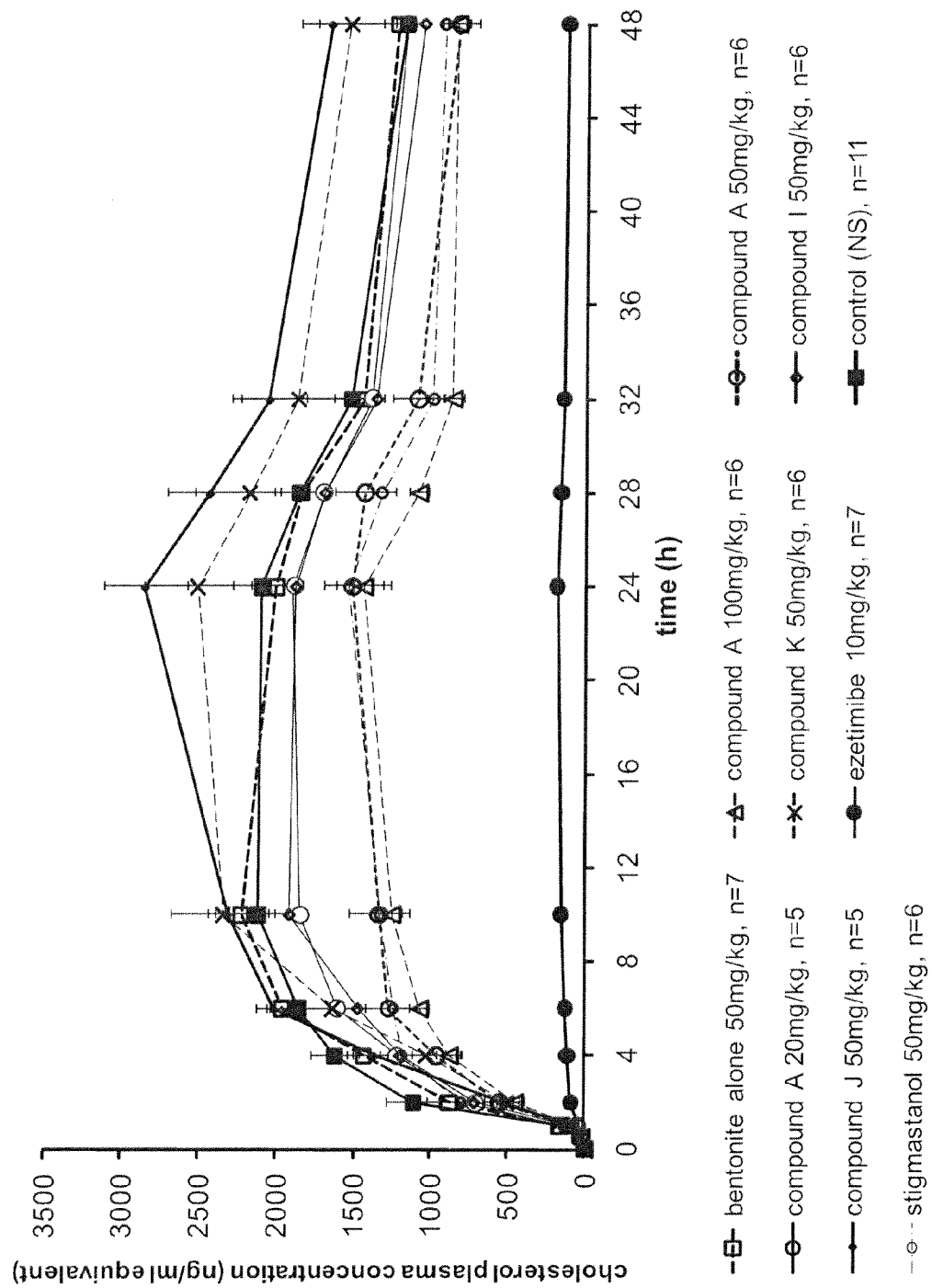
FIG. 10 shows the effects of various hydrogen protonated layered phyllosilicate materials compared to controls in a severe dyslipidemic model.
Figure 11:
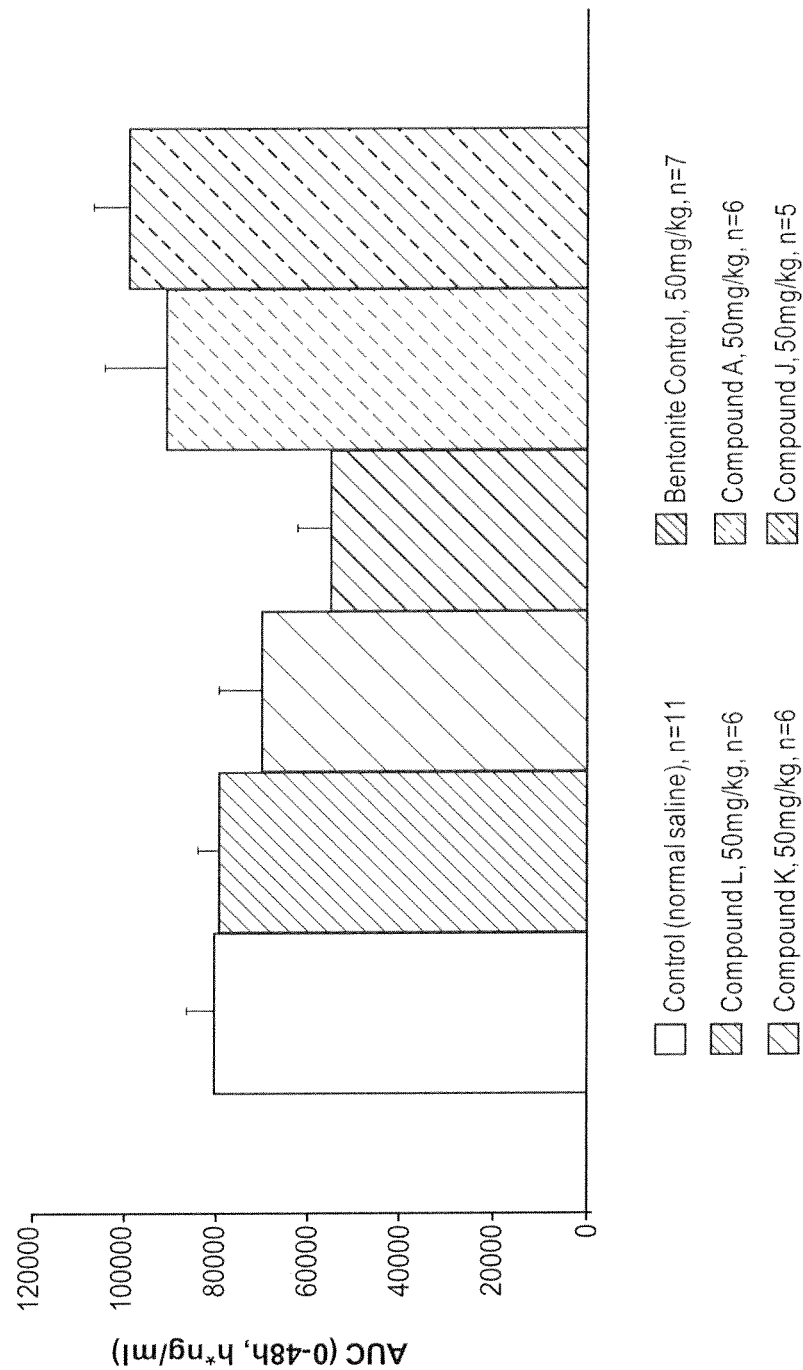
FIG. 11 shows the effects of various layered phyllosilicate materials (in area under curve values) compared to controls in a severe dyslipidemic model.

Effects of hydrogen protonation of a layered phyllosilicate material on its efficacy on the inhibition of intestinal cholesterol absorption: The areas under the curve ($AUC_{0-48\,h}$) calculated from plasma concentration-time profiles of the normal saline group (vehicle control), sodium bentonite control group, Compound A (50 mg/kg), Compound K (50 mg/kg) are shown in FIGS. 10 and 11. There is a statistically significant 31.5% reduction in cholesterol absorption in rats treated with Compound A ($AUC_{0-48\,h}$=55400±7555 h*mg/ml, mean±SEM) compared to the control animals ($AUC_{0-48\,h}$ 80861±5911 h*mg/ml, mean±SEM). In contrast, no significant differences were seen between the control animals and rats that received the same dose (50 mg/kg) of the sodium bentonite control ($AUC_{0-48\,h}$=79744±4707 h*mg/ml, mean±SEM) or Compound I ($AUC_{0-48\,h}$=70718±9019 h*mg/ml, mean±SEM). Conversion of Compound A back to a sodium form (i.e., Compound K) resulted in a loss of effect on cholesterol absorption ($AUC_{0-48\,h}$=90992±13460 h*mg/ml, mean±SEM). These results suggest that hydrogen protonation of a layered phyllosilicate material by means of an ion-exchange column increases its efficacy in regards to inhibition of intestinal cholesterol absorption. Taking into consideration previous reports of cholesterol molecules to bentonite clay (Nikkila et al., Ann. Med. Exp. Biol. Fenn., 30:51-58, 1952), the results suggest that Compound A (hydrogen protonated layered phyllosilicate material) reduces the extent of cholesterol absorption by direct adsorption of cholesterol molecules in the gastrointestinal tract. Other mechanisms are also possible under in vivo conditions. For example, adsorption of bile acids, fatty acids, monoglycerides or other constituents of cholesterol-containing mixed micelles to the layered phyllosilicate material or alteration in the lipolysis process of co-administered lipid-based formulation. This result is also supported by the in vitro effects of food grade silicon dioxide on the adsorption of bile salts (Peluso et al., J. Nutr., 124:853-860, 1994) and the adsorption of bile salts by bismuthsubsalicylate and montmorillonite, the active components in Pepto-Bismol® (Kocoshis et al., Dig. Dis. Sci., 24:1148-1152, 1984). Interestingly, protonating a layered phyllosilicate material by hydrochloric acid (i.e., Compound J) failed in regards to its efficacy of the compound in inhibition of cholesterol absorption ($AUC_{0-48\,h}$=99511±7415 h*mg/ml, mean±SEM).

Figure 12:
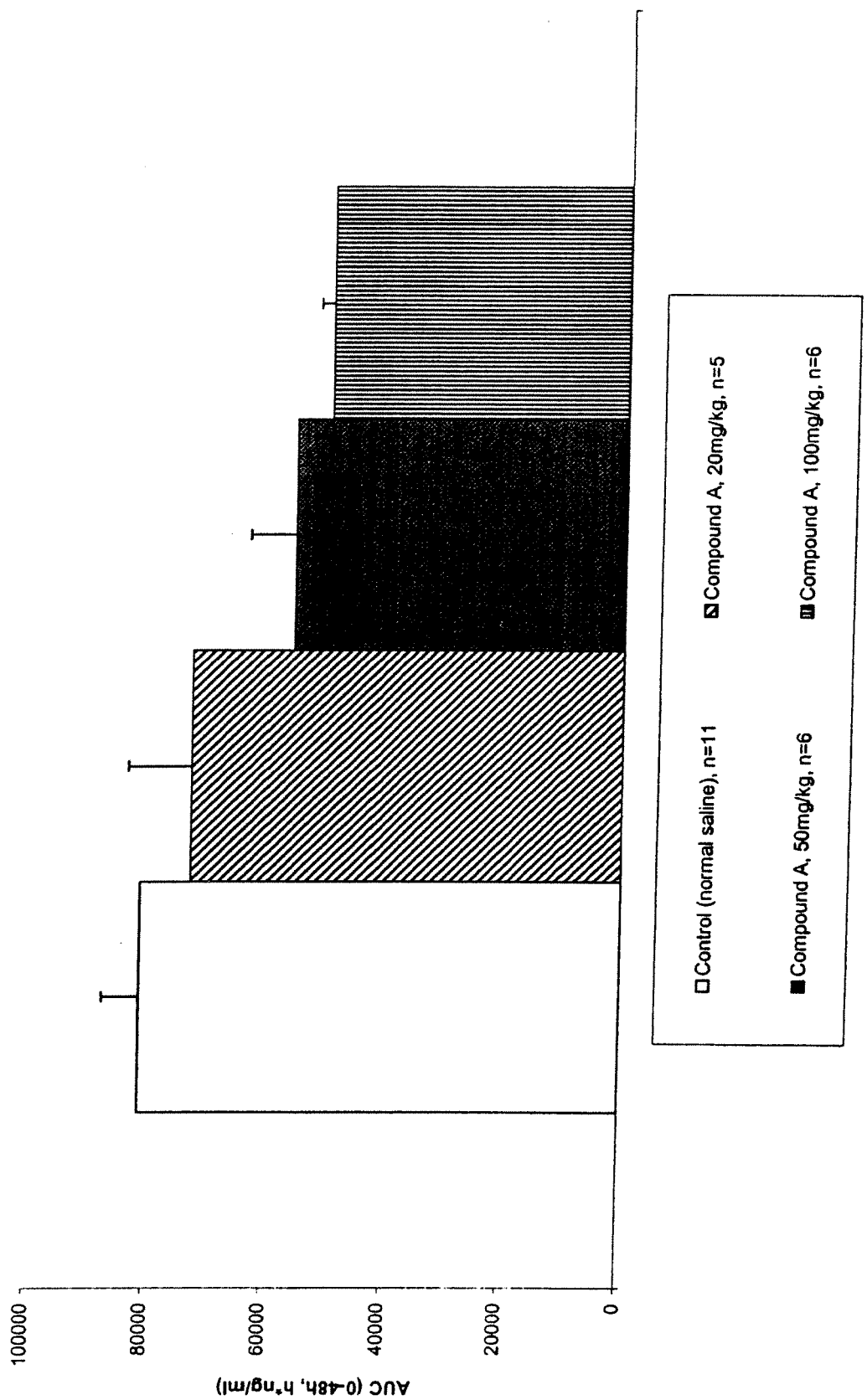
FIG. 12 shows the effects of various hydrogen protonated layered phyllosilicate materials (in area under curve values) compared to controls in a severe dyslipidemic model.

The dependence of the degree of inhibition of cholesterol absorption upon the dose of Compound A: FIG. 12 shows the dependence of exposure to radioactive cholesterol ($AUC_{0-48\,h}$) on the dose of Compound A administered at either 0 mg/kg (control), 20 mg/kg, 50 mg/kg, and 100 mg/kg. Administration of both 50 mg/kg ($AUC_{0-48\,h}$=55400±7555 h*mg/ml, mean±SEM) and 100 mg/kg ($AUC_{0-48\,h}$=49609±2090 h*mg/ml, mean±SEM), but not 20 mg/kg ($AUC_{0-48\,h}$=72227±10560 h*mg/ml, mean±SEM), results in a statistically significant decrease in cholesterol absorption compared to the control. As the dose of Compound A is increased, there is a trend of increase in effect, while the variability in response to treatment is decreased. However, although there is a continued trend to decrease cholesterol absorption when the dose is increased from 20 mg/kg to 50 mg/kg and then to 100 mg/kg, this increase in effect between groups (dose dependence) was not found to be statistically significant.

Figure 13:
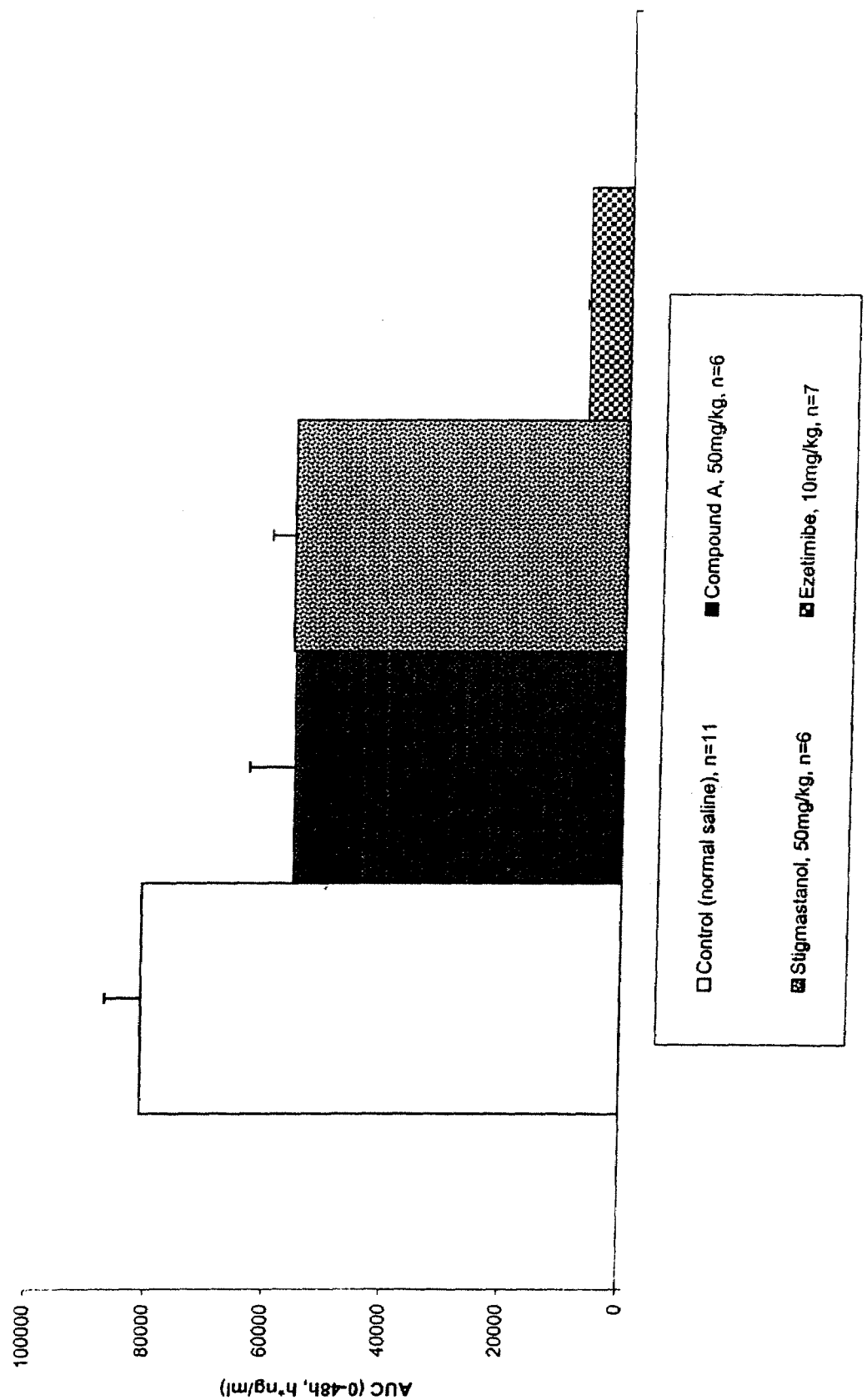
FIG. 13 shows the effects of a hydrogen protonated layered phyllosilicate material (in area under curve values) compared to stigmastanol and ezetimibe in a severe dyslipidemic model.

Comparison of Compound A to cholesterol absorption inhibitors in clinical use: FIG. 13 shows the comparison of exposure to radiolabeled cholesterol when administered with normal saline (vehicle control) ($AUC_{0-48\,h}$=80861±5911 h*mg/ml, mean±SEM), 50 mg/kg Compound A ($AUC_{0-48\,h}$=55400±7555 h*mg/ml, mean±SEM), 50 mg/kg stigmastanol ($AUC_{0-48\,h}$=55742±3764 h*mg/ml, mean±SEM) or with 10 mg/ml ezetimibe ($AUC_{0-48\,h}$=6937±462 h*mg/ml, mean±SEM). Results indicated that both Compound A and stigmastanol induces the same statistically significant inhibition in intestinal cholesterol absorption compared to the control. Treatment with ezetimibe resulted in higher inhibition of intestinal cholesterol absorption than Compound A or stigmastanol.

Conclusions: The results suggest that surface-modified layered phyllosilicate materials, such as those described herein, appear to be an effective adjuvant treatment for hypercholesteremia in rats at the level of inhibition of intestinal cholesterol absorption. Protonation of a layered phyllosilicate material by an ion-exchange column resulted in an increase in efficacy in reducing cholesterol absorption.

The foregoing results confirm that Compounds A, G, H and I exhibit a cholesterol-lowering activity in a severe dyslipidemic model, with Compound A demonstrating increased efficacy when compared to the other layered phyllosilicate materials. Thus, the use of Compound A, or any other hydrogen protonated layered phyllosilicate material, for the treatment of hypercholesteremia is considered as one aspect of the invention. Also contemplated is the use of a purified sodium layered phyllosilicate material for the treatment of hypercholesteremia.

Example 13

Layered Phyllosilicate Material Reduces Plasma Cholesterol Concentrations in ApoE-Deficient Mice The experiments reported in Lukic et al (Metabolism, 52:425-431, 2003; the disclosure of which is incorporated herein by reference in its entirety) will be performed and the effects of a layered phyllosilicate material described herein on plasma cholesterol levels in ApoE-deficient mice will be determined. It is contemplated that treatment with a layered phyllosilicate material described herein will result in reduced plasma cholesterol concentration compared to a control.

Example 14

Layered Phyllosilicate Material Reduced Atherosclerotic Lesion Formation in ApoE-Deficient Mice The following Example demonstrates that administration of a layered phyllosilicate material reduced atherosclerotic lesion formation in Apo-E-deficient mice (Lukic et al Metabolism, 52:425-431, 2003), more than would be expected based on the reduced level of cholesterol in the blood of the mice tested. Apo-E mice were chosen as an appropriate animal model because these mice develop severe hypercholesteremia and atherosclerotic lesions that are similar in distribution and appearance to those observed in humans, Animal model: C57B1/6 B6.129P2-ApoE™1USN mice, 4 weeks old with homozygous deletion of the ApoE gene were purchased from Jackson Laboratories, U.S.A. These animals exhibit severe hypercholesteremia following the consumption of a high cholesterol diet (Moghadasian et al., Atheroscler. Thromb. Vasc. Biol., 17:119-126, 1997; Moghadasian et al., Life Sci., 64:1029-1036, 1999, the disclosures of which are incorporated herein by reference in their entireties).

Rodent Diet: Low fat (LF) and high fat high cholesterol (HF) diets were purchased from Research Diets, Inc. LF=10 kcal % fat. HF=45 kcal % fat. Compound A (prepared as described above in Example 2) at varying doses, Stigmastanol and Simvastatin were incorporated into commercially-available diets (Research Diets, Inc.). The composition of the various diets is set forth below in Table 6, which is appended hereto.

Treatment Groups: The mice were separated in one of the following nine treatment groups: (1) HF diet containing 0.11% w/w Compound A; (2) HF diet containing 0.6% w/w Compound A; (3) HF diet containing 1.4% w/w Compound A; (4) HF diet containing 2% w/w Compound A; (5) HF diet containing 2% w/w Stigmastanol (positive control); (6) HF diet containing 0.03% w/w Simvastatin (negative control); (7) HF diet alone (no treatment) (control); (8) LF diet alone (no treatment); and (9) LF diet containing 2% w/w Compound A. Several ApoE mice were removed from the study before initiation of treatment due to sickness and loss of weight not associated with Compound A. Sickness and weight loss is a common phenotype of ApoE deficient mice.

Experimental design: Upon receipt, 61 mice were randomly separated into 9 groups, house in cages, and fed with a LF diet. After two weeks acclimatization, the mice were assigned based on their total plasma cholesterol level and weight (with no statistically significant differences between total plasma cholesterol and weight) into one of the 9 treatment groups identified above. All animals had unlimited access to diets and water. Weight was measure biweekly and food intake was measured weekly. Blood samples were withdrawn at baseline and then every two weeks from the saphenous vein and collected in EDTA tubes, centrifuged (10,000 rpm at 4° C. for 15 minutes), and plasma was harvested. Total plasma cholesterol and triglyceride levels were determined using enzymatic kits. At the end of 12 weeks, all mice were sacrificed using $CO_2$. Blood was taken from the right ventricle. The hearts of the animals were perfused slowly with 1 mL of 10% buffered formalin solution (BFS) through the left ventricle. The hearts with aortas were removed and stored in 10% BFS for the analysis of atherosclerotic lesions. The total duration of the study was 14 weeks.

Qualitative analysis of atherosclerotic lesions: The tissue surrounding the aorta, including all fat, was trimmed and frozen in liquid nitrogen. The aorta was cut in 3 consecutive slices (10 μmol/L) 5 mm above the aortic root. Slides were stained with Oil-Red-O, Movat's Pentachrome and Hematoxylin-eosin. An independent pathologist, blinded to the treatment groups scored the lesion formation based on four criteria (1) exposure area; (2) maximum thickness of the lesion; (3) viability; and (4) % of aorta that has some lesion.

Statistical analysis: Results were expressed as mean±SEM. In order to assess the differences between treatment groups and the untreated control group, a one-way ANOVA test followed by Tukey-Kramer multiple comparison test or Dunnet multiple comparison test were used. A p-value of <0.05 indicated significant differences between groups.

Results: Based on physical appearance, none of the animals appeared to have any deleterious effects from the administration of Compound A. Their fur was white, shiny and healthy. The activity and behavior of the animals were similar between all groups and consistent with the ApoE deficient phenotype.

The baseline of the body weight was 19 g (average) and after 12 weeks was 33.2 (average). As a result of similar food and water consumption during all period of study, the body weight increased by the same amount over the experimental period in all groups (treatment and control). The average food intake for all treatment and control groups throughout the duration of study was 3.14 g per day.

Figure 14:
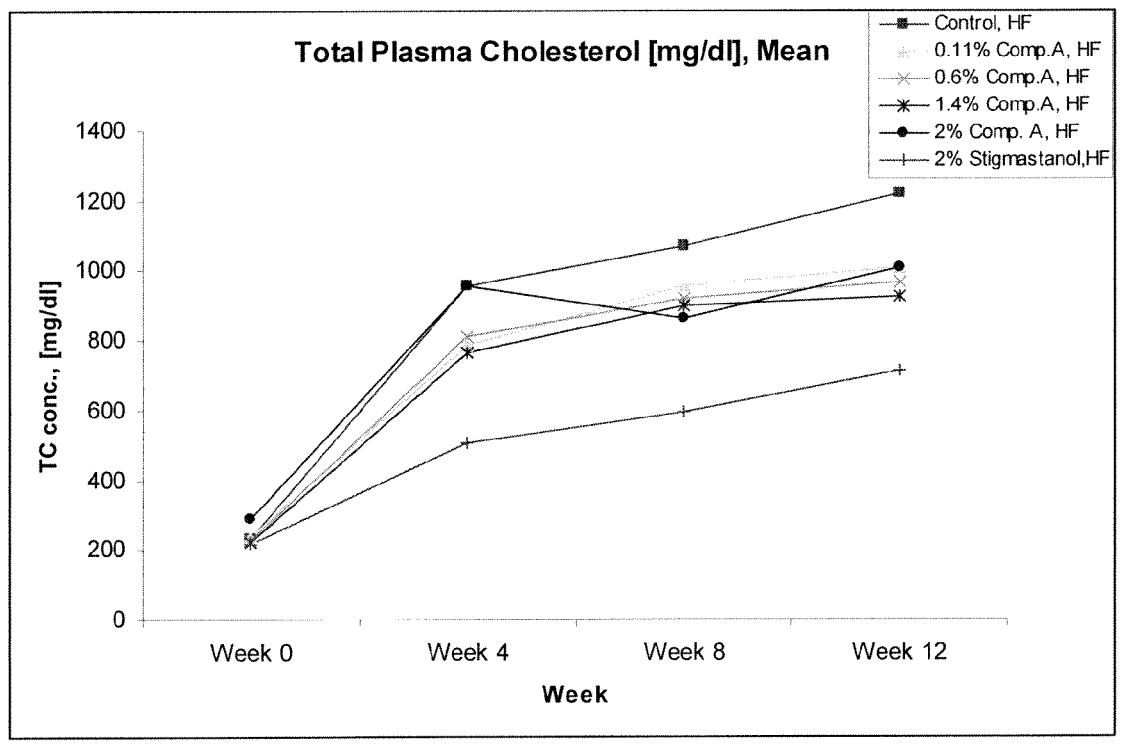
FIG. 14 shows the mean total plasma cholesterol (mg/dL) in mice treated with Compound A vs. various controls.

Plasma total cholesterol levels. The effects of Compound A on plasma total cholesterol are shown in FIG. 14 and Table 7. Control ApoE-deficient mice exhibited high plasma cholesterol levels compared to baseline.

TABLE 7

Total plasma cholesterol level (mg/dL) in mice treated with Compound vs. the various controls.

| | Group 1 LF n = 8 | Group 2 HF n = 8 | Group 3 0.11% A, HF n = 7 | Group 4 0.6% A, HF n = 8 | Group 5 1.4% A, HF n = 8 | Group 6 2% A, HF n-6 | Group 7 2% A, LF n = 5 | Group 8 2% stigmastanol, HF n = 7 | Group 9 0.03% simvastatin, HF n = 4 |
|---|---|---|---|---|---|---|---|---|---|
| | | | | | Mean | | | | |
| Week 0 | 223.2 | 2.32.5 | 238 | 225.6 | 224.4 | 288.8 | 252.3 | 215.3 | 272 |
| Week 4 | 388.4 | 955.8 | 786.7 | 809.5 | 766.1 | 956.7 | 414.7 | 505.7 | 1215.3 |
| Week 8 | 516.9 | 1066.9 | 957.7 | 919.6 | 899.9 | 861.4 | 422.9 | 595.1 | 915 |
| Week 12 | 510.7 | 1218.8 | 1008 | 967.9 | 924.4 | 1007.9 | 541.7 | 710.7 | 1114.1 |
| | | | | | S.D. | | | | |
| Week 0 | 61.9 | 76.9 | 84.9 | 59.7 | 67.1 | 44.1 | 50.4 | 45.9 | 37.9 |
| Week 4 | 26.3 | 83 | 171.7 | 219.1 | 110.9 | 218.1 | 172.5 | 56.3 | 155 |
| Week 8 | 69.9 | 113.8 | 232.4 | 137 | 207 | 344.5 | 124 | 81.5 | 97.3 |
| Week 12 | 121.2 | 342.1 | 271.5 | 249.7 | 141.4 | 385.9 | 158.8 | 98.7 | 96 |
| | | | | | S.E.M. | | | | |
| Week 0 | 21.9 | 27.1 | 32 | 21.1 | 23.7 | 18 | 22.5 | 17.3 | 19 |
| Week 4 | 9.3 | 29.3 | 64.8 | 77.4 | 39.2 | 89 | 77 | 21.2 | 77.5 |
| Week 8 | 24.7 | 40.2 | 88.8 | 48.4 | 73.2 | 140.6 | 55.4 | 30.8 | 48.7 |
| Week 12 | 42.8 | 120.9 | 102.4 | 88.2 | 50 | 157.5 | 70.9 | 37.2 | 48 |

The administration of Compound A at all concentrations: 0.11; 0.6; 1.4, and 2% in HF diet reduced the increase in total cholesterol between the beginning (Week 0) and the end (Week 12) of treatment comparing to a non-treated control. Administration of Compound A at the dosage of 1.4% in HF diet significantly decreased (by 29%) the increase (between the end (week 12) and the beginning (week 0); Δ(W12-W0)) in total cholesterol compared to the non-treated control. ($p<0.05$)

As expected, Stigmastanol significantly reduced (by 49.8%) the increase in total cholesterol. ($p<0.05$)

Plasma Triglyceride levels. No statistically significant differences in triglyceride levels were observed between all treatment groups, at all time points, relatively to the control animals. This observation, in addition to the fact that there were no changes in body weight and food intake throughout the study (data not shown) is indicative of the relative selectivity of Compound A to cholesterol absorption inhibition.

Figure 15:
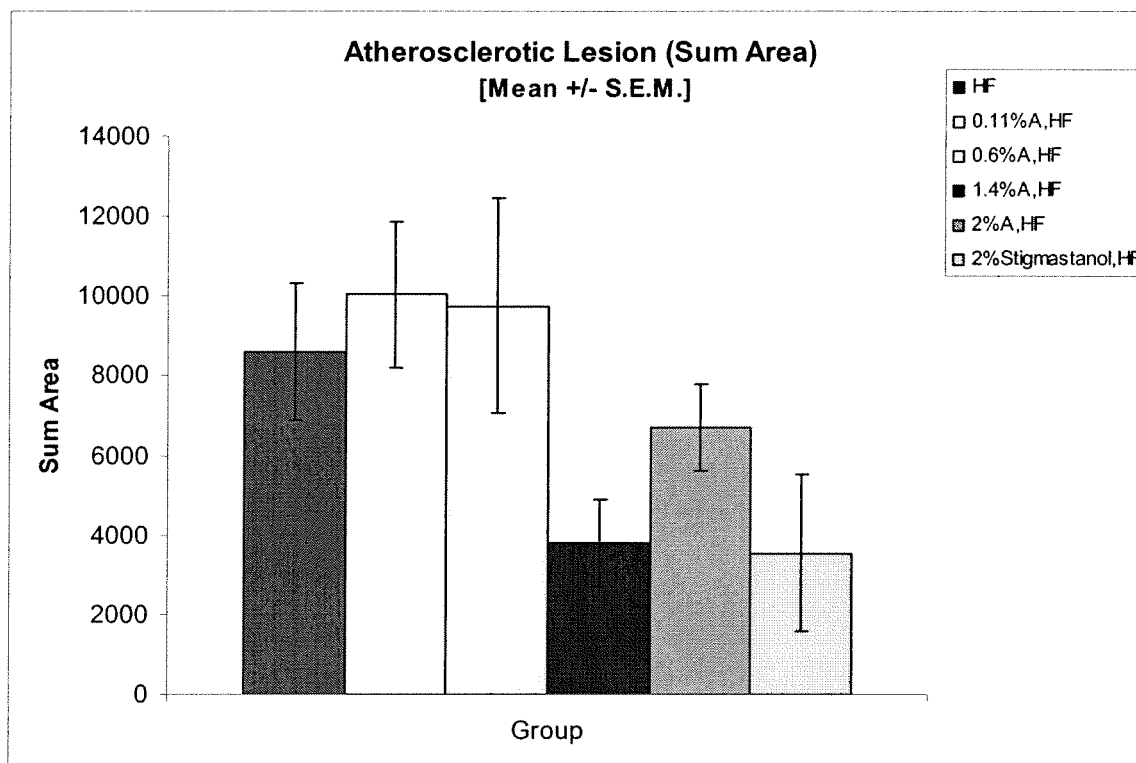
FIG. 15 is a graph showing the effect of various treatment groups on atherosclerotic lesion formation.
Figure 16:
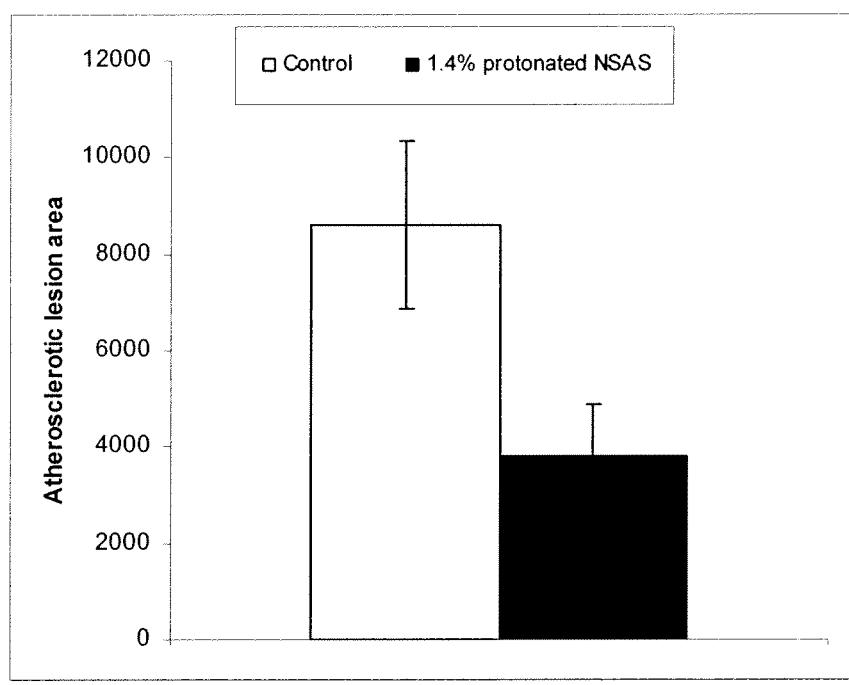
FIG. 16 is a graph showing the effect of treatment Compound A (1.4% w/w) on atherosclerotic lesion formation compared to untreated controls.

Atherosclerotic lesions. The effects of the various treatment groups on lesion formation is set forth in FIG. 15. The total lesion area in the Compound A 1.4% treatment group was statistically significantly (i.e., a 56% reduction in sum area) compared to the area of lesions in the untreated HF control animals. (FIG. 16). Stigmastanol at a dosage of 2% also had a statistically significant reduction (i.e., 58% reduction in the sum area) compared to untreated HF control. Administration of Compound A at a dosage of 2% in LF diet had a 71% reduction in sum area compared to untreated LF control.

Administration of Compound A at a dosage of 1.4% in HF diet had a 32% reduction in maximum thickness of the lesion compared to untreated HF control. Stigmastanol at a dosage of 2% in HF diet had a 50% reduction in maximum thickness of the lesion compared to untreated HF control.

Figure 17:
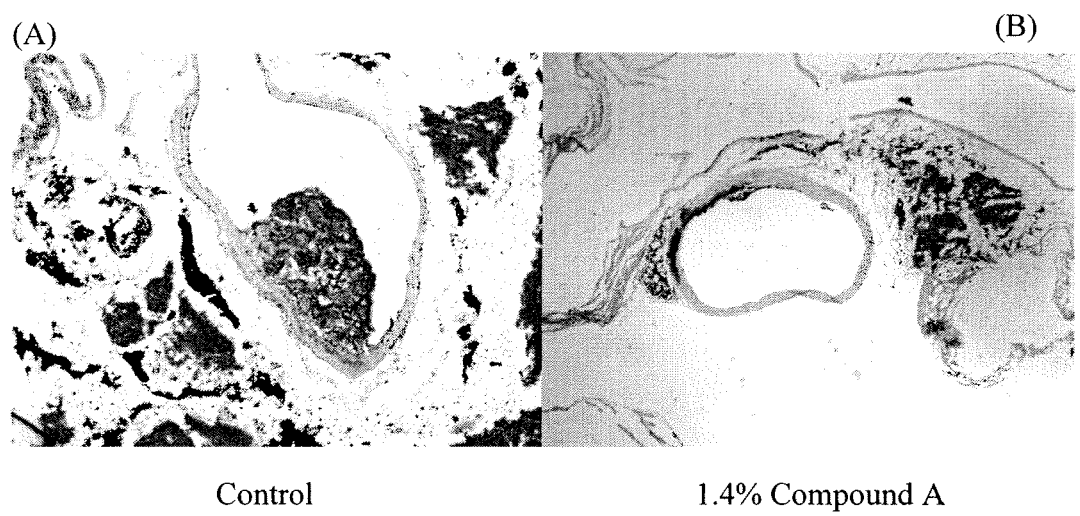
FIG. 17 shows representative aortic arches following 12 weeks of treatment with 1.4% w/w of Compound A (FIG. 17A) and an untreated control (FIG. 17B) in a HF diet.

The images of representative lesions in aortic roots of control group and 1.4% w/w Compound A treatment group (shown in FIG. 17A) visualize the area differences demonstrated in FIG. 16.

Conclusion: The results of this experiment demonstrated that treatment with Compound A at a dosage of 1.4% w/w over a 12 week period significantly reduced total plasma cholesterol concentrations by greater than 30% compared to the untreated controls. Surprisingly, this reduction in plasma cholesterol concentrations translated into a greater than 50% reduction in atherosclerotic lesion formation compared to the untreated controls. Interestingly, treatment with Compound A at the dose of 1.4% w/w appeared to be most effective while lower and higher doses of compound A were less effective.

The effect of the administration of Compound A on cholesterol absorption seems to be relatively selective, as demonstrated by absence of changes in plasma triglyceride concentrations and lack of differences in body weight and food intake. The shown significant effect of supplementation of high fat/high cholesterol diet with Compound A on the formation of atherosclerotic lesions is particularly important, since the final aim of cholesterol-lowering treatment is reduction of the development of atherosclerosis.

Without being limited to any particular theory, the greater lesion reduction compared to the plasma cholesterol concentration reduction may be attributed to the accumulative effect of a reduced cholesterol level over the duration of the study (i.e. 12 weeks). Alternatively, alterations in intestinal transit time, disruption of cholesterol micelles, effects on the paracellular and transcellular transport of cholesterol, alterations in influx and efflux gut transporters and potential alterations in gastrointestinal enzymes responsible for lipolysis or the formation of cholesterol micelles may be responsible for the surprising reduction in atherosclerotic lesions after treatment with Compound A.

Regardless of the exact mechanism responsible for the reduction in atherosclerotic lesions in the mice, the results provided herein demonstrate that Compound A is a candidate therapeutic for the treatment of cardiovascular disorders associated with atherosclerosis (or at least the treatment of atherosclerotic lesions) in mammalian subjects.

A 2% stanol dose in mice is effective in humans at a dose of 3 g/day/70 kg subject. The data presented herein demonstrated that Compound A was effective at a dose of 1.4% compared to the 2% stanol dose. Thus, in some embodiments, administration of Compound A at a dose of approximately 3 g/day/70 kg subject is specifically contemplated.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

TABLE 6

| | Product # | | | | | | | | | |
|---|---|---|---|---|---|---|---|---|---|---|
| | D08062102 HFHC 0.11% A | | D08062103 HFHC 0.6% A | | D08062104 HFHC 1.4% A | | D08062106 HFHC 2% Stigmastanol | | D08062107 HFHC 0.5% Simvastatin | |
| | gm | kcal | gm | kcal | gm | kcal | gm | kcal | gm | kcal |
| % | | | | | | | | | | |
| Protein | 23 | 20 | 20 | 20 | 16 | 20 | 23 | 20 | 23 | 20 |
| Carbohydrate | 40 | 35 | 34 | 35 | 28 | 35 | 41 | 35 | 41 | 35 |
| Fat | 23 | 45 | 19 | 45 | 16 | 45 | 23 | 45 | 23 | 45 |
| Total | | 100 | | 100 | | 100 | | 100 | | 100 |
| kcal/gm | 4.5 | | 3.9 | | 3.2 | | 4.6 | | 4.7 | |
| Ingredient | | | | | | | | | | |
| Casein, 80 Mesh | 200 | 800 | 200 | 800 | 200 | 800 | 200 | 800 | 200 | 800 |
| L-Cystine | 3 | 12 | 3 | 12 | 3 | 12 | 3 | 12 | 3 | 12 |
| Corn Starch | 72.8 | 291 | 72.8 | 291 | 72.8 | 291 | 72.8 | 291 | 72.8 | 291 |
| Maltodextrin 10 | 100 | 400 | 100 | 400 | 100 | 400 | 100 | 400 | 100 | 400 |
| Sucrose | 172.8 | 691 | 172.8 | 691 | 172.8 | 691 | 172.8 | 691 | 172.8 | 691 |
| Cellulose, BW200 | 50 | 0 | 50 | 0 | 50 | 0 | 50 | 0 | 50 | 0 |
| Soybean Oil | 0 | 0 | 0 | 0 | 0 | 0 | 0 | 0 | 0 | 0 |
| Lard | 202.5 | 1823 | 202.5 | 1823 | 202.5 | 1823 | 202.5 | 1823 | 202.5 | 1823 |
| Mineral Mix S10026 | 10 | 0 | 10 | 0 | 10 | 0 | 10 | 0 | 10 | 0 |
| DiCalcium Phosphate | 13 | 0 | 13 | 0 | 13 | 0 | 13 | 0 | 13 | 0 |
| Calcium Carbonate | 5.5 | 0 | 5.5 | 0 | 5.5 | 0 | 5.5 | 0 | 5.5 | 0 |
| Potassium Citrate, 1 H2O | 16.5 | 0 | 16.5 | 0 | 16.5 | 0 | 16.5 | 0 | 16.5 | 0 |
| Vitamin Mix V10001 | 10 | 40 | 10 | 40 | 10 | 40 | 10 | 40 | 10 | 40 |
| Choline Bitartrate | 2 | 0 | 2 | 0 | 2 | 0 | 2 | 0 | 2 | 0 |
| Cholesterol | 1.7 | 0 | 1.7 | 0 | 1.7 | 0 | 1.7 | 0 | 1.7 | 0 |
| Compound A (2.9% Active) | 32 | 0 | 179 | 0 | 420 | 0 | 0 | 0 | 0 | 0 |
| Stigmastanol | 0 | 0 | 0 | 0 | 0 | 0 | 17.6 | 0 | 0 | 0 |

TABLE 6-continued

| | | | | | | | | | | |
|---|---|---|---|---|---|---|---|---|---|---|
| Simvastatin | 0 | 0 | 0 | 0 | 0 | 0 | 0 | 0 | 4.4 | 0 |
| FD&C Yellow Dye #5 | 0 | 0 | 0 | 0 | 0 | 0 | 0.025 | 0 | 0 | 0 |
| FD&C Red Dye #40 | 0 | 0 | 0 | 0 | 0 | 0 | 0.025 | 0 | 0.025 | 0 |
| FD&C Blue Dye #1 | 0.005 | 0 | 0.025 | 0 | 0.05 | 0 | 0 | 0 | 0.025 | 0 |
| Total | 891.805 | 4057 | 1038.83 | 4057 | 1279.85 | 4057 | 877.45 | 4057 | 864.25 | 4057 |
| Compound A, % | 0.1 | | 0.5 | | 1.0 | | 0.0 | | 0.0 | |
| Stigmastanol, % | 0.0 | | 0.0 | | 0.0 | | 2.0 | | 0.0 | |
| Simvastatin, % | 0.0 | | 0.0 | | 0.0 | | 0.0 | | 0.5 | |
| Total needed for 5 kg | 179.411 | | 861.55 | | 1640.817 | | | | | |
| Compound A, solid, gm | 0.928 | | 5.191 | | 12.18 | | | | | |
| Weight of final diet, dry, gm | 860.73 | | 865.02 | | 872.03 | | | | | |
| Final dose based on dry diet, % | 0.11 | | 0.60 | | 1.40 | | | | | |

| | Product # | | | | | | | |
|---|---|---|---|---|---|---|---|---|
| | D08062108 LF | | D08062109 HFHC | | D08072501 LF 2% A | | D08072502 HFHC 2% A | |
| | gm | kcal | gm | kcal | gm | kcal | gm | kcal |
| % | | | | | | | | |
| Protein | 19 | 20 | 24 | 20 | 11 | 20 | 14 | 20 |
| Carbohydrate | 67 | 70 | 41 | 35 | 40 | 70 | 24 | 35 |
| Fat | 4 | 10 | 24 | 45 | 3 | 10 | 14 | 45 |
| Total | | 100 | | 100 | | 100 | | 100 |
| kcal/gm | 3.8 | | 4.7 | | 2.3 | | 2.8 | |
| Ingredient | | | | | | | | |
| Casein, 80 Mesh | 200 | 800 | 200 | 800 | 200 | 800 | 200 | 800 |
| L-Cystine | 3 | 12 | 3 | 12 | 3 | 12 | 3 | 12 |
| Corn Starch | 315 | 1260 | 72.8 | 291 | 315 | 1260 | 72.8 | 291 |
| Maltodextrin 10 | 35 | 140 | 100 | 400 | 35 | 140 | 100 | 400 |
| Sucrose | 350 | 1400 | 172.8 | 691 | 350 | 1400 | 172.8 | 691 |
| Cellulose, BW200 | 50 | 0 | 50 | 0 | 50 | 0 | 50 | 0 |
| Soybean Oil | 0 | 0 | 0 | 0 | 0 | 0 | 0 | 0 |
| Lard | 45 | 405 | 202.5 | 1823 | 45 | 405 | 202.5 | 1823 |
| Mineral Mix S10026 | 10 | 0 | 10 | 0 | 10 | 0 | 10 | 0 |
| DiCalcium Phosphate | 13 | 0 | 13 | 0 | 13 | 0 | 13 | 0 |
| Calcium Carbonate | 5.5 | 0 | 5.5 | 0 | 5.5 | 0 | 5.5 | 0 |
| Potassium Citrate, 1 H2O | 16.5 | 0 | 16.5 | 0 | 16.5 | 0 | 16.5 | 0 |
| Vitamin Mix V10001 | 10 | 40 | 10 | 40 | 10 | 40 | 10 | 40 |
| Choline Bitartrate | 2 | 0 | 2 | 0 | 2 | 0 | 2 | 0 |
| Cholesterol | 0 | 0 | 1.7 | 0 | 0 | 0 | 1.7 | 0 |
| Compound A (2.9% Active) | 0 | 0 | 0 | 0 | 742 | 0 | 605 | 0 |
| Stigmastanol | 0 | 0 | 0 | 0 | 0 | 0 | 0 | 0 |
| Simvastatin | 0 | 0 | 0 | 0 | 0 | 0 | 0 | 0 |
| FD&C Yellow Dye #5 | 0.05 | 0 | 0 | 0 | 0 | 0 | 0 | 0 |
| FD&C Red Dye #40 | 0 | 0 | 0 | 0 | 0.05 | 0 | 0 | 0 |
| FD&C Blue Dye #1 | 0 | 0 | 0.05 | 0 | 0 | 0 | 0.1 | 0 |
| Total | 1055.05 | 4057 | 859.85 | 4057 | 1797.05 | 4057 | 1464.9 | 4057 |
| Compound A, % | 0.0 | | 0.0 | | | | | |
| Stigmastanol, % | 0.0 | | 0.0 | | | | | |
| Simvastatin, % | 0.0 | | 0.0 | | | | | |
| Total needed for 5 kg | | | | | | | | |
| Compound A, solid, gm | | | | | 21.5 | | 17.5 | |
| Weight of final diet, dry, gm | | | | | 1076.6 | | 877.4 | |
| Final dose based on dry diet, % | | | | | 2.00 | | 2.00 | |

The invention claimed is:

1. A method of treating a cardiovascular disorder associated with atherosclerosis in a mammalian subject in need thereof comprising orally administering to said subject a hydrogen ion-exchanged layered phyllosilicate material in an amount effective to reduce atherosclerotic lesion formation in said subject.

2. The method of claim 1, wherein the cardiovascular disorder is selected from the group consisting of atherosclerosis, coronary heart disease, cerebral artery disease, peripheral artery disease, myocardial infarction, stroke, plaque rupture, plaque erosion, acute coronary syndrome, transient ischemia attack, angina, unstable angina, thrombosis, ischemic heart disease, coronary artery disease, and transplantation-induced sclerosis.

3. The method of claim 1, wherein the mammalian subject is afflicted with cardiovascular atherosclerosis, cerebrovascular atherosclerosis, peripheral vessel atherosclerosis, coronary heart atherosclerosis or a combination thereof.

4. The method of claim 1, wherein the mammalian subject is afflicted with obesity, insulin resistance, diabetes, hypertension, hypercholesteremia, or a combination thereof.

5. The method of claim 1, wherein the layered phyllosilicate material comprises at least 90% homoionic hydrogen cations, in relation to all interlayer exchangeable cations, and has a particle size less than 74 μm.

6. The method of claim 1, wherein the layered phyllosilicate material prevents synthesis and adsorption of cholesterol in or from the gastrointestinal tract thereby reducing of atherosclerotic lesion formation in the subject.

7. The method of claim 1, wherein the layered phyllosilicate material further comprises a pharmaceutically acceptable carrier, diluent or adjuvant.

8. The method of claim 1, wherein the mammalian subject is human.

9. The method of claim 8, further comprising administering a standard of care therapeutic to said subject.

10. The method of claim 9, wherein the standard of care therapeutic is a cholesterol-reducing agent.

11. The method of claim 10, wherein the cholesterol-reducing agent is selected from the group consisting of a statin-related agent, nicotinic acid, a fibrate, bile acid resins, a cholesterol absorption inhibitor, salicylic acid, a phytosterol, an alginate or a pectin, lecithin and a nutraceutical associated with cholesterol reduction.

12. The method of claim 11, wherein the statin-related agent is selected from the group consisting of lovastatin, atorvastatin, pravastatin, simvastatin and fluvastatin.

13. The method of claim 9, wherein the layered phyllosilicate material is administered concurrently with the therapeutic agent.

14. The method of claim 9, wherein the layered phyllosilicate material and the standard of care therapeutic are administered sequentially.

15. A method of treating a cardiovascular disorder associated with atherosclerosis in a mammalian subject in need thereof comprising orally administering to said subject a combination therapy comprising (a) a hydrogen ion-exchanged layered phyllosilicate material and (b) a standard of care therapeutic,
wherein the combination therapy is administered in an amount effective to reduce atherosclerotic lesion formation in said subject.

16. The method of claim 15, wherein the cardiovascular disorder is selected from the group consisting of atherosclerosis, coronary heart disease, cerebral artery disease, peripheral artery disease, myocardial infarction, stroke, plaque rupture, plaque erosion, acute coronary syndrome, transient ischemia attack, angina, unstable angina, thrombosis, ischemic heart disease, coronary artery disease, and transplantation-induced sclerosis.

17. The method of claim 15, wherein the mammalian subject is afflicted with cardiovascular atherosclerosis, cerebrovascular atherosclerosis, peripheral vessel atherosclerosis, coronary heart atherosclerosis or a combination thereof.

18. The method of claim 15, wherein the layered phyllosilicate material comprises at least 90% homoionic hydrogen cations, in relation to all interlayer exchangeable cations, and has a particle size less than 74 μm.

19. The method of claim 15, wherein the mammalian subject is human.

20. The method of claim 15, wherein the standard of care therapeutic is a cholesterol-reducing agent.

21. The method of claim 20, wherein the cholesterol-reducing agent is selected from the group consisting of a statin-related agent, nicotinic acid, a fibrate, bile acid resins, a cholesterol absorption inhibitor, salicylic acid, a phytosterol, an alginate or a pectin, lecithin and a nutraceutical associated with cholesterol reduction.

22. The method of claim 21, wherein the statin-related agent is selected from the group consisting of lovastatin, atorvastatin, pravastatin, simvastatin and fluvastatin.

23. The method of claim 15, wherein the layered phyllosilicate material is administered concurrently with the standard of care therapeutic.

24. The method of claim 15, wherein the layered phyllosilicate material and the standard of care therapeutic are administered sequentially.

25. A method of treating a cardiovascular disorder associated with atherosclerosis in a mammalian subject in need thereof in which treatment with a standard of care therapeutic is contraindicated, wherein the method comprises orally administering to the subject a hydrogen ion-exchanged layered phyllosilicate material in an amount effective to reduce atherosclerotic lesion formation in the subject.

26. The method of claim 25, wherein the standard of care therapeutic is a cholesterol-lowering agent.

27. The method of claim 25, wherein the standard of care therapeutic is a plant sterol.

28. The method of claim 1, wherein the hydrogen ion-exchanged layered phyllosilicate material is prepared by contacting a layered phyllosilicate material having exchangeable cations that are predominantly sodium or calcium with a hydrogen ion-exchange resin.

* * * * *